(12) United States Patent
Jefferies et al.

(10) Patent No.: US 11,634,486 B2
(45) Date of Patent: Apr. 25, 2023

(54) ANTI-SEZ6L2 ANTIBODIES AND ANTIBODY DRUG CONJUGATES

(71) Applicant: Bluefin BioMedicine, Inc., Beverly, MA (US)

(72) Inventors: Kevin Jefferies, Brookline, MA (US); Scott Michael Lonning, Westford, MA (US); Nels Eric Pederson, Mansfield, MA (US); Jason G. Beaudet, Beverly, MA (US); Klarisa Rikova, Reading, MA (US); Aleksandr Tkachev, Cambridge, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 527 days.

(21) Appl. No.: 16/471,246

(22) PCT Filed: Dec. 22, 2017

(86) PCT No.: PCT/US2017/068098
§ 371 (c)(1),
(2) Date: Jun. 19, 2019

(87) PCT Pub. No.: WO2018/119351
PCT Pub. Date: Jun. 28, 2018

(65) Prior Publication Data
US 2021/0130454 A1 May 6, 2021

Related U.S. Application Data

(60) Provisional application No. 62/438,943, filed on Dec. 23, 2016.

(51) Int. Cl.
| | | |
|---|---|---|
| A61K 39/00 | (2006.01) | |
| C07K 16/28 | (2006.01) | |
| A61K 47/68 | (2017.01) | |
| A61P 35/00 | (2006.01) | |

(52) U.S. Cl.
CPC .......... *C07K 16/28* (2013.01); *A61K 47/6801* (2017.08); *A61P 35/00* (2018.01); *A61K 2039/505* (2013.01)

(58) Field of Classification Search
CPC ................................................ A61K 2039/505
See application file for complete search history.

(56) References Cited

U.S. PATENT DOCUMENTS

| | | |
|---|---|---|
| 7,309,765 B2 | 12/2007 | Goddard et al. |
| 7,495,082 B2 | 2/2009 | Goddard et al. |
| 8,889,354 B2 | 11/2014 | Bryant et al. |
| 9,676,850 B2 | 6/2017 | Saunders et al. |
| 9,963,747 B2 | 5/2018 | Bryant et al. |
| 9,993,566 B2 | 6/2018 | Liu et al. |
| 10,035,853 B2 | 7/2018 | Arathoon et al. |
| 2015/0018531 A1 | 1/2015 | Saunders et al. |
| 2017/0016069 A1 | 1/2017 | Osafune et al. |
| 2017/0349951 A1 | 12/2017 | Beurdeley et al. |

FOREIGN PATENT DOCUMENTS

| | | |
|---|---|---|
| EP | 2669682 A1 | 12/2013 |
| EP | 3297660 A2 | 3/2018 |
| WO | 2000/018804 A1 | 4/2000 |
| WO | 2014/144040 A1 | 9/2014 |
| WO | 2016/022883 A1 | 2/2016 |
| WO | 2016/177784 A1 | 11/2016 |
| WO | 2016/187508 A2 | 11/2016 |

OTHER PUBLICATIONS

Ishikawa et al. (Cancer Sci. Aug. 2006; 97 (8): 737-45).*
Greenspan et al. (Nature Biotechnology 1999; 7: 936-937).*
George et al. (Circulation. 1998; 97: 900-906).*
Nishioka et al. (Oncogene. Dec. 14, 2000; 19 (54) :6251-60).*
R&D Systems, Mouse SEZ6L2/BSRP-4 Antibody, 4 pages, (Nov. 12, 2010) [retrieved Sep. 19, 2019 https://www.rndsystems.com/search?keywords=SEZ6L2%2FBSRP-A].
UniProtKB, Access No. U2FVG2, 5-enolpyruvylshikimate-3-phosphate synthetase. 4 pages, Nov. 13, 2013.
International Search Report and Written Opinion for Application No. PCT/US2017/068098, dated May 8, 2018, 14 pages.
International Preliminary Report on Patentability for Application No. PCT/US2017/068098, dated Jul. 5, 2019, 9 pages.
Hald et al., Pancreatic islet and progenitor cell surface markers with cell sorting potential. Diabetologia. Jan. 2012;55 (1):154-65.
Ishikawa et al., Characterization of SEZ6L2 cell-surface protein as a novel prognostic marker for lung cancer. Cancer Sci. Aug. 2006;97(8):737-45.
Yaguchi et al., Sez6l2 regulates phosphorylation of ADD and neuritogenesis. Biochem Biophys Res Commun. Dec. 9, 2017;494(1-2):234-241.

* cited by examiner

*Primary Examiner* — Stephen L Rawlings
(74) *Attorney, Agent, or Firm* — Morgan, Lewis & Bockius LLP

(57) ABSTRACT

Disclosed herein are anti-Seizure Related 6 Homolog Like 2 (SEZ6L2) antibodies and antibody drug conjugates (ADCs), including compositions and methods of using said antibodies and ADCs.

4 Claims, 9 Drawing Sheets
Specification includes a Sequence Listing.

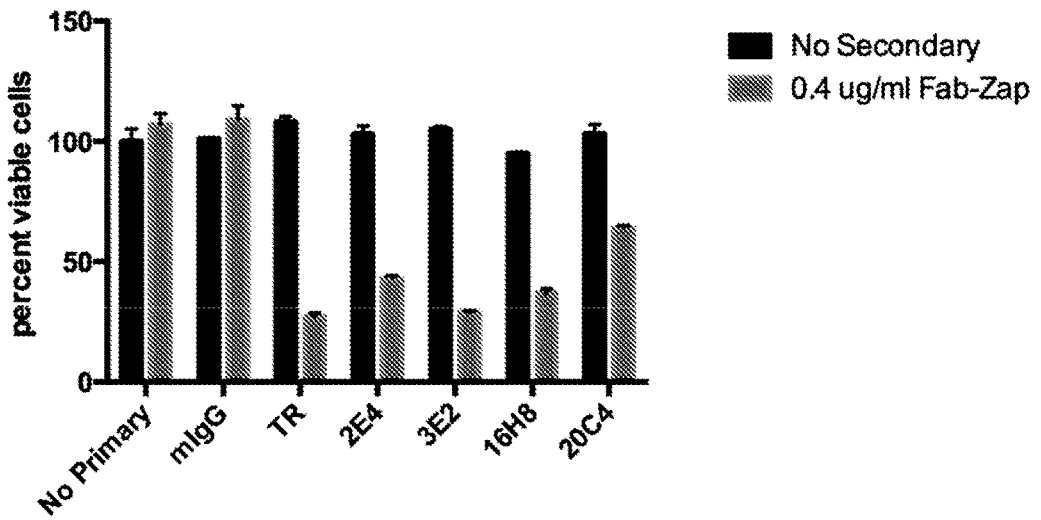
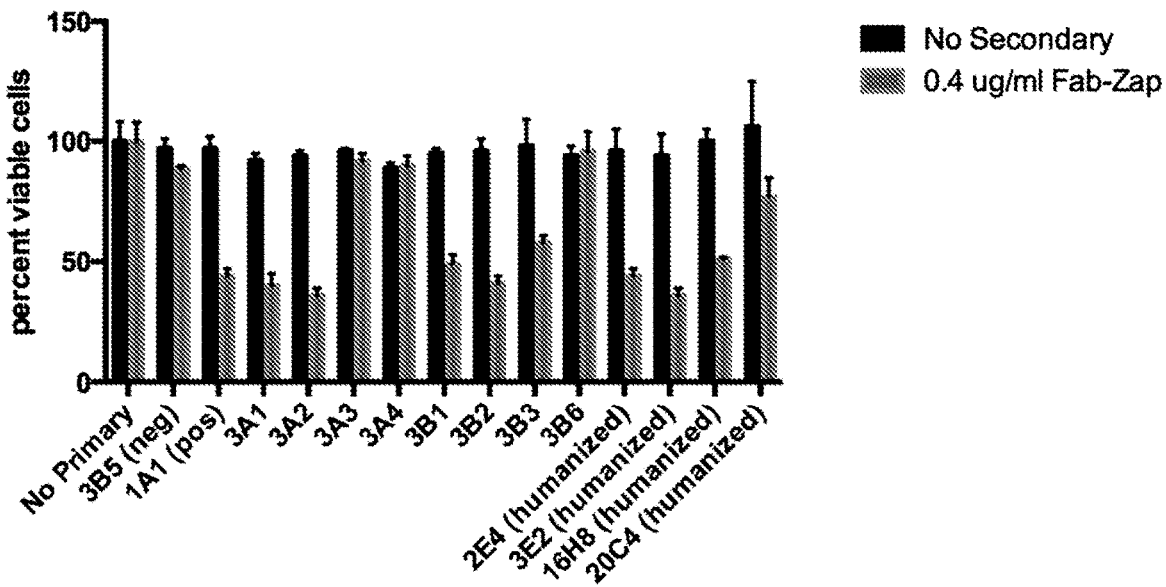
FIGURE 1 A–B

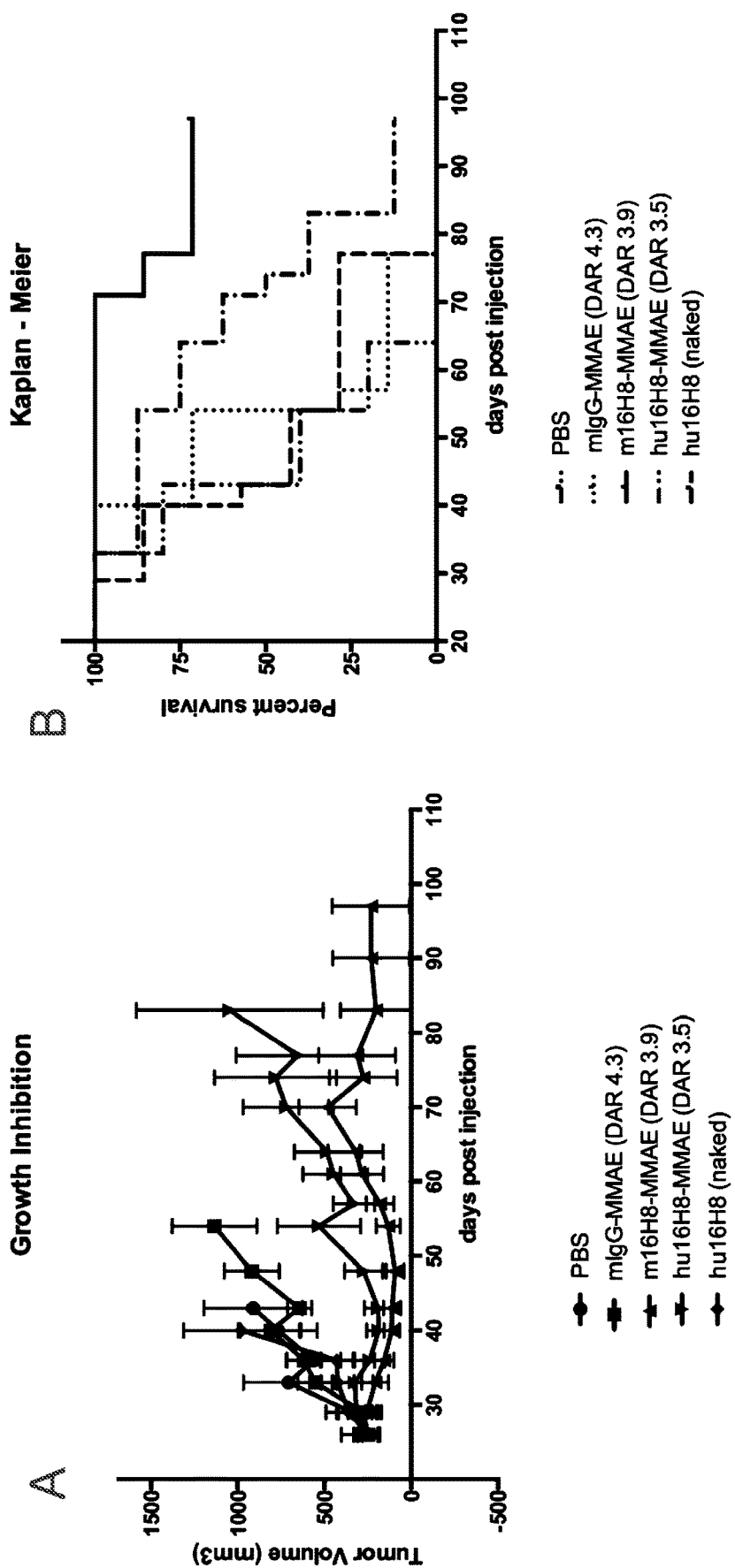
FIGURE 2 A-B

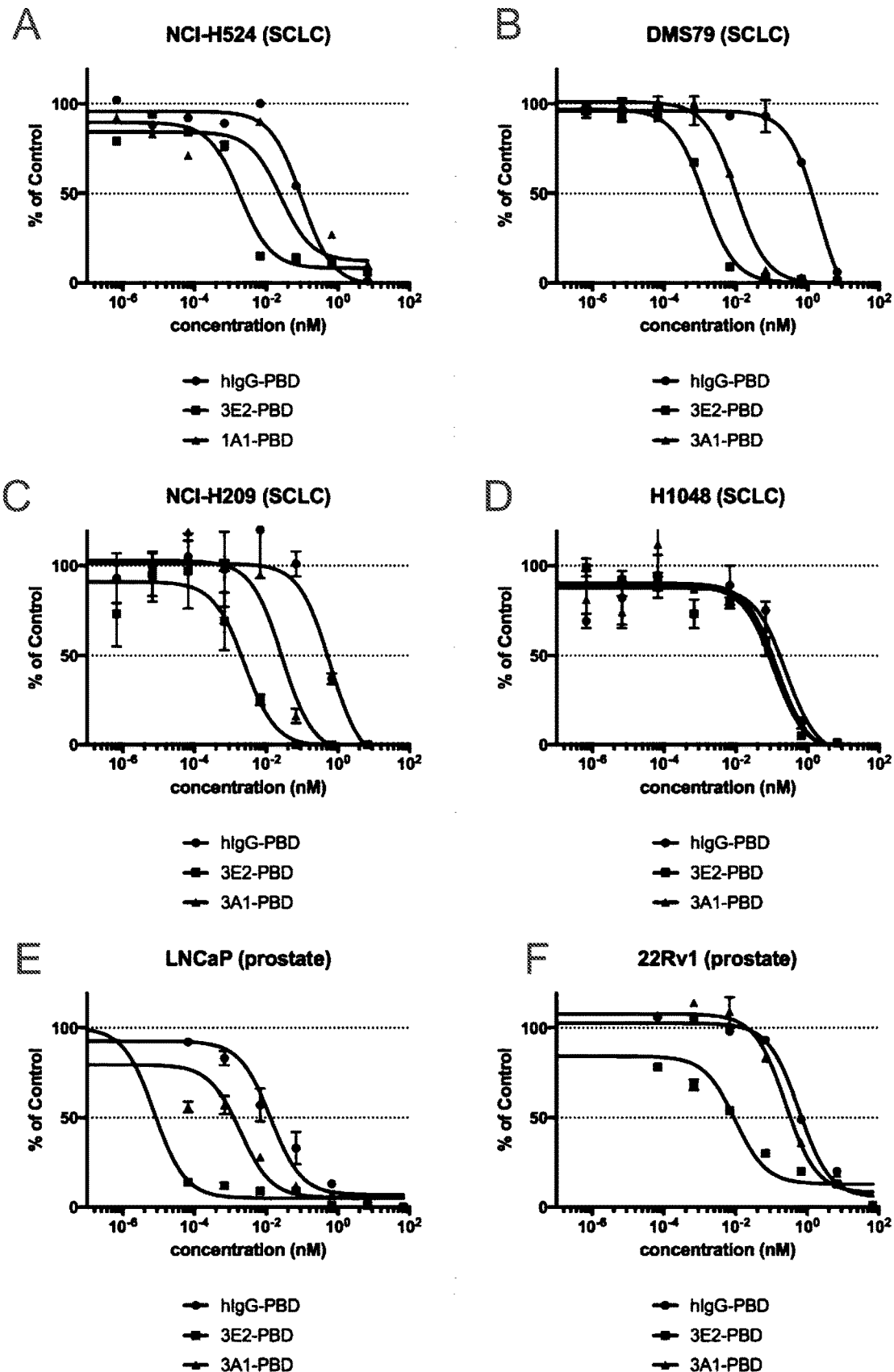
FIGURE 3 A–F

FIGURE 4 A-B
A
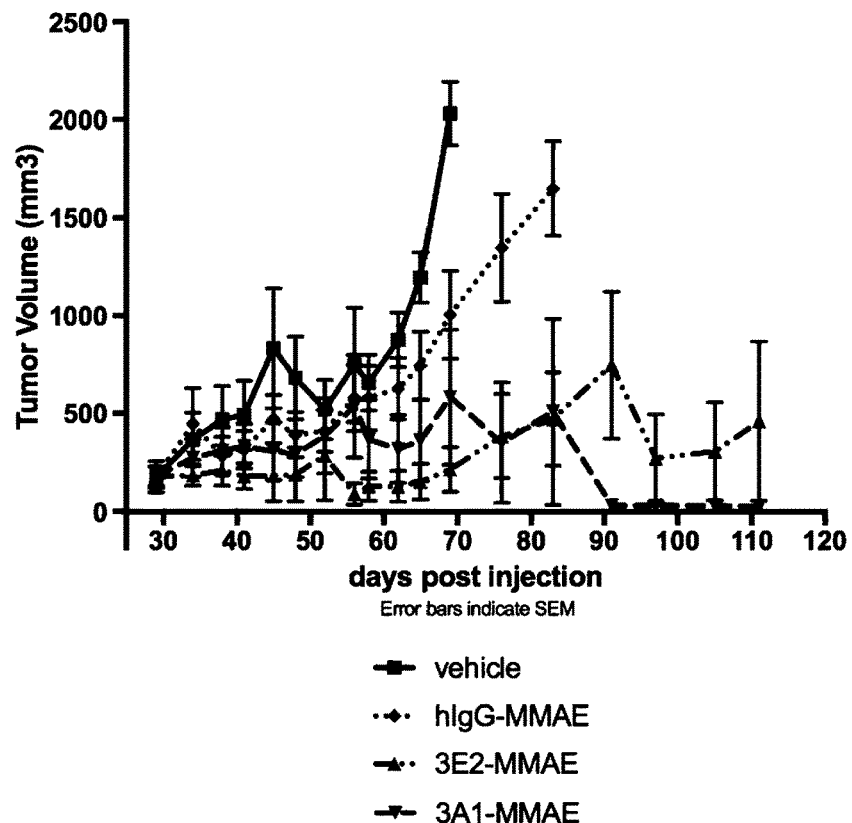
B
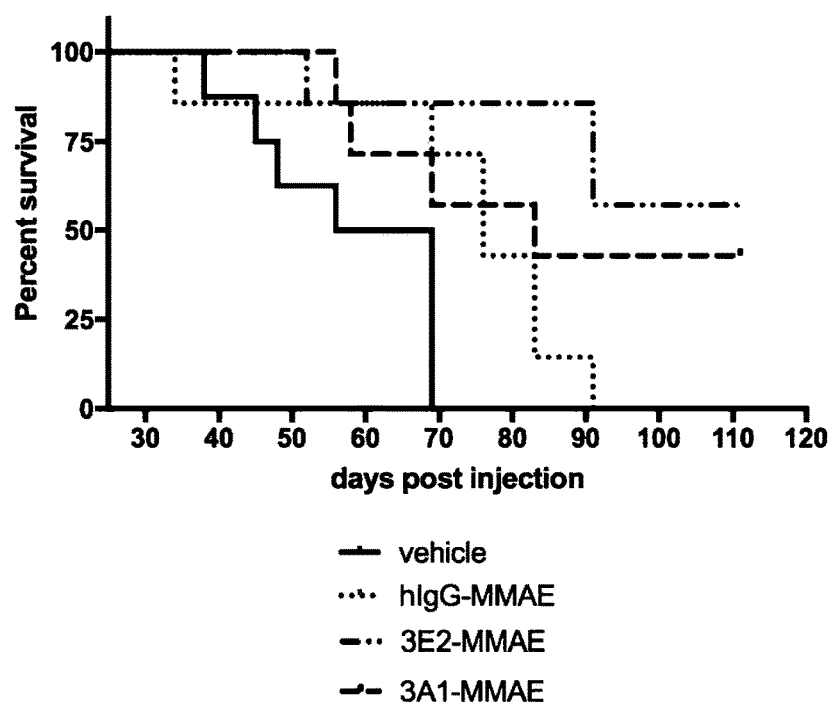

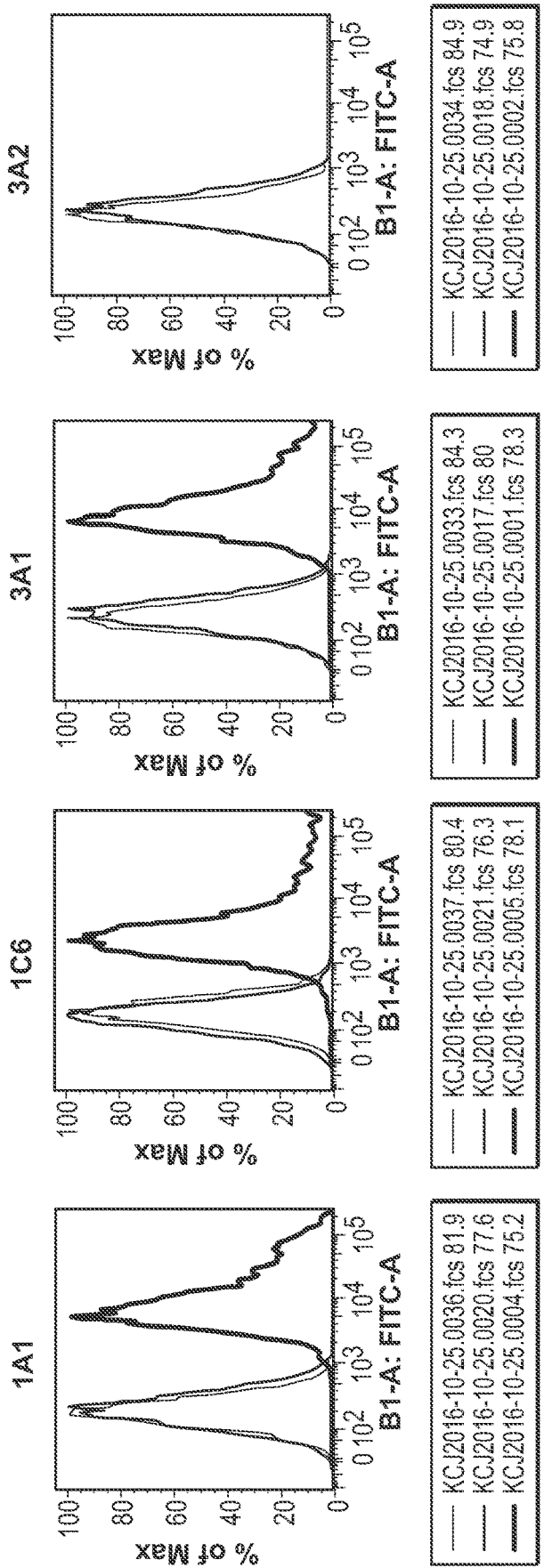

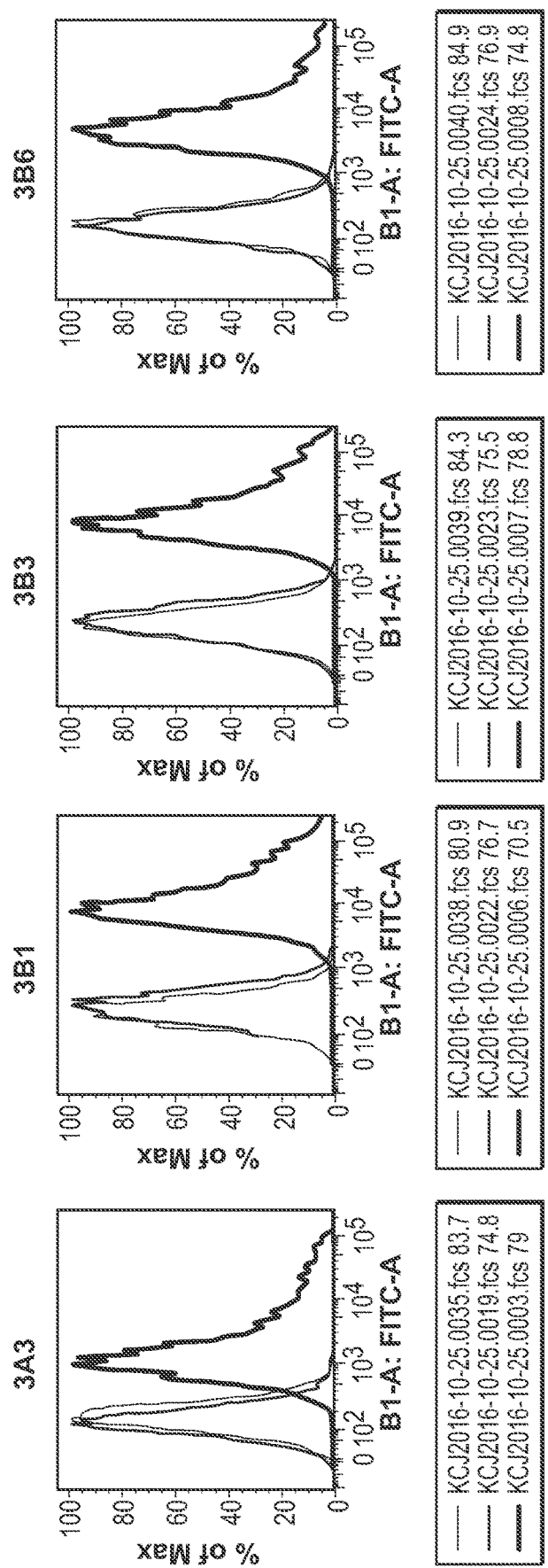
FIGURE 5 A-M (continued)

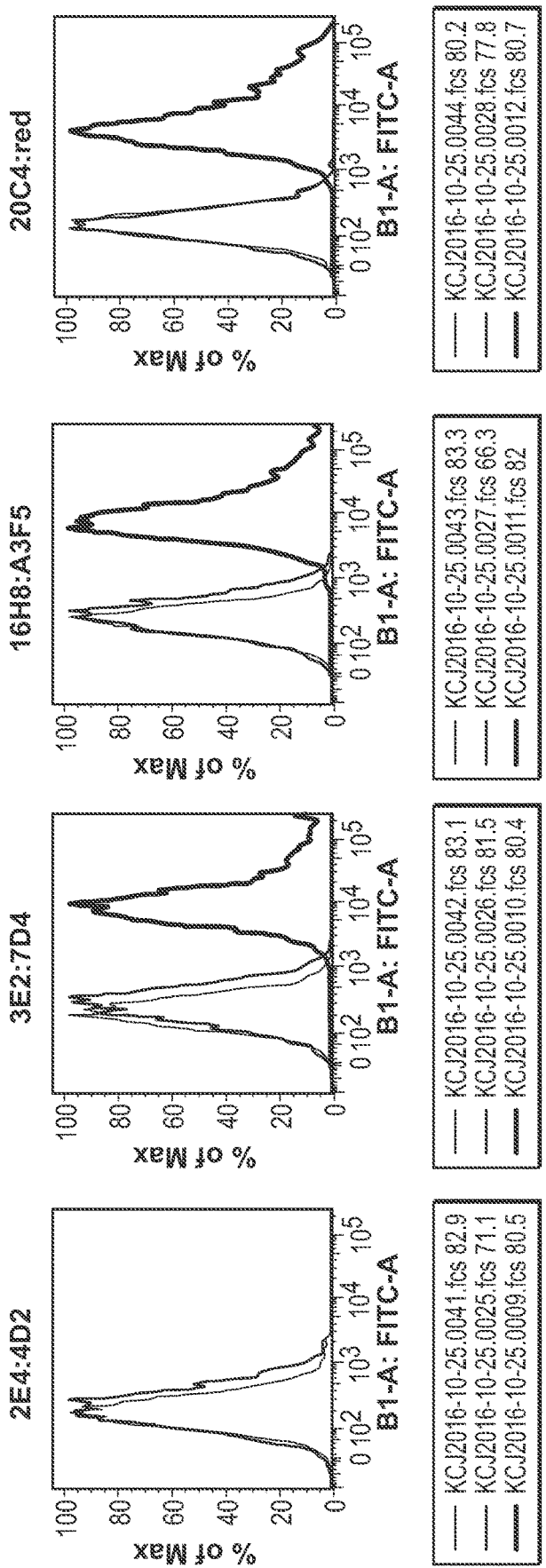
FIGURE 5 A-M (continued)

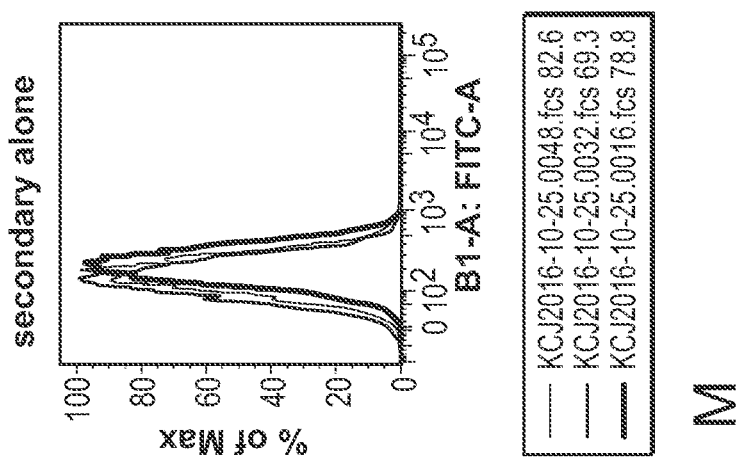
FIGURE 5 A-M (continued)

ANTI-SEZ6L2 ANTIBODIES AND ANTIBODY DRUG CONJUGATES

RELATED APPLICATIONS

The instant application is a 35 U.S.C. § 371 national stage filing of International Application No. PCT/US2017/068098, filed on Dec. 22, 2017, which in turn claims priority to U.S. Provisional Application No. 62/438,943, filed on Dec. 23, 2016, the entire contents of each of which are expressly incorporated by reference herein in their entirety.

SEQUENCE LISTING

The instant application contains a Sequence Listing which has been submitted electronically in ASCII format and is hereby incorporated by reference in its entirety. Said ASCII copy, created on Dec. 22, 2017, is named 127913-00120_SL.txt and is 133,786 bytes in size.

BACKGROUND

There are three members of the seizure related gene 6 (SEZ6) family; SEZ6, SEZ6L, and SEZ6L2 (also referred to as Seizure Related 6 Homolog (Mouse)-Like 2 and Seizure 6-Like Protein 2). SEZ6L2 is a ~155 kDa type 1 transmembrane glycoprotein with an N-terminal signal peptide, five SUSHI domains, three CUB domains, and a C-terminal transmembrane domain, and SEZ6L2 has approximately 41% sequence identity with the two other family members. Specifically, the SEZ6L2 gene was identified while screening a cDNA library following treatment with pentylentetrazole, a seizure inducing drug (Shimizu-Nishikawa K, et al. 1995 Brain Res Mol Brain Res 28:201-210; Shimizu-Nishikawa K, et al. 1995 Biochem Biophys Res Commun 216:382-389). There are 6 isoforms of SEZ6L2 produced by alternative splicing. The sequence homology between human SEZ6L2 and the mouse/rat and cynomolgus monkey homologs is 96% and 99%, respectively.

Though the normal physiologic role of SEZ6L2 is not fully understood, genetic variations in the SEZ6 family have been associated with febrile seizures, bipolar disorder I, and possibly autism (Yu ZL, et al. 2007 J Neurosci Res 85:166-172; Kumar R A, et al. 2009. PLoS One 4:e4582; Mulley J C, et al. 2011 Neurol Res Int 2011:917565; Konyukh M, et al. 2011 PLoS One 6:e17289; Xu C, 2013 J Affect Disord 145:95-99). Mice deficient for all three SEZ6 family members suffer from motor dis-coordination, cognitive defects and abnormal neuronal innervation (Miyazaki T, et al. 2006 FEBS Lett 580:4057-4064). It has also been suggested that SEZ6 modulates neuronal branching in mice (Gunnersen J M, et al. 2007 Neuron 56:621-639).

In murine neurons, SEZ6L2 has been shown to bind the aspartic protease cathepsin D and facilitate its trafficking from the trans-Golgi network to endosomes (Boonen M, et al. 2016 J Cell Sci 129:557-568). It has also been shown that cathepsin D is vital to normal neuronal function as its mutation or mislocalization is closely associated with neurodegenerative disease (Siintola E, et al. 2006 Brain 129:1438-1445; Steinfeld R, et al. 2006 Am J Hum Genet 78:988-998; Tyynela J, et al. 2000 EMBO J 19:2786-2792). Furthermore, it was shown that proteolytic cleavage of SEZ6L2 by cathepsin D releases a soluble N-terminal fragment that modulates neuronal differentiation (Boonen M, et al. 2016 J Cell Sci 129:557-568). SEZ6L2 has also been identified as a substrate of BACE2 and BACE1, proteases known as sheddases, in pancreatic-cells and primary neurons, respectively (Stutzer I, Set al. 2013 J Biol Chem 288:10536-10547; Hemming M L, et al. 2009 PLoS One 4:e8477).

Several proteomic and transcriptomic databases have suggested that SEZ6L2 is differentially upregulated in certain tumors. In addition, a survey of primary lung cancer specimens by Ishikawa, et al. (2006 Cancer Sci 97:737-745) found SEZ6L2 to be differentially expressed when comparing tumor to normal tissues. Ishikawa also found that 78% of non-small cell lung cancer (NSCLC) and 65% of small cell lung cancer (SCLC) specimens were positive for SEZ6L2 expression.

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-SEZ6L2 specific antibodies and ADCs that can be used for therapeutic purposes in the treatment of cancer.

SUMMARY

In certain aspects, the present disclosure provides for anti-SEZ6L2 antibodies and antibody drug conjugates (ADCs).

In one aspect, the disclosure provides anti-human Seizure Related 6 Homolog Like 2 (anti-hSEZ6L2) antibodies, ADCs, or antigen binding fragments thereof that inhibit tumor growth in an in vivo human small-cell lung carcinoma (SCLC) xenograft assay with a tumor growth inhibition % (TGI %) of at least about 50% relative to a human IgG antibody which is not specific for SEZ6L2, wherein the human IgG antibody is administered in the SCLC xenograft assay at the same dose and frequency as the anti-hSEZ6L2 antibodies, ADCs, or antigen binding fragments thereof.

In yet other aspects of the disclosure, the antibodies, ADCs, or antigen binding fragments thereof inhibit tumor growth by at least about 60% in an in vivo human SCLC xenograft assay relative to a human IgG antibody which is not specific for SEZ6L2. In certain embodiments, the disclosure features antibodies, ADCs, or antigen binding fragments thereof that inhibit tumor growth by at least about 70% in an in vivo human SCLC xenograft assay relative to a human IgG antibody which is not specific for SEZ6L2. In certain embodiments, the antibodies, ADCs, or antigen binding fragments thereof, inhibit tumor growth by at least about 80% in an in vivo human SCLC xenograft assay relative to a human IgG antibody which is not specific for SEZ6L2.

In certain embodiments of the disclosure, the antibodies, or antigen binding portions thereof, bind to huSEZ6L2, with a $K_d$ of between about 1 pM (0.001 nM) to 50 nM, between about 500 pM (0.5 nM) to 20 nM, between about 1 nM to 10 nM, or between about 1 nM to 5 nM.

In some embodiments, the antibodies, or antigen binding portions thereof, comprise a heavy chain variable region comprising a CDR3 having the amino acid sequence of SEQ ID NO: 4 and a light chain variable region comprising a CDR3 having the amino acid sequence of SEQ ID NO: 8; a heavy chain variable region comprising a CDR3 having the amino acid sequence of SEQ ID NO: 12 and a light chain variable region comprising a CDR3 having the amino acid sequence of SEQ ID NO: 16; a heavy chain variable region comprising a CDR3 having the amino acid sequence of SEQ ID NO: 20 and a light chain variable region comprising a CDR3 having the amino acid sequence of SEQ ID NO: 24; a heavy chain variable region comprising a CDR3 having the amino acid sequence of SEQ ID NO: 28 and a light chain variable region comprising a CDR3 having the amino acid sequence of SEQ ID NO: 31; a heavy chain variable region comprising a CDR3 having the amino acid sequence of SEQ ID NO: 35 and a light chain variable region comprising a CDR3 having the amino acid sequence of SEQ ID NO: 39; a heavy chain variable region comprising a CDR3 having the amino acid sequence of SEQ ID NO: 43 and a light chain variable region comprising a CDR3 having the amino acid sequence of SEQ ID NO: 46; a heavy chain variable region comprising a CDR3 having the amino acid sequence of SEQ ID NO: 35 and a light chain variable region comprising a CDR3 having the amino acid sequence of SEQ ID NO: 50; a heavy chain variable region comprising a CDR3 having the amino acid sequence of SEQ ID NO: 54 and a light chain variable region comprising a CDR3 having the amino acid sequence of SEQ ID NO: 58; a heavy chain variable region comprising a CDR3 having the amino acid sequence of SEQ ID NO: 62 and a light chain variable region comprising a CDR3 having the amino acid sequence of SEQ ID NO: 66; a heavy chain variable region comprising a CDR3 having the amino acid sequence of SEQ ID NO: 70 and a light chain variable region comprising a CDR3 having the amino acid sequence of SEQ ID NO: 72; a heavy chain variable region comprising a CDR3 having the amino acid sequence of SEQ ID NO: 76 and a light chain variable region comprising a CDR3 having the amino acid sequence of SEQ ID NO: 78; a heavy chain variable region comprising a CDR3 having the amino acid sequence of SEQ ID NO: 81 and a light chain variable region comprising a CDR3 having the amino acid sequence of SEQ ID NO: 83; a heavy chain variable region comprising a CDR3 having the amino acid sequence of SEQ ID NO: 87 and a light chain variable region comprising a CDR3 having the amino acid sequence of SEQ ID NO: 89; a heavy chain variable region comprising a CDR3 having the amino acid sequence of SEQ ID NO: 93 and a light chain variable region comprising a CDR3 having the amino acid sequence of SEQ ID NO: 95; a heavy chain variable region comprising a CDR3 having the amino acid sequence of SEQ ID NO: 99 and a light chain variable region comprising a CDR3 having the amino acid sequence of SEQ ID NO: 103; a heavy chain variable region comprising a CDR3 having the amino acid sequence of SEQ ID NO: 107 and a light chain variable region comprising a CDR3 having the amino acid sequence of SEQ ID NO: 89; a heavy chain variable region comprising a CDR3 having the amino acid sequence of SEQ ID NO: 112 and a light chain variable region comprising a CDR3 having the amino acid sequence of SEQ ID NO: 58; a heavy chain variable region comprising a CDR3 having the amino acid sequence of SEQ ID NO: 70 and a light chain variable region comprising a CDR3 having the amino acid sequence of SEQ ID NO: 119; a heavy chain variable region comprising a CDR3 having the amino acid sequence of SEQ ID NO: 236 and a light chain variable region comprising a CDR3 having the amino acid sequence of SEQ ID NO: 238; or a heavy chain variable region comprising a CDR3 having the amino acid sequence of SEQ ID NO: 242 and a light chain variable region comprising a CDR3 having the amino acid sequence of SEQ ID NO: 245.

In some embodiments, the antibodies, or antigen binding portions thereof, comprise a heavy chain variable region comprising a CDR3 as described herein and a light chain variable region CDR3 as described herein, and further comprise a heavy chain variable region comprising a CDR2 having the amino acid sequence of SEQ ID NO: 3 and a light chain variable region comprising a CDR2 having the amino acid sequence of SEQ ID NO: 7; a heavy chain variable region comprising a CDR2 having the amino acid sequence of SEQ ID NO: 11 and a light chain variable region comprising a CDR2 having the amino acid sequence of SEQ ID NO: 15; a heavy chain variable region comprising a CDR2 having the amino acid sequence of SEQ ID NO: 19 and a light chain variable region comprising a CDR2 having the amino acid sequence of SEQ ID NO: 23; a heavy chain variable region comprising a CDR2 having the amino acid sequence of SEQ ID NO: 27 and a light chain variable region comprising a CDR2 having the amino acid sequence of SEQ ID NO: 15; a heavy chain variable region comprising a CDR2 having the amino acid sequence of SEQ ID NO: 34 and a light chain variable region comprising a CDR2 having the amino acid sequence of SEQ ID NO: 38; a heavy chain variable region comprising a CDR2 having the amino acid sequence of SEQ ID NO: 42 and a light chain variable region comprising a CDR2 having the amino acid sequence of SEQ ID NO: 38; a heavy chain variable region comprising a CDR2 having the amino acid sequence of SEQ ID NO: 34 and a light chain variable region comprising a CDR2 having the amino acid sequence of SEQ ID NO: 49; a heavy chain variable region comprising a CDR2 having the amino acid sequence of SEQ ID NO: 53 and a light chain variable region comprising a CDR2 having the amino acid sequence of SEQ ID NO: 57; a heavy chain variable region comprising a CDR2 having the amino acid sequence of SEQ ID NO: 61 and a light chain variable region comprising a CDR2 having the amino acid sequence of SEQ ID NO: 65; a heavy chain variable region comprising a CDR2 having the amino acid sequence of SEQ ID NO: 69 and a light chain variable region comprising a CDR2 having the amino acid sequence of SEQ ID NO: 65; a heavy chain variable region comprising a CDR2 having the amino acid sequence of SEQ ID NO: 75 and a light chain variable region comprising a CDR2 having the amino acid sequence of SEQ ID NO: 49; a heavy chain variable region comprising a CDR2 having the amino acid sequence of SEQ ID NO: 75 and a light chain variable region comprising a CDR2 having the amino acid sequence of SEQ ID NO: 49; a heavy chain variable region comprising a CDR2 having the amino acid sequence of SEQ ID NO: 86 and a light chain variable region comprising a CDR2 having the amino acid sequence of SEQ ID NO: 38; a heavy chain variable region comprising a CDR2 having the amino acid sequence of SEQ ID NO: 92 and a light chain variable region comprising a CDR2 having the amino acid sequence of SEQ ID NO: 38; a heavy chain variable region comprising a CDR2 having the amino acid sequence of SEQ ID NO: 98 and a light chain variable region comprising a CDR2 having the amino acid sequence of SEQ ID NO: 102; a heavy chain variable region comprising a CDR2 having the amino acid sequence of SEQ ID NO: 106 and a light chain variable region comprising a CDR2 having the amino acid sequence of SEQ ID NO: 38; a heavy chain variable region comprising a CDR2 having the amino acid sequence of SEQ ID NO: 111 and a light chain variable region comprising a CDR2 having the amino acid sequence of SEQ ID NO: 57; a heavy chain variable region comprising a CDR2 having the amino acid sequence of SEQ ID NO: 69 and a light chain variable region comprising a CDR2 having the amino acid sequence of SEQ ID NO: 118; a heavy chain variable region comprising a CDR2 having the amino acid sequence of SEQ ID NO: 235 and a light chain variable region comprising a CDR2 having the amino acid sequence of SEQ ID NO: 38; or a heavy chain variable region comprising a CDR2 having the amino acid sequence of SEQ ID NO: 241 and a light chain variable region comprising a CDR2 having the amino acid sequence of SEQ ID NO: 38.

In some embodiments, the antibodies, or antigen binding portions thereof, comprise a heavy chain variable region comprising a CDR3 and CDR2 as described herein and a light chain variable region comprising a CDR3 and CDR2 as described herein, and further comprise a heavy chain variable region comprising a CDR1 having the amino acid sequence of SEQ ID NO: 2 and a light chain variable region comprising a CDR1 having the amino acid sequence of SEQ ID NO: 6; a heavy chain variable region comprising a CDR1 having the amino acid sequence of SEQ ID NO: 10 and a light chain variable region comprising a CDR1 having the amino acid sequence of SEQ ID NO: 14;a heavy chain variable region comprising a CDR1 having the amino acid sequence of SEQ ID NO: 18 and a light chain variable region comprising a CDR1 having the amino acid sequence of SEQ ID NO: 22; a heavy chain variable region comprising a CDR1 having the amino acid sequence of SEQ ID NO: 26 and a light chain variable region comprising a CDR1 having the amino acid sequence of SEQ ID NO: 30; a heavy chain variable region comprising a CDR1 having the amino acid sequence of SEQ ID NO: 33 and a light chain variable region comprising a CDR1 having the amino acid sequence of SEQ ID NO: 37; a heavy chain variable region comprising a CDR1 having the amino acid sequence of SEQ ID NO: 41 and a light chain variable region comprising a CDR1 having the amino acid sequence of SEQ ID NO: 45; a heavy chain variable region comprising a CDR1 having the amino acid sequence of SEQ ID NO: 33 and a light chain variable region comprising a CDR1 having the amino acid sequence of SEQ ID NO: 48; a heavy chain variable region comprising a CDR1 having the amino acid sequence of SEQ ID NO: 52 and a light chain variable region comprising a CDR1 having the amino acid sequence of SEQ ID NO: 56; a heavy chain variable region comprising a CDR1 having the amino acid sequence of SEQ ID NO: 60 and a light chain variable region comprising a CDR1 having the amino acid sequence of SEQ ID NO: 64; a heavy chain variable region comprising a CDR1 having the amino acid sequence of SEQ ID NO: 68 and a light chain variable region comprising a CDR1 having the amino acid sequence of SEQ ID NO: 64; a heavy chain variable region comprising a CDR1 having the amino acid sequence of SEQ ID NO: 74 and a light chain variable region comprising a CDR1 having the amino acid sequence of SEQ ID NO: 48; a heavy chain variable region comprising a CDR1 having the amino acid sequence of SEQ ID NO: 80 and a light chain variable region comprising a CDR1 having the amino acid sequence of SEQ ID NO: 48; a heavy chain variable region comprising a CDR1 having the amino acid sequence of SEQ ID NO: 85 and a light chain variable region comprising a CDR1 having the amino acid sequence of SEQ ID NO: 37; a heavy chain variable region comprising a CDR1 having the amino acid sequence of SEQ ID NO: 91 and a light chain variable region comprising a CDR1 having the amino acid sequence of SEQ ID NO: 37; a heavy chain variable region comprising a CDR1 having the amino acid sequence of SEQ ID NO: 97 and a light chain variable region comprising a CDR1 having the amino acid sequence of SEQ ID NO: 101; a heavy chain variable region comprising a CDR1 having the amino acid sequence of SEQ ID NO: 105 and a light chain variable region comprising a CDR1 having the amino acid sequence of SEQ ID NO: 37; a heavy chain variable region comprising a CDR1 having the amino acid sequence of SEQ ID NO: 110 and a light chain variable region comprising a CDR1 having the amino acid sequence of SEQ ID NO: 114; a heavy chain variable region comprising a CDR1 having the amino acid sequence of SEQ ID NO: 68 and a light chain variable region comprising a CDR1 having the amino acid sequence of SEQ ID NO: 117; a heavy chain variable region comprising a CDR1 having the amino acid sequence of SEQ ID NO: 234 and a light chain variable region comprising a CDR1 having the amino acid sequence of SEQ ID NO: 37; or a heavy chain variable region comprising a CDR1 having the amino acid sequence of SEQ ID NO: 240 and a light chain variable region comprising a CDR1 having the amino acid sequence of SEQ ID NO: 244.

In some embodiments, the antibodies, or antigen binding portions thereof, comprise a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In some embodiments, the antibodies, or antigen binding portions thereof, comprise a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In some embodiments, the antibodies, or antigen binding portions thereof, comprise a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In some embodiments, the antibodies, or antigen binding portions thereof, comprise a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 15, and a CDR1 domain comprising the amino acid sequence of SEQ ID NO: 30.

In some embodiments, the antibodies, or antigen binding portions thereof, comprise a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In some embodiments, the antibodies, or antigen binding portions thereof, comprise a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 46, a CDR2 domain comprising the amino acid sequence of SEQ ID NO: 38, and a CDR1 domain comprising the amino acid sequence of SEQ ID NO: 45.

In some embodiments, the antibodies, or antigen binding portions thereof, comprise a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48.

In some embodiments, the antibodies, or antigen binding portions thereof, comprise a heavy chain variable region comprising a CDR3 domain comprising the amino acid sequence of SEQ ID NO: 54, a CDR2 domain comprising the amino acid sequence of SEQ ID NO: 53, and a CDR1 domain comprising the amino acid sequence of SEQ ID NO: 52, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 56.

In some embodiments, the antibodies, or antigen binding portions thereof, comprise a heavy chain variable region comprising a CDR3 domain comprising the amino acid sequence of SEQ ID NO: 62, a CDR2 domain comprising the amino acid sequence of SEQ ID NO: 61, and a CDR1 domain comprising the amino acid sequence of SEQ ID NO: 60, and a light chain variable region comprising a CDR3 domain comprising the amino acid sequence of SEQ ID NO: 66, a CDR2 domain comprising the amino acid sequence of SEQ ID NO: 65, and a CDR1 domain comprising the amino acid sequence of SEQ ID NO: 64.

In some embodiments, the antibodies, or antigen binding portions thereof, comprise a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 72, a CDR2 domain comprising the amino acid sequence of SEQ ID NO: 65, and a CDR1 domain comprising the amino acid sequence of SEQ ID NO: 64.

In some embodiments, the antibodies, or antigen binding portions thereof, comprise a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 78, a CDR2 domain comprising the amino acid sequence of SEQ ID NO: 49, and a CDR1 domain comprising the amino acid sequence of SEQ ID NO: 48.

In some embodiments, the antibodies, or antigen binding portions thereof, comprise a heavy chain variable region comprising a CDR3 domain comprising the amino acid sequence of SEQ ID NO: 81, a CDR2 domain comprising the amino acid sequence of SEQ ID NO: 75, and a CDR1 domain comprising the amino acid sequence of SEQ ID NO: 80, and a light chain variable region comprising a CDR3 domain comprising the amino acid sequence of SEQ ID NO: 83, a CDR2 domain comprising the amino acid sequence of SEQ ID NO: 49, and a CDR1 domain comprising the amino acid sequence of SEQ ID NO: 48.

In some embodiments, the antibodies, or antigen binding portions thereof, comprise a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37.

In some embodiments, the antibodies, or antigen binding portions thereof, comprise a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 95, a CDR2 domain comprising the amino acid sequence of SEQ ID NO: 38, and a CDR1 domain comprising the amino acid sequence of SEQ ID NO: 37.

In some embodiments, the antibodies, or antigen binding portions thereof, comprise a heavy chain variable region comprising a CDR3 domain comprising the amino acid sequence of SEQ ID NO: 99, a CDR2 domain comprising the amino acid sequence of SEQ ID NO: 98, and a CDR1 domain comprising the amino acid sequence of SEQ ID NO: 97, and a light chain variable region comprising a CDR3 domain comprising the amino acid sequence of SEQ ID NO: 103, a CDR2 domain comprising the amino acid sequence of SEQ ID NO: 102, and a CDR1 domain comprising the amino acid sequence of SEQ ID NO: 101.

In some embodiments, the antibodies, or antigen binding portions thereof, comprise a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37.

In some embodiments, the antibodies, or antigen binding portions thereof, comprise a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 114.

In some embodiments, the antibodies, or antigen binding portions thereof, comprise a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 119, a CDR2 domain comprising the amino acid sequence of SEQ ID NO: 118, and a CDR1 domain comprising the amino acid sequence of SEQ ID NO: 117.

In some embodiments, the antibodies, or antigen binding portions thereof, comprise a heavy chain variable region comprising a CDR3 domain comprising the amino acid sequence of SEQ ID NO: 236, a CDR2 domain comprising the amino acid sequence of SEQ ID NO: 235, and a CDR1 domain comprising the amino acid sequence of SEQ ID NO: 234, and a light chain variable region comprising a CDR3 domain comprising the amino acid sequence of SEQ ID NO: 238, a CDR2 domain comprising the amino acid sequence of SEQ ID NO: 38, and a CDR1 domain comprising the amino acid sequence of SEQ ID NO: 37.

In some embodiments, the antibodies, or antigen binding portions thereof, comprise a heavy chain variable region comprising a CDR3 domain comprising the amino acid sequence of SEQ ID NO: 242, a CDR2 domain comprising the amino acid sequence of SEQ ID NO: 241, and a CDR1 domain comprising the amino acid sequence of SEQ ID NO: 240, and a light chain variable region comprising a CDR3 domain comprising the amino acid sequence of SEQ ID NO: 245, a CDR2 domain comprising the amino acid sequence of SEQ ID NO: 38, and a CDR1 domain comprising the amino acid sequence of SEQ ID NO: 244.

In some embodiments, the antibodies, or antigen binding portions thereof, comprise a heavy chain variable region comprising the amino acid sequence of SEQ ID NO: 1 and a light chain variable region comprising the amino acid sequence of SEQ ID NO: 5.

In some embodiments, the antibodies, or antigen binding portions thereof, comprise a heavy chain variable region comprising the amino acid sequence of SEQ ID NO: 9 and a light chain variable region comprising the amino acid sequence of SEQ ID NO: 13.

In some embodiments, the antibodies, or antigen binding portions thereof, comprise a heavy chain variable region comprising the amino acid sequence of SEQ ID NO: 17 and a light chain variable region comprising the amino acid sequence of SEQ ID NO: 21.

In some embodiments, the antibodies, or antigen binding portions thereof, comprise a heavy chain variable region comprising the amino acid sequence of SEQ ID NO: 25 and a light chain variable region comprising the amino acid sequence of SEQ ID NO: 29.

In some embodiments, the antibodies, or antigen binding portions thereof, comprisea heavy chain variable region comprising the amino acid sequence of SEQ ID NO: 32 and a light chain variable region comprising the amino acid sequence of SEQ ID NO: 36.

In some embodiments, the antibodies, or antigen binding portions thereof, comprisea heavy chain variable region comprising the amino acid sequence of SEQ ID NO: 40 and a light chain variable region comprising the amino acid sequence of SEQ ID NO: 44.

In some embodiments, the antibodies, or antigen binding portions thereof, comprise a heavy chain variable region comprising the amino acid sequence of SEQ ID NO: 32 and a light chain variable region comprising the amino acid sequence of SEQ ID NO: 47.

In some embodiments, the antibodies, or antigen binding portions thereof, comprisea heavy chain variable region comprising the amino acid sequence of SEQ ID NO: 51 and a light chain variable region comprising the amino acid sequence of SEQ ID NO: 55.

In some embodiments, the antibodies, or antigen binding portions thereof, comprise a heavy chain variable region comprising the amino acid sequence of SEQ ID NO: 59 and a light chain variable region comprising the amino acid sequence of SEQ ID NO: 63.

In some embodiments, the antibodies, or antigen binding portions thereof, comprisea heavy chain variable region comprising the amino acid sequence of SEQ ID NO: 67 and a light chain variable region comprising the amino acid sequence of SEQ ID NO: 71.

In some embodiments, the antibodies, or antigen binding portions thereof, comprisea heavy chain variable region comprising the amino acid sequence of SEQ ID NO: 73 and a light chain variable region comprising the amino acid sequence of SEQ ID NO: 77.

In some embodiments, the antibodies, or antigen binding portions thereof, comprisea heavy chain variable region comprising the amino acid sequence of SEQ ID NO: 79 and a light chain variable region comprising the amino acid sequence of SEQ ID NO: 82.

In some embodiments, the antibodies, or antigen binding portions thereof, comprisea heavy chain variable region comprising the amino acid sequence of SEQ ID NO: 84 and a light chain variable region comprising the amino acid sequence of SEQ ID NO: 88.

In some embodiments, the antibodies, or antigen binding portions thereof, comprisea heavy chain variable region comprising the amino acid sequence of SEQ ID NO: 90 and a light chain variable region comprising the amino acid sequence of SEQ ID NO: 94.

In some embodiments, the antibodies, or antigen binding portions thereof, comprisea heavy chain variable region comprising the amino acid sequence of SEQ ID NO: 96 and a light chain variable region comprising the amino acid sequence of SEQ ID NO: 100.

In some embodiments, the antibodies, or antigen binding portions thereof, comprise a heavy chain variable region comprising the amino acid sequence of SEQ ID NO: 104 and a light chain variable region comprising the amino acid sequence of SEQ ID NO: 108.

In some embodiments, the antibodies, or antigen binding portions thereof, comprisea heavy chain variable region comprising the amino acid sequence of SEQ ID NO: 109 and a light chain variable region comprising the amino acid sequence of SEQ ID NO: 113.

In some embodiments, the antibodies, or antigen binding portions thereof, comprisea heavy chain variable region comprising the amino acid sequence of SEQ ID NO: 115 and a light chain variable region comprising the amino acid sequence of SEQ ID NO: 116.

In some embodiments, the antibodies, or antigen binding portions thereof, comprise a heavy chain variable region comprising the amino acid sequence of SEQ ID NO: 233 and a light chain variable region comprising the amino acid sequence of SEQ ID NO: 237.

In some embodiments, the antibodies, or antigen binding portions thereof, comprise a heavy chain variable region comprising the amino acid sequence of SEQ ID NO: 239 and a light chain variable region comprising the amino acid sequence of SEQ ID NO: 243.

In some embodiments, the disclosure provides an antibody, or antigen-binding portion thereof, that binds to the same epitope as an antibody, or antigen-binding portion thereof, like those described herein.

In other embodiments, the antibody, or antigen-binding portion thereof, does not bind to SEZ6 or SEZ6L.

In one embodiment, the antibody, or antigen-binding portion thereof, is a bispecific antibody or a multispecific antibody.

The disclosure also provides, in certain embodiments, isolated nucleic acids encoding the antibodies, or antigen binding portions thereof of the disclosure.

In some embodiments of the disclosure, the antibodies, or antigen binding portions thereof, comprise a heavy chain immunoglobulin constant domain selected from the group consisting of a human IgG constant domain, a human IgM constant domain, a human IgE constant domain, and a human IgA constant domain. In some embodiments, the IgG constant domain is selected from the group consisting of an IgG1 constant domain, an IgG2 constant domain, an IgG3 constant domain, and an IgG4 constant domain. In other embodiments, the antibody is a multispecific antibody.

In other embodiments of the disclosure, the antibodies, or antigen binding portions thereof, comprise a Fab, a Fab', a F(ab')2, a Fv, a disulfide linked Fv, an scFv, a single domain antibody, and a diabody.

In other embodiments the disclosure provides a pharmaceutical composition comprising the antibody, or antigen binding portion thereof, as described herein, and a pharmaceutically acceptable carrier.

In other embodiments the disclosure provides an antibody, or antigen binding portion thereof, as described herein, conjugated to at least one drug.

In some embodiments, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In one embodiment, the anti-tumor antibiotic is pyrrolobenzodiazepine (PBD).

In other embodiments, the at least one drug is selected from the group consisting of an auristatin, a maytansinoid, and a DNA alkylating agent. In one embodiment, the auristatin is monomethyauristatin E (MMAE). In another embodiment, the maytansinoid is 4-methyl-4-mercapto-1-oxopentyl)-maytansine (DM4). In another embodiment, the DNA alkylating agent is an indolino-benzodiazepine (IGN). In one embodiment, the at least one drug is pyrrolobenzodiazepine (PBD).

In some embodiments, the at least one drug is conjugated to the antibody, or antigen-binding portion thereof, via a linker, e.g., a cleavable linker or a non-cleavable linker.

In some embodiments, the auristatin is monomethyauristatin E (MMAE) and the linker is maleimido-caproyl-valine-citrulline (MC-VC). In some embodiments, the maytansinoid is 4-methyl-4-mercapto-1-oxopentyl)-maytansine (DM4) and the linker is D-Ala-L-dpa or sSPDB. In some embodiments, the DNA alkylating agent is an indolino-benzodiazepine (IGN) and the linker is D-Ala-L-dpa.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 15, and a CDR1 domain comprising the amino acid sequence of SEQ ID NO: 30.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 46, a CDR2 domain comprising the amino acid sequence of SEQ ID NO: 38, and a CDR1 domain comprising the amino acid sequence of SEQ ID NO: 45.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 54, a CDR2 domain comprising the amino acid sequence of SEQ ID NO: 53, and a CDR1 domain comprising the amino acid sequence of SEQ ID NO: 52, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 56.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 62, a CDR2 domain comprising the amino acid sequence of SEQ ID NO: 61, and a CDR1 domain comprising the amino acid sequence of SEQ ID NO:60, and a light chain variable region comprising a CDR3 domain comprising the amino acid sequence of SEQ ID NO: 66, a CDR2 domain comprising the amino acid sequence of SEQ ID NO: 65, and a CDR1 domain comprising the amino acid sequence of SEQ ID NO: 64.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 72, a CDR2 domain comprising the amino acid sequence of SEQ ID NO: 65, and a CDR1 domain comprising the amino acid sequence of SEQ ID NO: 64.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 78, a CDR2 domain comprising the amino acid sequence of SEQ ID NO: 49, and a CDR1 domain comprising the amino acid sequence of SEQ ID NO: 48.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 81, a CDR2 domain comprising the amino acid sequence of SEQ ID NO: 75, and a CDR1 domain comprising the amino acid sequence of SEQ ID NO: 80, and a light chain variable region comprising a CDR3 domain comprising the amino acid sequence of SEQ ID NO: 83, a CDR2 domain comprising the amino acid sequence of SEQ ID NO: 49, and a CDR1 domain comprising the amino acid sequence of SEQ ID NO: 48.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 95, a CDR2 domain comprising the amino acid sequence of SEQ ID NO: 38, and a CDR1 domain comprising the amino acid sequence of SEQ ID NO: 37.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 99, a CDR2 domain comprising the amino acid sequence of SEQ ID NO: 98, and a CDR1 domain comprising the amino acid sequence of SEQ ID NO: 97, and a light chain variable region comprising a CDR3 domain comprising the amino acid sequence of SEQ ID NO: 103, a CDR2 domain comprising the amino acid sequence of SEQ ID NO: 102, and a CDR1 domain comprising the amino acid sequence of SEQ ID NO: 101.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 114.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 119, a CDR2 domain comprising the amino acid sequence of SEQ ID NO: 118, and a CDR1 domain comprising the amino acid sequence of SEQ ID NO: 117.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 236, a CDR2 domain comprising the amino acid sequence of SEQ ID NO: 235, and a CDR1 domain comprising the amino acid sequence of SEQ ID NO: 234, and a light chain variable region comprising a CDR3 domain comprising the amino acid sequence of SEQ ID NO: 238, a CDR2 domain comprising the amino acid sequence of SEQ ID NO: 38, and a CDR1 domain comprising the amino acid sequence of SEQ ID NO: 37.

In other aspects, the disclosure provides an antibody drug conjugate (ADC) comprising an antibody, or antigen binding portion thereof, conjugated to at least one drug, e.g., pyrrolobenzodiazepine (PBD), auristatin, at least one maytansinoid, or at least one DNA alkylating agent, wherein the antibody, or antigen binding portion thereof, comprises a heavy chain variable region comprising a CDR3 domain comprising the amino acid sequence of SEQ ID NO: 242, a CDR2 domain comprising the amino acid sequence of SEQ ID NO: 241, and a CDR1 domain comprising the amino acid sequence of SEQ ID NO: 240, and a light chain variable region comprising a CDR3 domain comprising the amino acid sequence of SEQ ID NO: 245, a CDR2 domain comprising the amino acid sequence of SEQ ID NO: 38, and a CDR1 domain comprising the amino acid sequence of SEQ ID NO: 244.

In other embodiments, the antibody, or antigen binding portion thereof, of the ADC comprises a heavy chain variable region comprising the amino acid sequence of SEQ ID NO: 1 and a light chain variable region comprising the amino acid sequence of SEQ ID NO: 5.

In other embodiments, the antibody, or antigen binding portion thereof, of the ADC comprises a heavy chain variable region comprising the amino acid sequence of SEQ ID NO: 9 and a light chain variable region comprising the amino acid sequence of SEQ ID NO: 13.

In other embodiments, the antibody, or antigen binding portion thereof, of the ADC comprises a heavy chain variable region comprising the amino acid sequence of SEQ ID NO: 17 and a light chain variable region comprising the amino acid sequence of SEQ ID NO: 21.

In other embodiments, the antibody, or antigen binding portion thereof, of the ADC comprises a heavy chain variable region comprising the amino acid sequence of SEQ ID NO: 25 and a light chain variable region comprising the amino acid sequence of SEQ ID NO: 29.

In other embodiments, the antibody, or antigen binding portion thereof, of the ADC comprises a heavy chain variable region comprising the amino acid sequence of SEQ ID NO: 32 and a light chain variable region comprising the amino acid sequence of SEQ ID NO: 36.

In other embodiments, the antibody, or antigen binding portion thereof, of the ADC comprises a heavy chain variable region comprising the amino acid sequence of SEQ ID NO: 40 and a light chain variable region comprising the amino acid sequence of SEQ ID NO: 44.

In other embodiments, the antibody, or antigen binding portion thereof, of the ADC comprises a heavy chain variable region comprising the amino acid sequence of SEQ ID NO: 32 and a light chain variable region comprising the amino acid sequence of SEQ ID NO: 47.

In other embodiments, the antibody, or antigen binding portion thereof, of the ADC comprises a heavy chain variable region comprising the amino acid sequence of SEQ ID NO: 51 and a light chain variable region comprising the amino acid sequence of SEQ ID NO: 55.

In other embodiments, the antibody, or antigen binding portion thereof, of the ADC comprises a heavy chain variable region comprising the amino acid sequence of SEQ ID NO: 59 and a light chain variable region comprising the amino acid sequence of SEQ ID NO: 63.

In other embodiments, the antibody, or antigen binding portion thereof, of the ADC comprises a heavy chain variable region comprising the amino acid sequence of SEQ ID NO: 67 and a light chain variable region comprising the amino acid sequence of SEQ ID NO: 71.

In other embodiments, the antibody, or antigen binding portion thereof, of the ADC comprises a heavy chain variable region comprising the amino acid sequence of SEQ ID NO: 73 and a light chain variable region comprising the amino acid sequence of SEQ ID NO: 77.

In other embodiments, the antibody, or antigen binding portion thereof, of the ADC comprises a heavy chain variable region comprising the amino acid sequence of SEQ ID NO: 79 and a light chain variable region comprising the amino acid sequence of SEQ ID NO: 82.

In other embodiments, the antibody, or antigen binding portion thereof, of the ADC comprises a heavy chain variable region comprising the amino acid sequence of SEQ ID NO: 84 and a light chain variable region comprising the amino acid sequence of SEQ ID NO: 88.

In other embodiments, the antibody, or antigen binding portion thereof, of the ADC comprises a heavy chain variable region comprising the amino acid sequence of SEQ ID NO: 90 and a light chain variable region comprising the amino acid sequence of SEQ ID NO: 94.

In other embodiments, the antibody, or antigen binding portion thereof, of the ADC comprises a heavy chain variable region comprising the amino acid sequence of SEQ ID NO: 96 and a light chain variable region comprising the amino acid sequence of SEQ ID NO: 100.

In other embodiments, the antibody, or antigen binding portion thereof, of the ADC comprises a heavy chain variable region comprising the amino acid sequence of SEQ ID NO: 104 and a light chain variable region comprising the amino acid sequence of SEQ ID NO: 108.

In other embodiments, the antibody, or antigen binding portion thereof, of the ADC comprises a heavy chain variable region comprising the amino acid sequence of SEQ ID NO: 109 and a light chain variable region comprising the amino acid sequence of SEQ ID NO: 113.

In other embodiments, the antibody, or antigen binding portion thereof, of the ADC comprises a heavy chain variable region comprising the amino acid sequence of SEQ ID NO: 115 and a light chain variable region comprising the amino acid sequence of SEQ ID NO: 116.

In other embodiments, the antibody, or antigen binding portion thereof, of the ADC comprises a heavy chain variable region comprising the amino acid sequence of SEQ ID NO: 233 and a light chain variable region comprising the amino acid sequence of SEQ ID NO: 237.

In other embodiments, the antibody, or antigen binding portion thereof, of the ADC comprises a heavy chain variable region comprising the amino acid sequence of SEQ ID NO: 239 and a light chain variable region comprising the amino acid sequence of SEQ ID NO: 243.

In one embodiment, the ADC comprises an auristatin, wherein the auristatin is monomethyauristatin E (MMAE). In another embodiment, the ADC comprises a maytansinoid, wherein the maytansinoid is 4-methyl-4-mercapto-1-oxopentyl)-maytansine (DM4). In another embodiment, the ADC comprises a DNA alkylating agent, wherein the DNA alkylating agent is an indolino-benzodiazepine (IGN). In one embodiment, the ADC comprises pyrrolobenzodiazepine (PBD).

In some embodiments, the at least one drug is conjugated to the antibody, or antigen-binding portion thereof, via a linker, e.g., a cleavable linker or a non-cleavable linker.

In some embodiments, the auristatin is monomethyauristatin E (MMAE) and the linker is maleimido-caproyl-valine-citrulline (MC-VC). In some embodiments, the maytansinoid is 4-methyl-4-mercapto-1-oxopentyl)-maytansine (DM4) and the linker is D-Ala-L-dpa or sSPDB. In some embodiments, the DNA alkylating agent is an indolino-benzodiazepine (IGN) and the linker is D-Ala-L-dpa.

In one embodiment, the disclosure provides a pharmaceutical composition comprising an ADC mixture comprising a plurality of the ADC of the disclosure, and a pharmaceutically acceptable carrier.

In one embodiment, the ADC mixture has an average drug to antibody ratio (DAR) of 1-8.

In another aspect, the disclosure provides a method for treating a subject having a SEZ6L2 associated disorder, comprising administering an effective amount of an ADC comprising an anti-SEZ6L2 antibody, or antigen binding portion thereof, conjugated to at least one drug, e.g., pyrrolobenzodiazepine (PBD), maytansinoid, or at least one DNA alkylating agent, wherein the anti-SEZ6L2 antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6;

a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14;

a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22;

a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 15, and a CDR1 domain comprising the amino acid sequence of SEQ ID NO: 30;

a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37;

a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 46, a CDR2 domain comprising the amino acid sequence of SEQ ID NO: 38, and a CDR1 domain comprising the amino acid sequence of SEQ ID NO: 45;

a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48;

a heavy chain variable region comprising a CDR3 domain comprising the amino acid sequence of SEQ ID NO: 54, a CDR2 domain comprising the amino acid sequence of SEQ ID NO: 53, and a CDR1 domain comprising the amino acid sequence of SEQ ID NO: 52, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 56;

a heavy chain variable region comprising a CDR3 domain comprising the amino acid sequence of SEQ ID NO: 62, a CDR2 domain comprising the amino acid sequence of SEQ ID NO: 61, and a CDR1 domain comprising the amino acid sequence of SEQ ID NO:60, and a light chain variable region comprising a CDR3 domain comprising the amino acid sequence of SEQ ID NO: 66, a CDR2 domain comprising the amino acid sequence of SEQ ID NO: 65, and a CDR1 domain comprising the amino acid sequence of SEQ ID NO: 64;

a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 72, a CDR2 domain comprising the amino acid sequence of SEQ ID NO: 65, and a CDR1 domain comprising the amino acid sequence of SEQ ID NO: 64;

a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 78, a CDR2 domain comprising the amino acid sequence of SEQ ID NO: 49, and a CDR1 domain comprising the amino acid sequence of SEQ ID NO: 48;

a heavy chain variable region comprising a CDR3 domain comprising the amino acid sequence of SEQ ID NO: 81, a CDR2 domain comprising the amino acid sequence of SEQ ID NO: 75, and a CDR1 domain comprising the amino acid sequence of SEQ ID NO: 80, and a light chain variable region comprising a CDR3 domain comprising the amino acid sequence of SEQ ID NO: 83, a CDR2 domain comprising the amino acid sequence of SEQ ID NO: 49, and a CDR1 domain comprising the amino acid sequence of SEQ ID NO: 48;

a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37;

a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 95, a CDR2 domain comprising the amino acid sequence of SEQ ID NO: 38, and a CDR1 domain comprising the amino acid sequence of SEQ ID NO: 37;

a heavy chain variable region comprising a CDR3 domain comprising the amino acid sequence of SEQ ID NO: 99, a CDR2 domain comprising the amino acid sequence of SEQ ID NO: 98, and a CDR1 domain comprising the amino acid sequence of SEQ ID NO: 97, and a light chain variable region comprising a CDR3 domain comprising the amino acid sequence of SEQ ID NO: 103, a CDR2 domain comprising the amino acid sequence of SEQ ID NO: 102, and a CDR1 domain comprising the amino acid sequence of SEQ ID NO: 101;

a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37;

a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 114;

a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 119, a CDR2 domain comprising the amino acid sequence of SEQ ID NO: 118, and a CDR1 domain comprising the amino acid sequence of SEQ ID NO: 117;

a heavy chain variable region comprising a CDR3 domain comprising the amino acid sequence of SEQ ID NO: 236, a CDR2 domain comprising the amino acid sequence of SEQ ID NO: 235, and a CDR1 domain comprising the amino acid sequence of SEQ ID NO: 234, and a light chain variable region comprising a CDR3 domain comprising the amino acid sequence of SEQ ID NO: 238, a CDR2 domain comprising the amino acid sequence of SEQ ID NO: 38, and a CDR1 domain comprising the amino acid sequence of SEQ ID NO: 37; or a heavy chain variable region comprising a CDR3 domain comprising the amino acid sequence of SEQ ID NO: 242, a CDR2 domain comprising the amino acid sequence of SEQ ID NO: 241, and a CDR1 domain comprising the amino acid sequence of SEQ ID NO: 240, and a light chain variable region comprising a CDR3 domain comprising the amino acid sequence of SEQ ID NO: 245, a CDR2 domain comprising the amino acid sequence of SEQ ID NO: 38, and a CDR1 domain comprising the amino acid sequence of SEQ ID NO: 244.

In one embodiment, the SEZ6L2 associated disease is cancer, e.g., small cell lung cancer, prostate cancer, e.g., castrate resistant prostate cancer, and neuroendocrine tumors. In another embodiment, the cancer is characterized as having SEZ6L2 overexpression.

In another aspect, the disclosure provides a method for treating a subject having a SEZ6L2 associated disorder, comprising administering a therapeutically effective amount of an ADC of the disclosure to a subject in need thereof.

In another aspect, the disclosure provides a method for inhibiting or decreasing solid tumor growth in a subject having a solid tumor, said method comprising administering an effective amount of the ADC of the disclosure to the subject having the solid tumor, such that the solid tumor growth is inhibited or decreased.

In one embodiment, the solid tumor is a small cell lung carcinoma. In another embodiment, the solid tumor is a prostate tumor. In another embodiment, the solid tumor is a neuroendocrine tumor. In one embodiment, the solid tumor is characterized as having SEZ6L2 overexpression.

In one embodiment, the ADC is administered in combination with an additional agent or an additional therapy, e.g., radiation or a chemotherapeutic agent. In one embodiment, the additional therapy is a PARP inhibitor, e.g., olaparib, rucaparib, niraparib, or iniparib.

BRIEF DESCRIPTION OF THE DRAWINGS

FIGS. 1A-1B. Anti-SEZ6L2 antibodies demonstrate in vitro ADC efficacy in a SCLC cell line. NCI-H524 cells were treated with 10 ng/ml of anti-SEZ6L2 monoclonal antibodies alone (black bars), or in combination with mouse Fab-ZAP secondary antibody (grey bars; 0.4 ug/ml). After three days the percentage of viable cells was quantified and compared to positive control (an anti-transferrin receptor antibody (TR) (FIG. 1A) or human antibody 1A1 (FIG. 1B)) and negative control (mouse IgG (mIgG) (FIG. 1A) or non-binding antibody 3B5 (FIG. 1B)). FIG. 1A shows the results for murine antibodies 2E4, 3E2, 16H8, and 20C4; FIG. 1B shows the results for human antibodies 1A1, 3A1, 3A2, 3A3, 3A4, 3B1, 3B2, 3B3, 3B6, and humanized antibodies 2E4, 3E2, 16H8, and 20C4.

FIGS. 2A-2B. Anti-SEZ6L2 antibodies demonstrate in vivo ADC efficacy in a SCLC cell tumor model. NCI-H524 cell derived tumors were grown subcutaneously in the flanks of nude mice. When tumor volumes reached 250 mm$^3$, mice were randomly assigned to treatment groups and injected intraperitoneally with either the mouse parent clone mu16H8 conjugated to MMAE (mu16H8-MMAE), the humanized descendant of mu16H8 (16H8) conjugated to MMAE (16H8-MMAE), naked 16H8, mouse IgG control conjugated to MMAE (mIgG-MMAE), or PBS alone. Mice were given four injections of 5 mgs/kg over a period of 10 days, and mice were sacrificed when tumors reached 1200 mm$^3$ or became sick. FIG. 2A depicts the ability of conjugated SEZ6L2 antibodies to retard in vivo growth of SCLC tumors, FIG. 2B depicts the increased survival of mice treated with conjugated anti-SEZ6L2 antibodies.

FIGS. 3A-3F. SEZ6L2 ADC modulators mediate delivery of cytotoxic agents in SCLC and prostate cancer cell lines. Antibodies 3E2 and 1A1, conjugated to pyrrolobenzodiazepine (PBD), were tested for their effect on small cell lung cancer and prostate cell line cells. Results for small cell lung cancer cell lines H524 (FIG. 3A), DMS79 (FIG. 3B), H209 (FIG. 3C), and H1048 (FIG. 3D) and prostate adenocarcinoma cell lines LNCaP (FIG. 3E) and 22Rv1 (FIG. 3F) are depicted. As depicted in FIGS. 3A-3F, when cells were treated with anti-SEZ6L2 ADCs, an increased reduction in percent viable cells were observed compared to the control hIgG in several cell lines. While hIgG IgG-PBD can be cytotoxic to cells at high concentrations, the anti-SEZ6L2 ADCs tested were more potent, indicating an immunospecific response to SEZ6L2 rather than a general response to the PBD cytotoxin.

FIGS. 4A-4B. SEZ6L2 ADC modulators suppress tumor growth in vivo. FIG. 4A is a graph which demonstrates that anti-SEZ6L2 antibodies 3E2 and 3A1 conjugated to MMAE suppress NCI-H524 tumor growth in mice relative to vehicle or isotype control. FIG. 4B is a Kaplan-Meier survival curve which shows an antigen specific increase survival.

FIGS. 5A-5M. Detection of SEZ6L2 Surface Expression on Engineered HEK-293 Cells. FIGS. 5A-5L depict the results of flow cytometry to assess whether SEZ6L2 antibody modulators immunospecifically associate with human SEZ6L2, and to determine whether the same modulators cross-react with SEZ6 and SEZ6L. More particularly, antibodies disclosed herein were tested for cross reactivity to cell lines that overexpress the human homologs of SEZ6 (293-SEZ6), SEZ6L (293-SEZ6L), and SEZ6L2 (293-SEZ6L2). The graphs on the right-hand side of FIGS. 5A-5L represent 293-SEZ6L2. The graphs on the left-hand side of FIGS. 5A-5L represent 293-SEZ6L and 293-SEZ6. Results are set forth in FIGS. 5A-5L for the following antibodies: 1A1 (FIG. 5A), 106 (FIG. 5B), 3A1 (FIG. 5C), 3A2 (FIG. 5D), 3A3 (FIG. 5E), 3B1 (FIG. 5F), 3B3 (FIG. 5G), 3B6 (FIG. 5H), 2E4:4D2 (FIG. 5I), 3E2:7D4 (FIG. 5J), 16H8:A3F5 (FIG. 5K), 20C4:red (FIG. 5L). FIG. 5M represents a control containing secondary antibody alone. As demonstrated by the data set forth in FIGS. 5A-M, SEZ6L2 antibodies recognize a cell line that overexpresses SEZ6L2 but have no detectable binding with the two other family members SEZ6L and SEZ6.

As shown in FIG. 6, small cell lung cancer cell line NCI-209 cells that were treated with the PARP inhibitor olaparib alone responded in a dose dependent manner, as an increased reduction in percent viable cells were observed as the concentration of the inhibitor increased. Cells that were incubated with both the PARP inhibitor and 3E2-PBD (10 pM) showed an increased reduction in viable cells, thereby demonstrating an additive effect. In contrast, there is no measureable difference in cell death when IgG-PBD (10 pM) is combined with the inhibitor, indicating an immunospecific response to SEZ6L2 rather than a general response to the PBD cytotoxin.

DETAILED DESCRIPTION

Figure 6:
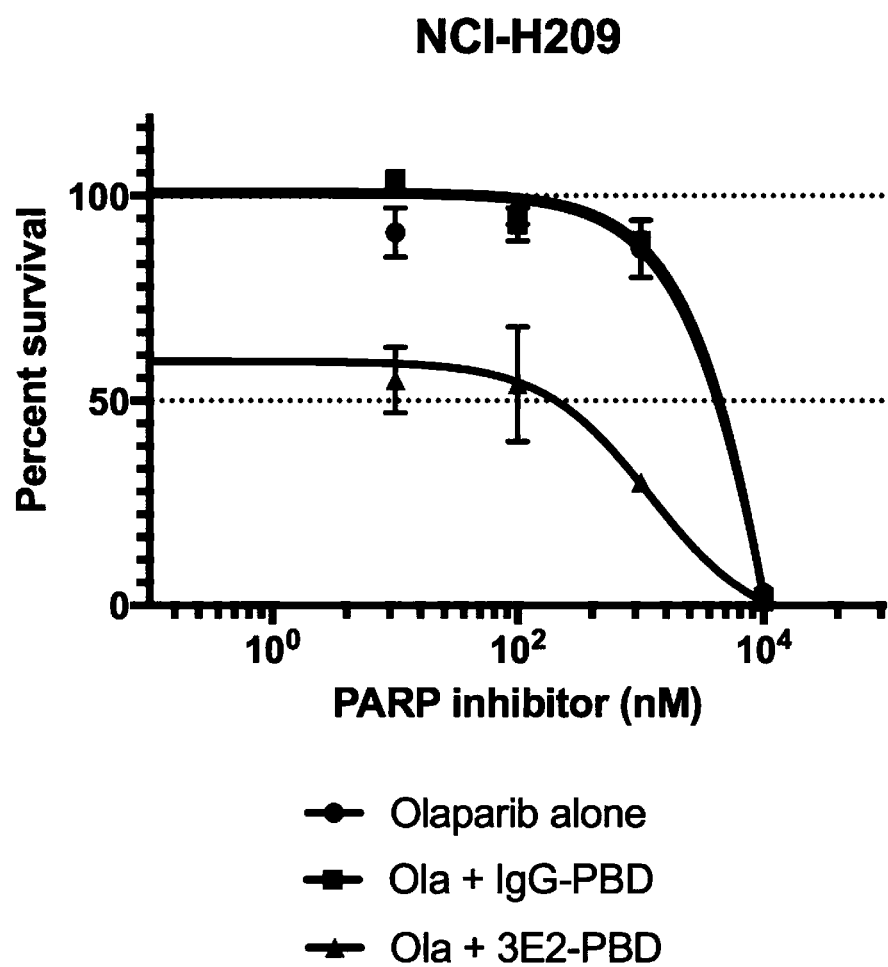
FIG. 6. SEZ6L2 ADC Combined with PARP Inhibitor Demonstrates Enhanced in vitro Efficacy. Humanized SEZ6L2 antibody 3E2 conjugated to PBD (3E2-PBD) was tested to determine whether an additional reduction in cell viability would occur when combined with a PARP inhibitor.

Various aspects of the disclosure relate to anti-SEZ6L2 antibodies and antibody fragments, anti-SEZ6L2 ADCs, and pharmaceutical compositions thereof, as well as nucleic acids, recombinant expression vectors and host cells for making such antibodies and fragments. Methods of using the antibodies and ADCs described herein to detect human SEZ6L2, to inhibit human SEZ6L2 activity (in vitro or in vivo), and to treat SEZ6L2-associated disorders, e.g., cancers, including, but not limited to, small cell lung cancer (SCLC), neuroendocrine tumors (NETs), and prostate cancer, e.g., castrate resistant prostate cancer.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "Seizure Related 6 Homolog Like 2 antibody" or "anti-SEZ6L2 antibody", used interchangeably herein, refer to an antibody that specifically binds to SEZ6L2. An antibody "which binds" an antigen of interest, i.e., SEZ6L2, is one capable of binding that antigen with sufficient affinity such that the antibody is useful in targeting a cell expressing the antigen. In a preferred embodiment, the antibody specifically binds to human SEZ6L2 (hSEZ6L2). In another preferred embodiment, the antibody does not bind to SEZ6. In another preferred embodiment, the antibody does not bind to SEZ6L. Examples of anti-SEZ6L2 antibodies are disclosed in Examples 3 and 4 below. Unless otherwise indicated, the term "anti-SEZ6L2 antibody" is meant to refer to an antibody which binds to wild type SEZ6L2, or a variant or isoform of SEZ6L2.

There are six isoforms of SEZL2, produced by alternative splicing. An exemplary amino acid sequence of wild type human SEZ6L2, which contains 910 amino acids, is provided below as SEQ ID NO: 167 (Uniprot Accession No. Q6UXD5), where the signal peptide (amino acid residues 1-27) are underlined. The mature form of wild type SEZ6L2 corresponds to the protein without the signal peptide, i.e., amino acid residues 28 to 910 of SEQ ID NO: 167.

MGTPRAQHPPPPQLLFLILLSCPWIQGLPLKEEEILPEPGSETPTVASEA

LAELLHGALLRRGPEMGYLPGSDRDPTLATPPAGQTLAVPSLPRATEPGT

GPLTTAVTPNGVRGAGPTAPELLTPPPGTTAPPPPSPASPGPPLGPEGGE

EETTTTIITTTTVTTTVTSPVLCNNNISEGEGYVESPDLGSPVSRTLGLL

DCTYSIHVYPGYGIEIQVQTLNLSQEEELLVLAGGGSPGLAPRLLANSSM

LGEGQVLRSPTNRLLLHFQSPRVPRGGGFRIHYQAYLLSCGFPPRPAHGD

VSVTDLHPGGTATFHCDSGYQLQGEETLICLNGTRPSWNGETPSCMASCG

GTIHNATLGRIVSPEPGGAVGPNLTCRWVIEAAEGRRLHLHFERVSLDED

NDRLMVRSGGSPLSPVIYDSDMDDVPERGLISDAQSLYVELLSETPANPL

LLSLRFEAFEEDRCFAPFLAHGNVTTTDPEYRPGALATFSCLPGYALEPP

GPPNAIECVDPTEPHWNDTEPACKAMCGGELSEPAGVVLSPDWPQSYSPG

QDCVWGVHVQEEKRILLQVEILNVREGDMLTLFDGDGPSARVLAQLRGPQ

PRRRLLSSGPDLTLQFQAPPGPPNPGLGQGFVLHFKEVPRNDTCPELPPP

EWGWRTASHGDLIRGTVLTYQCEPGYELLGSDILTCQWDLSWSAAPPACQ

KIMTCADPGEIANGHRTASDAGFPVGSHVQYRCLPGYSLEGAAMLTCYSR

DTGTPKWSDRVPKCALKYEPCLNPGVPENGYQTLYKHHYQAGESLRFFCY

EGFELIGEVTITCVPGHPSQWTSQPPLCKVTQTTDPSRQLEGGNLALAIL

LPLGLVIVLGSGVYIYYTKLQGKSLFGFSGSHSYSPITVESDFSNPLYEA

GDTREYEVSI

SEZ6L2 is a member of the Seizure Related Gene (SEZ) family of proteins, which includes Seizure Protein 6 Homolog (SEZ6) and Seizure 6-like Protein (SEZ6L). SEZ6L2 has approximately 41% sequence identity with SEZ6 and SEZ6L. SEZ6L2 is a type 1 transmembrane glycoprotein with an N-terminal signal peptide, five SUSHI domains (SCR repeat), three CUB (initials of the first three identified proteins containing such domains: complement factor C1r/C1s, embryonic sea urchin protein uEGF, and bone morphogenetic protein 1) domains, and a C-terminal transmembrane domain (Ishikawa et al. *Cancer Sci* 2006; 97: 737-745). The three CUB domains include amino acid residues 173-286 (CUB 1), 349-459 (CUB 2), and 527-638 (CUB 3). The five SUSHI domains include amino acid residues 288-347, 462-525, 642-701, 703-766, and 769-830, respectively.

The terms "specific binding" or "specifically binding", as used herein, in reference to the interaction of an SEZ6L2 antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, an antibody, or antigen-binding portion thereof, that is "specific" for SEZ6L2 does not bind to SEZ6. In one embodiment, an antibody, or antigen-binding portion thereof, that is "specific" for SEZ6L2 does not bind to SEZ6L. In one embodiment, an antibody, or antigen-binding portion thereof, that is "specific" for SEZ6L2 does not bind to SEZ6 or SEZ6L.

In one embodiment, the phrase "specifically binds to hSEZ6L2" or "specific binding to hSEZ6L2", as used herein, refers to the ability of an anti-SEZ6L2 antibody or ADC to interact with hSEZ6L2 with a dissociation constant ($K_D$) of 200 nM or less, 100 nM or less, 75 nM or less, 26 nM or less, 24 nM or less, 12 nM or less, 7 nM or less, 3 nM or less, 2 nM or less, 1 nM or less, 0.5 nM or less, 0.3 nM or less, 0.1 nM or less, or 0.01 nM or less. In another embodiment, the phrase "specifically binds to hSEZ6L2" or "specific binding to hSEZ6L2", as used herein, refers to the ability of an anti-SEZ6L2 antibody or ADC to interact with hSEZ6L2 with a dissociation constant ($K_D$) of between about 1 pM (0.001 nM) to 50 nM, between about 500 pM (0.5 nM) to 20 nM, between about 1 nM to 10 nM, or between about 1 nM to 5 nM. In one embodiment, $K_D$ is determined by surface plasmon resonance. In another embodiment, $K_D$ is determined as described in Example 4, herein.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 Immunoglobulin molecules can be of any type (e.g., IgG, IgE, IgM, IgD, IgA and IgY) and class (e.g., IgG1, IgG2, IgG 3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hIL-13). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain Exemplary human IgG heavy chain and light chain constant domain amino acid sequences are known in the art and represented below.

Sequence of human IgG heavy chain constant domain and light chain constant domains

| Protein | Sequence Identifier | Sequence 123456789012345678901234567890123456789012 |
|---|---|---|
| Ig gamma-1 constant region | SEQ ID NO: 168 | ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK |

-continued

| Protein | Sequence Identifier | Sequence<br>123456789012345678901234567890123 |
|---|---|---|
| | | EYKCKVSNKALPAPIEKTISKAKGQPREPQVYTLPPSREE<br>MTKNQVSLTCLVKGFYPSDIAVEWESNGQPENNYKTTPPV<br>LDSDGSFFLYSKLTVDKSRWQQGNVFSCSVMHEALHNHYT<br>QKSLSLSPGK |
| Ig gamma-1 constant region mutant | SEQ ID NO: 169 | ASTKGPSVFPLAPSSKSTSGGTAALGCLVKDYFPEPVTVS<br>WNSGALTSGVHTFPAVLQSSGLYSLSSVVTVPSSSLGTQT<br>YICNVNHKPSNTKVDKKVEPKSCDKTHTCPPCPAPEAAGG<br>PSVFLFPPKPKDTLMISRTPEVTCVVVDVSHEDPEVKFNW<br>YVDGVEVHNAKTKPREEQYNSTYRVVSVLTVLHQDWLNGK<br>EYKCKVSNKALPAPIEKTISKAKGQPREPQVYTLPPSREE<br>MTKNQVSLTCLVKGFYPSDIAVEWESNGQPENNYKTTPPV<br>LDSDGSFFLYSKLTVDKSRWQQGNVFSCSVMHEALHNHYT<br>QKSLSLSPGK |
| Ig Kappa constant region | SEQ ID NO: 170 | RTVAAPSVFIFPPSDEQLKSGTASVVCLLNNFYPREAKVQ<br>WKVDNALQSGNSQESVTEQDSKDSTYSLSSTLTLSKADYE<br>KHKVYACEVTHQGLSSPVTKSFNRGEC |
| Ig Lambda constant region | SEQ ID NO: 171 | QPKAAPSVTLFPPSSEELQANKATLVCLISDFYPGAVTVA<br>WKADSSPVKAGVETTTPSKQSNNKYAASSYLSLTPEQWKS<br>HRSYSCQVTHEGSTVEKTVAPTECS |

Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds SEZ6L2 is substantially free of antibodies that specifically bind antigens other than SEZ6L2). An isolated antibody that specifically binds SEZ6L2 may, however, have cross-reactivity to other antigens, such as SEZ6L2 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab)₂, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) Sequences of Proteins of *Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 119 and 156-166.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-SEZ6L2 DVD.

The term "activity" includes activities such as the binding specificity/affinity of an antibody or ADC for an antigen, for example, an anti-hSEZ6L2 antibody that binds to a hSEZ6L2 antigen, for example, binding to wild-type SEZ6L2 in vitro, binding to wild-type SEZ6L2 on cancer cells expressing SEZ6L2 (e.g., neuroendocrine tumor cells, lung cancer cells or prostate cancer cells), and decreasing or inhibiting tumor cellular proliferation or tumor growth.

The term "neuroendocrine tumor" or "NET," or "neuroendocrine cancer," as used herein, includes tumors comprising neuroendocrine features (genotypic or phenotypic). True or "canonical neuroendocrine tumors" arise from cells of the endocrine system and are typically highly aggressive. Neuroendocrine tumors can occur in the kidney, genitourinary tract (bladder, prostate, ovary, cervix, and endometrium), gastrointestinal tract (stomach, colon), thyroid (medullary thyroid cancer), and lung (small cell lung carcinoma and large cell neuroendocrine carcinoma). Neoplasms exhibiting neuroendocrine features are also considered NETs, and include neuroblastoma, thyroid medullary carcinoma, and carcinoid tumor. The antibodies disclosed herein may also advantageously be used to treat, prevent or diagnose pseudo neuroendocrine tumors (pNETs) that genotypically or phenotypically mimic, comprise, resemble or exhibit common traits with canonical neuroendocrine tumors. "Pseudo neuroendocrine tumors" are tumors that arise from cells of the diffuse neuroendocrine system or from cells in which a neuroendocrine differentiation cascade has been aberrantly reactivated during the oncogenic process." Such pNETs commonly share certain genotypic, phenotypic or biochemical characteristics with traditionally defined neuroendocrine tumors, including the ability to produce subsets of biologically active amines, neurotransmitters, and peptide hormones. Accordingly, the phrases "neuroendocrine tumor," "NET," "neuroendocrine cancer," "tumors comprising neuroendocrine features" or "tumors exhibiting neuroendocrine features" shall be held to comprise both neuroendocrine tumors and pseudo neuroendocrine tumors.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the disclosure have a $K_D$ of approximately $10^{-8}$ M or less, $10^{-9}$ M or less, or $10^{-10}$ M, or $10^{-11}$ M or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "anti-Seizure Related 6 Homolog Like 2 antibody drug conjugate," "anti-SEZ6L2 antibody drug conjugate," or "anti-SEZ6L2 ADC", used interchangeably herein, refer to an ADC comprising an antibody that specifically binds to SEZ6L2, whereby the antibody is conjugated to one or more chemical agent(s) or payloads. In one embodiment, the chemical agent is linked to the antibody via a linker.

In one embodiment, the anti-SEZ6L2 ADC is conjugated to a DNA alkylating agent, e.g., an indolino-benzodiazepine (IGN). In one embodiment, the DNA alkylating agent, e.g., IGN, is conjugated to the antibody via a linker, e.g., a cleavable peptide linker (D-Ala-L-dpa). In one embodiment, the anti-SEZ6L2 ADC is conjugated to a pyrrolobenzodiazepine (PBD).

In another embodiment, the anti-SEZ6L2 ADC is conjugated to a microtubule inhibitor, such as an auristatin, e.g., monomethyl auristatin E (MMAE). In another embodiment, the anti-SEZ6L2 ADC is conjugated to a microtubule inhibitor, such as a maytansinoid, e.g., DM4. In one embodiment, the auristatin (e.g, MMAE) is conjugated to the antibody via a linker, e.g., maleimido-caproyl-valine-citrulline (MC-VC). In another embodiment, the maytansinoid (e.g, DM4) is conjugated to the antibody via a linker, e.g., a cleavable peptide linker (D-Ala-L-dpa) or a charged hindered disulfide N-succinimidyl-4-(2-pyridyldithio)butanoate (sSPDB) linker.

The term "DNA alkylating agent", as used herein, refers to a family of DNA alkylating agents including indolinobenzodiazepines (IGNs) that are cytotoxic small molecules that can be used in ADCs. Examples of IGN DNA alkylating agents that can be used as a cytotoxic payload in an ADC are described in Miller et al. (2016) *Molecular Cancer Therapeutics*, vol. 15(8)). In one embodiment, an anti-SEZ6L2 antibody described herein is conjugated to an IGN to form an anti-SEZ6L2 ADC.

The term "maytansinoid," as used herein, refers to maytansine and its analogues, which are potent microtubule-targeted compounds that inhibit proliferation of cells at mitosis. Maytansinoids include DM1, DM2, DM3, and DM4, and exert their antimitotic effects through a common mechanism involving suppression of microtubule dynamic instability. (See, e.g., Emin Oroudjev et al. (2010) *Molecular Cancer Therapeutics*, Vol. 9 (10)). In one embodiment, an anti-SEZ6L2 antibody described herein is conjugated to DM4 to form an anti-SEZ6L2 ADC.

The term "auristatin", as used herein, refers to a family of antimitotic agents that function as microtubule inhibitors. Auristatin derivatives are also included within the definition of the term "auristatin". Examples of auristatins include, but are not limited to, auristatin E (AE), monomethylauristatin E (MMAE), monomethylauristatin F (MMAF), and synthetic analogs of dolastatin. In one embodiment, an anti-SEZ6L2 antibody described herein is conjugated to an auristatin, e.g., MMAE, to form an anti-SEZ6L2 ADC.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "SEZ6L2 associated disorder," as used herein, includes any disorder or disease (including proliferative disorders, e.g., cancer) that is marked, diagnosed, detected or identified by a phenotypic or genotypic aberration of SEZ6L2 genetic components or expression during the course or etiology of the disease or disorder. In this regard a SEZ6L2 phenotypic aberration or determinant may, for example, comprise increased or decreased levels of SEZ6L2 protein expression, abnormal SEZ6L2 protein expression on certain definable cell populations or abnormal SEZ6L2 protein expression at an inappropriate phase or stage of a cell lifecycle. It will be appreciated that similar expression patterns of genotypic determinants (e.g., mRNA transcription levels) of SEZ6L2 may also be used to classify or detect SEZ6L2 associated disorders. In one embodiment, an SEZ6L2 associated disorder is SCLC. In one embodiment, an SEZ6L2 associated disorder is prostate cancer, e.g., castrate resistant prostate cancer (CRPC). In another embodiment, an SEZ6L2 associated disorder is a neuroendocrine tumor.

The term "cancer" is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include neuroendocrine tumors, small cell lung cancer (SCLC), prostate cancer, e.g., castrate resistant prostate cancer (CRPC), colon cancer, colorectal cancer, head and neck cancer, breast cancer, e.g., triple negative breast cancer (TNBC), Her2 positive breast cancer, pancreatic cancer, squamous cell tumors, squamous cell carcinoma (e.g., squamous cell lung cancer or squamous cell head and neck cancer), renal cell carcinoma, medullary thyroid cancer, non-small cell lung cancer (NSCLC), e.g., squamous NSCLC, large cell NSCLC, lung carcinoid NSCLC, anal cancer, skin cancer, serous ovarian cancer, and vulvar cancer.

In one embodiment, the antibodies or ADCs are administered to a patient having a solid tumor which is likely to over-express SEZ6L2. In one embodiment, the antibodies or ADCs are administered to a patient having small cell lung cancer (SCLC). In another embodiment, the antibodies or ADCs are administered to a patient having prostate cancer, e.g., castrate resistant prostate cancer (CRPC). In still another embodiment, the antibodies or ADCs are administered to a patient having a neuroendocrine tumor. In one embodiment, the antibodies or ADCs are administered to a patient having solid tumors, including advanced solid tumors. In another embodiment, the antibodies or ADCs are administered to a patient having a SEZ6L2 expressing tumor.

The term "SEZ6L2 expressing tumor," as used herein, refers to a tumor which expresses SEZ6L2 protein. In one embodiment, SEZ6L2 expression in a tumor is determined using immunohistochemical staining of tumor cell membranes, where any immunohistochemical staining above background level in a tumor sample indicates that the tumor is an SEZ6L2 expressing tumor. Methods for detecting expression of SEZ6L2 in a tumor are known in the art. For example, *In Situ Hybridization* (ISH) analysis was used to show that SEZ6L2 is highly expressed in 66% of SCLC tumors and in 53% of prostate carcinoma samples, with low or undetectable levels in normal samples (see Example 1). In contrast, an "SEZ6L2 negative tumor" is defined as a tumor having an absence of SEZ6L2 membrane staining above background in a tumor sample as determined by immunohistochemical techniques.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 50%, 60%, 70%, 80%, 90% or more in comparison to a normal cell or comparison cell. In certain embodiments, the anti-SEZ6L2 antibodies or ADCs are used to treat solid tumors likely to overexpress SEZ6L2.

The term "administering" as used herein is meant to refer to the delivery of a substance (e.g., an anti-SEZ6L2 antibody or ADC) to achieve a therapeutic objective (e.g., the treatment of an SEZ6L2-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-SEZ6L2 antibody or ADC and an additional therapeutic agent. The additional therapeutic agent may be administered concomitant with, prior to, or following the administration of the anti-SEZ6L2 antibody or ADC.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

The term a "xenograft assay", as used herein, refers to a human tumor xenograft assay, wherein human tumor cells, such as a human small cell lung cancer tumor cells, are transplanted, either under the skin or into the organ type in which the tumor originated, into immunocompromised mice that do not reject human cells.

Various aspects of the invention are described in further detail in the following subsections.

II. Anti-SEZ6L2 Antibodies

One aspect disclosed herein provides humanized anti-SEZ6L2 antibodies, or antigen binding portions thereof. Another aspect disclosed herein provides human anti-SEZ6L2 antibodies, or antigen binding portions thereof. In one embodiment, the antibodies disclosed herein bind human SEZ6L. In another embodiment, the antibodies disclosed herein bind cynomolgus monkey SEZ6L. In another embodiment, the antibodies disclosed herein do not bind to either SEZ6 or SEZ6L. In another embodiment, the antibodies disclosed herein bind human SEZ6L expressed on tumor cells.

Another aspect disclosed herein features antibody drug conjugates (ADCs) comprising an anti-SEZ6L2 antibody described herein and at least one drug(s), such as, but not limited to, a DNA alkylating agent, e.g., an IGN, a microtubule inhibitor such as an auristatin (e.g., MMAE) or a maytansinoid (e.g., DM4), or a pyrrolobenzodiazepine (PBD). The antibodies or ADCs disclosed herein have characteristics including, but not limited to, binding to human or cynomolgus wild-type SEZ6L2 in vitro, binding to wild-type SEZ6L2 on tumor cells expressing SEZ6L2 (e.g., lung cancer or prostate cancer tumor cells, e.g., castrate resistant prostate cancer (CRPC)), and decreasing or inhibiting tumor cellular proliferation or tumor growth, e.g., lung tumor or prostate tumor growth.

In one embodiment, anti-SEZ6L2 humanized and human antibodies are disclosed which have the ability to inhibit SCLC tumor cell proliferation in vivo, as described in the Examples below. Collectively these novel antibodies are referred to herein as "SEZ6L2 antibodies." The anti-SEZ6L2 antibodies, ADCs, or antigen binding fragments thereof, are able to inhibit or decrease tumor growth in vivo, for example, in an NCI-H524 human small cell lung carcinoma (SCLC) xenograft assay in a nude mouse, as described in Example 6. In various embodiments, anti-SEZ6L2 antibodies, ADCs, or antigen binding fragments thereof, are capable of modulating a biological function of SEZ6L2. In other embodiments of the foregoing aspects, the anti-SEZ6L2 antibodies, ADCs, or antigen binding fragments thereof, bind SEZ6L2 on cells overexpressing SEZ6L2. In a further embodiment, anti-SEZ6L2 antibodies, ADCs, or antigen binding fragments thereof, do not bind to either SEZ6 or SEZ6L.

Thus, the disclosure includes anti-SEZ6L2 antibodies, ADCs, or antigen binding fragments thereof, that are effective at inhibiting or decreasing tumor growth. In one embodiment, anti-SEZ6L2 antibodies, ADCs, or antigen binding fragments thereof, do not bind to either SEZ6 or SEZ6L.

The anti-SEZ6L2 antibodies, ADCs, or antigen binding fragments thereof, are able, in one embodiment, to inhibit or decrease tumor growth in an in vivo xenograft mouse model, e.g., in an NCI-H524 human small cell lung carcinoma (SCLC) xenograft assay in a nude mouse. For example, the antibodies, or antigen binding portions thereof, are able to inhibit tumor growth by at least about 50% in an in vivo human small-cell lung carcinoma (SCLC) xenograft assay relative to a human IgG antibody which is not specific for SEZ6L2. In certain embodiments, the anti-SEZ6L2 antibodies, ADCs, or antigen binding fragments thereof, are able to inhibit or decrease tumor growth in an in vivo human small-cell lung carcinoma (SCLC) xenograft assay relative to a human IgG antibody which is not specific for SEZ6L2 by at least about 55%, at least about 60%, at least about 65%, at least about 70%, at least about 75%, or at least about 80%, when administered at the same dose and dosing periodicity. In certain embodiments, anti-SEZ6L2 antibodies, ADCs, or antigen binding fragments thereof, are able to inhibit or decrease tumor growth in an in vivo human small-cell lung carcinoma (SCLC) xenograft assay relative to a human IgG antibody which is not specific for SEZ6L2 from about 80% to about 90%, or from about 84% to about 90%, or from about 88% to about 90%, when administered at the same dose and dosing periodicity. In some embodiments, anti-SEZ6L2 antibodies, ADCs, or antigen binding fragments thereof, are able to inhibit or decrease tumor growth in an in vivo human small-cell lung carcinoma (SCLC) xenograft assay relative to a human IgG antibody which is not specific for SEZ6L2 for more than 7 days, more than 14 days, more than 1 month, more than 2 months, more than 3 months, more than 4 months, more than 5 months, more than 6 months, or more than 1 year, or for more than 30, 40, 50, 60, 70, 80, 90, 100, or 110 days when administered at the same dose and dosing periodicity.

Antibodies having combinations of any of the aforementioned characteristics are contemplated as aspects of the disclosure. ADCs, described in more detail below, may also have any of the foregoing characteristics.

One aspect of the disclosure features an anti-human SEZ6L2 (anti-hSEZ6L2) Antibody Drug Conjgate (ADC) comprising an anti-hSEZ6L2 antibody conjugated to a drug via a linker. Exemplary anti-SEZ6L2 antibodies (and sequences thereof) that can be used in the ADCs are described herein.

The anti-SEZ6L2 antibodies described herein provide the ADCs with the ability to bind to SEZ6L2 such that the cytotoxic molecule attached to the antibody (e.g., a DNA alkylating agent, e.g., an IGN, a microtubule inhibitor such as an auristatin (e.g., MMAE) or a maytansinoid (e.g., DM4), may be delivered to the SEZ6L2-expressing cell, particularly a SEZ6L2 expressing cancer cell.

While the term "antibody" is used throughout, it should be noted that antibody fragments (i.e., antigen-binding portions of an anti-SEZ6L2 antibody) are also included in the disclosure and may be included in the embodiments (methods and compositions) described throughout. For example, an anti-SEZ6L2 antibody fragment may be conjugated to the drugs (e.g., DNA alkylating agent, e.g., an IGN, a microtubule inhibitor such as an auristatin (e.g., MMAE) or a maytansinoid (e.g., DM4)), as described herein. In certain embodiments, an anti-SEZ6L2 antibody binding portion is a Fab, a Fab', a F(ab')2, a Fv, a disulfide linked Fv, an scFv, a single domain antibody, or a diabody.

II.A. Humanized Antibodies

Following the production of seventeen anti-hSEZ6L2 murine antibodies as described below in Example 2, murine antibodies mu16H8, mu3E2, mu20C4, and Mu2E4 were selected for humanization (as described below in Example 3), resulting in the production of four humanized antibodies (16H8, 3E2, 20C4, and 2E4). The heavy and light chain variable region amino acid sequences for these humanized antibodies are set forth in Table 6.

Thus, in one embodiment, humanized anti-hSEZ6L2 antibodies, or antigen binding portions thereof, comprise a heavy chain variable region comprising an amino acid sequence selected from the group consisting of 1, 9, 17, and 25; and a light chain variable region comprising an amino acid sequence selected from the group consisting of 5, 13, 21, and 29.

In one embodiment, a humanized anti-hSEZ6L2 antibody, or antigen binding portion thereof, comprises an HC CDR set (CDR1, CDR2, and CDR3) selected from the group consisting of SEQ ID NOs: 2, 3, and 4; SEQ ID NOs: 10, 11, and 12; SEQ ID NOs: 18, 19, and 20; and SEQ ID NOs: 26, 27, and 28; and an LC light chain CDR set (CDR1, CDR2, and CDR3) selected from the group consisting of SEQ ID NOs: 6, 7, and 8; SEQ ID NOs: 14, 15, and 16; SEQ ID NOs: 22, 23, and 24; and SEQ ID NOs: 30, 15, and 31.

In one embodiment, an anti-SEZ6L2 antibody, or antigen binding portion thereof, is the humanized antibody 16H8. The 16H8 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-SEZ6L2 antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-SEZ6L2 antibody, or antigen binding portion thereof, which is the humanized antibody 3E2. The 3E2 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-SEZ6L2 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-SEZ6L2 antibody, or antigen binding portion thereof, which is the humanized antibody 20C4. The 20C4 antibody comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In further embodiments, the disclosure provides an antibody having a heavy chain variable region comprising the amino acid sequence of SEQ ID NO: 17 and a light chain variable region comprising the amino acid sequence of SEQ ID NO: 21.

In some embodiments, an anti-SEZ6L2 antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-SEZ6L2 antibody, or antigen binding portion thereof, which is the humanized antibody 2E4. The 2E4 antibody comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 31, a CDR2 domain comprising the amino acid sequence of SEQ ID NO: 15, and a CDR1 domain comprising the amino acid sequence of SEQ ID NO: 30. In further embodiments, the disclosure provides an antibody having a heavy chain variable region comprising the amino acid sequence of SEQ ID NO: 25 and a light chain variable region comprising the amino acid sequence of SEQ ID NO: 29.

In some embodiments, an anti-SEZ6L2 antibody, or antigen-binding portion thereof, comprises a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

II.B. Human Antibodies

Example 4 describes the production of human SEZ6L2 antibodies through inoculation with a protein composed of the extracellular portion of the human SEZ6L2 protein (SEZ6L2-his) as described in Example 2. Transgenic mice were used to generate high affinity, fully human monoclonal antibodies that bind to and/or inhibit SEZ6L2. The heavy and light chain variable region amino acid sequences for these human antibodies are set forth in Table 9.

Thus, in one embodiment, the disclosure includes human anti-hSEZ6L2 antibodies, or antigen binding portions thereof, comprising a heavy chain variable region comprising an amino acid sequence selected from the group consisting of SEQ ID NOs:32, 40, 51, 59, 67, 73, 79, 84, 90, 96, 104, 109, 115, 233, and 239; and a light chain variable region comprising an amino acid sequence selected from the group consisting of SEQ ID NOs: 36, 44, 47, 55, 63, 71, 77, 82, 88, 94, 100, 108, 113, 116, 237, and 243.

In one embodiment, the disclosure includes a human anti-hSEZ6L2 antibody, or antigen binding portion thereof, comprising an HC CDR set (CDR1, CDR2, and CDR3) selected from the group consisting of SEQ ID NOs: 33, 34, and 35; SEQ ID NOs: 41, 42, and 42; SEQ ID NOs: 52, 53, and 54; SEQ ID NOs: 60, 61, and 62; SEQ ID NOs: 68, 69, and 70; SEQ ID NOs: 74, 75, and 76; SEQ ID NOs: 80, 75, and 81; SEQ ID NOs: 85, 86, and 87; SEQ ID NOs: 91, 92, and 93; SEQ ID NOs: 97, 98, and 99; SEQ ID NOs: 105, 106, and 107; SEQ ID NOs: 110, 111, and 112; SEQ ID NOs: 234, 235, and 236; and SEQ ID NOs: 240, 241, and 242.

and an LC light chain CDR set (CDR1, CDR2, and CDR3) selected from the group consisting of SEQ ID NOs: 37, 38, and 39; SEQ ID NOs: 45, 38, and 46; SEQ ID NOs: 48, 49, and 50; SEQ ID NOs: 56, 57, and 58; SEQ ID NOs: 64, 65, and 66; SEQ ID NOs: 64, 65, and 72; SEQ ID NOs: 48, 49, and 78; SEQ ID NOs: 48, 49, and 83; SEQ ID NOs: 37, 38, and 89; SEQ ID NOs: 37, 38, and 95; SEQ ID NOs: 101, 102, and 103; SEQ ID NOs: 37, 38, and 89; SEQ ID NOs: 114, 57, and 58; SEQ ID NOs:117, 118, and 119; SEQ ID NOs: 37, 38, and 238; and SEQ ID NOs: 244, 38, and 245.

In one embodiment, the disclosure features an anti-SEZ6L2 antibody, or antigen binding portion thereof, which is the human antibody 1A1. The 1A1 antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37. In further embodiments, the disclosure provides an antibody having a heavy chain variable region comprising the amino acid sequence of SEQ ID NO: 32 and a light chain variable region comprising the amino acid sequence of SEQ ID NO: 36.

In some embodiments, an anti-SEZ6L2 antibody, or antigen-binding portion thereof, comprises a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 36, or a sequence having at least 90%, 95%, 96%, 97%, 98%, or 99% identity to SEQ ID NO: 36.

In one embodiment, the disclosure features an anti-SEZ6L2 antibody, or antigen binding portion thereof, which is the antibody 1D2. The 1D2 antibody comprises a heavy chain variable region comprising a CDR3 domain comprising the amino acid sequence of SEQ ID NO: 43, a CDR2 domain comprising the amino acid sequence of SEQ ID NO: 42, and a CDR1 domain comprising the amino acid sequence of SEQ ID NO: 41, and a light chain variable region comprising a CDR3 domain comprising the amino acid sequence of SEQ ID NO: 46, a CDR2 domain comprising the amino acid sequence of SEQ ID NO: 38, and a CDR1 domain comprising the amino acid sequence of SEQ ID NO: 45. In further embodiments, the disclosure provides an antibody having a heavy chain variable region comprising the amino acid sequence of SEQ ID NO: 40 and a light chain variable region comprising the amino acid sequence of SEQ ID NO: 44.

In some embodiments, an anti-SEZ6L2 antibody, or antigen-binding portion thereof, comprises a heavy chain comprising an amino acid sequence set forth in SEQ ID NO: 40, or a sequence having at least 90%, 95%, 96%, 97%, 98%, or 99% identity to SEQ ID NO: 40, and/or a light chain comprising an amino acid sequence set forth in SEQ ID NO: 44, or a sequence having at least 90%, 95%, 96%, 97%, 98%, or 99% identity to SEQ ID NO: 44.

In one embodiment, the disclosure features an anti-SEZ6L2 antibody, or antigen binding portion thereof, which is the human antibody 1E4. The 1E4 antibody comprises a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 50, a CDR2 domain comprising the amino acid sequence of SEQ ID NO: 49, and a CDR1 domain comprising the amino acid sequence of SEQ ID NO: 48. In further embodiments, the disclosure provides an antibody having a heavy chain variable region comprising the amino acid sequence of SEQ ID NO: 32 and a light chain variable region comprising the amino acid sequence of SEQ ID NO: 47.

In some embodiments, an anti-SEZ6L2 antibody, or antigen-binding portion thereof, comprises a heavy chain comprising an amino acid sequence set forth in SEQ ID NO: 32, or a sequence having at least 90%, 95%, 96%, 97%, 98%, or 99% identity to SEQ ID NO: 32, and/or a light chain comprising an amino acid sequence set forth in SEQ ID NO: 47, or a sequence having at least 90%, 95%, 96%, 97%, 98%, or 99% identity to SEQ ID NO: 47.

In one embodiment, the disclosure features an anti-SEZ6L2 antibody, or antigen binding portion thereof, which is the human antibody 3A1. The 3A1 antibody comprises a heavy chain variable region comprising a CDR3 domain comprising the amino acid sequence of SEQ ID NO: 54, a CDR2 domain comprising the amino acid sequence of SEQ ID NO: 53, and a CDR1 domain comprising the amino acid sequence of SEQ ID NO: 52, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 56. In further embodiments, the disclosure provides an antibody having a heavy chain variable region comprising the amino acid sequence of SEQ ID NO: 51 and a light chain variable region comprising the amino acid sequence of SEQ ID NO: 55.

In some embodiments, an anti-SEZ6L2 antibody, or antigen-binding portion thereof, comprises a heavy chain comprising an amino acid sequence set forth in SEQ ID NO: 51, or a sequence having at least 90%, 95%, 96%, 97%, 98%, or 99% identity to SEQ ID NO: 51, and/or a light chain comprising an amino acid sequence set forth in SEQ ID NO: 55, or a sequence having at least 90%, 95%, 96%, 97%, 98%, or 99% identity to SEQ ID NO: 55.

In one embodiment, the disclosure features an anti-SEZ6L2 antibody, or antigen binding portion thereof, which is the human antibody 3B1. The 3B1 antibody comprises a heavy chain variable region comprising a CDR3 domain comprising the amino acid sequence of SEQ ID NO: 62, a CDR2 domain comprising the amino acid sequence of SEQ ID NO: 61, and a CDR1 domain comprising the amino acid sequence of SEQ ID NO:60, and a light chain variable region comprising a CDR3 domain comprising the amino acid sequence of SEQ ID NO: 66, a CDR2 domain comprising the amino acid sequence of SEQ ID NO: 65, and a CDR1 domain comprising the amino acid sequence of SEQ ID NO: 64. In further embodiments, the disclosure provides an antibody having a heavy chain variable region comprising the amino acid sequence of SEQ ID NO: 59 and a light chain variable region comprising the amino acid sequence of SEQ ID NO: 63.

In some embodiments, an anti-SEZ6L2 antibody, or antigen-binding portion thereof, comprises a heavy chain comprising an amino acid sequence set forth in SEQ ID NO: 59, or a sequence having at least 90%, 95%, 96%, 97%, 98%, or 99% identity to SEQ ID NO: 59, and/or a light chain comprising an amino acid sequence set forth in SEQ ID NO: 63, or a sequence having at least 90%, 95%, 96%, 97%, 98%, or 99% identity to SEQ ID NO: 63.

In one embodiment, the disclosure features an anti-SEZ6L2 antibody, or antigen binding portion thereof, which is the human antibody 3B3. The 3B3 antibody comprises a heavy chain variable region comprising a CDR3 domain comprising the amino acid sequence of SEQ ID NO: 70, a CDR2 domain comprising the amino acid sequence of SEQ ID NO: 69, and a CDR1 domain comprising the amino acid sequence of SEQ ID NO: 68, and a light chain variable region comprising a CDR3 domain comprising the amino acid sequence of SEQ ID NO: 72, a CDR2 domain comprising the amino acid sequence of SEQ ID NO: 65, and a CDR1 domain comprising the amino acid sequence of SEQ ID NO: 64. In further embodiments, the disclosure provides an antibody having a heavy chain variable region comprising the amino acid sequence of SEQ ID NO: 67 and a light chain variable region comprising the amino acid sequence of SEQ ID NO: 71.

In some embodiments, an anti-SEZ6L2 antibody, or antigen-binding portion thereof, comprises a heavy chain comprising an amino acid sequence set forth in SEQ ID NO: 67, or a sequence having at least 90%, 95%, 96%, 97%, 98%, or 99% identity to SEQ ID NO: 67, and/or a light chain comprising an amino acid sequence set forth in SEQ ID NO: 71, or a sequence having at least 90%, 95%, 96%, 97%, 98%, or 99% identity to SEQ ID NO: 71.

In one embodiment, the disclosure features an anti-SEZ6L2 antibody, or antigen binding portion thereof, which is the human antibody 3A2. The 3A2 antibody comprises a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 78, a CDR2 domain comprising the amino acid sequence of SEQ ID NO: 49, and a CDR1 domain comprising the amino acid sequence of SEQ ID NO: 48. In further embodiments, the disclosure provides an antibody having a heavy chain variable region comprising the amino acid sequence of SEQ ID NO: 73 and a light chain variable region comprising the amino acid sequence of SEQ ID NO: 77.

In some embodiments, an anti-SEZ6L2 antibody, or antigen-binding portion thereof, comprises a heavy chain comprising an amino acid sequence set forth in SEQ ID NO: 73, or a sequence having at least 90%, 95%, 96%, 97%, 98%, or 99% identity to SEQ ID NO: 73, and/or a light chain comprising an amino acid sequence set forth in SEQ ID NO: 77, or a sequence having at least 90%, 95%, 96%, 97%, 98%, or 99% identity to SEQ ID NO: 77.

In one embodiment, the disclosure features an anti-SEZ6L2 antibody, or antigen binding portion thereof, which is the human antibody 3A3. The 3A3 antibody comprises a heavy chain variable region comprising a CDR3 domain comprising the amino acid sequence of SEQ ID NO: 81, a CDR2 domain comprising the amino acid sequence of SEQ ID NO: 75, and a CDR1 domain comprising the amino acid sequence of SEQ ID NO: 80, and a light chain variable region comprising a CDR3 domain comprising the amino acid sequence of SEQ ID NO: 83, a CDR2 domain comprising the amino acid sequence of SEQ ID NO: 49, and a CDR1 domain comprising the amino acid sequence of SEQ ID NO: 48. In further embodiments, the disclosure provides an antibody having a heavy chain variable region comprising the amino acid sequence of SEQ ID NO: 79 and a light chain variable region comprising the amino acid sequence of SEQ ID NO: 82.

In some embodiments, an anti-SEZ6L2 antibody, or antigen-binding portion thereof, comprises a heavy chain comprising an amino acid sequence set forth in SEQ ID NO: 79, or a sequence having at least 90%, 95%, 96%, 97%, 98%, or 99% identity to SEQ ID NO: 79, and/or a light chain comprising an amino acid sequence set forth in SEQ ID NO: 82, or a sequence having at least 90%, 95%, 96%, 97%, 98%, or 99% identity to SEQ ID NO: 82.

In one embodiment, the disclosure features an anti-SEZ6L2 antibody, or antigen binding portion thereof, which is the human antibody 3A4. The 3A4 antibody comprises a heavy chain variable region comprising a CDR3 domain comprising the amino acid sequence of SEQ ID NO: 87, a CDR2 domain comprising the amino acid sequence of SEQ ID NO: 86, and a CDR1 domain comprising the amino acid sequence of SEQ ID NO: 85, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37. In further embodiments, the disclosure provides an antibody having a heavy chain variable region comprising the amino acid sequence of SEQ ID NO: 84 and a light chain variable region comprising the amino acid sequence of SEQ ID NO: 88.

In some embodiments, an anti-SEZ6L2 antibody, or antigen-binding portion thereof, comprises a heavy chain comprising an amino acid sequence set forth in SEQ ID NO: 84, or a sequence having at least 90%, 95%, 96%, 97%, 98%, or 99% identity to SEQ ID NO: 84, and/or a light chain comprising an amino acid sequence set forth in SEQ ID NO: 88, or a sequence having at least 90%, 95%, 96%, 97%, 98%, or 99% identity to SEQ ID NO: 88.

In one embodiment, the disclosure features an anti-SEZ6L2 antibody, or antigen binding portion thereof, which is the human antibody 106. The 106 antibody comprises a heavy chain variable region comprising a CDR3 domain comprising the amino acid sequence of SEQ ID NO: 93, a CDR2 domain comprising the amino acid sequence of SEQ ID NO: 92, and a CDR1 domain comprising the amino acid sequence of SEQ ID NO: 91, and a light chain variable region comprising a CDR3 domain comprising the amino acid sequence of SEQ ID NO: 95, a CDR2 domain comprising the amino acid sequence of SEQ ID NO: 38, and a CDR1 domain comprising the amino acid sequence of SEQ ID NO: 37. In further embodiments, the disclosure provides an antibody having a heavy chain variable region comprising the amino acid sequence of SEQ ID NO: 90 and a light chain variable region comprising the amino acid sequence of SEQ ID NO: 94.

In some embodiments, an anti-SEZ6L2 antibody, or antigen-binding portion thereof, comprises a heavy chain comprising an amino acid sequence set forth in SEQ ID NO: 90, or a sequence having at least 90%, 95%, 96%, 97%, 98%, or 99% identity to SEQ ID NO: 90, and/or a light chain comprising an amino acid sequence set forth in SEQ ID NO: 94, or a sequence having at least 90%, 95%, 96%, 97%, 98%, or 99% identity to SEQ ID NO: 94.

In one embodiment, the disclosure features an anti-SEZ6L2 antibody, or antigen binding portion thereof, which is the human antibody 1C1. The 1C1 antibody comprises a heavy chain variable region comprising a CDR3 domain comprising the amino acid sequence of SEQ ID NO: 99, a CDR2 domain comprising the amino acid sequence of SEQ ID NO: 98, and a CDR1 domain comprising the amino acid sequence of SEQ ID NO: 97, and a light chain variable region comprising a CDR3 domain comprising the amino acid sequence of SEQ ID NO: 103, a CDR2 domain comprising the amino acid sequence of SEQ ID NO: 102, and a CDR1 domain comprising the amino acid sequence of SEQ ID NO: 101. In further embodiments, the disclosure provides an antibody having a heavy chain variable region comprising the amino acid sequence of SEQ ID NO: 96 and a light chain variable region comprising the amino acid sequence of SEQ ID NO: 100.

In some embodiments, an anti-SEZ6L2 antibody, or antigen-binding portion thereof, comprises a heavy chain comprising an amino acid sequence set forth in SEQ ID NO: 96, or a sequence having at least 90%, 95%, 96%, 97%, 98%, or 99% identity to SEQ ID NO: 96, and/or a light chain comprising an amino acid sequence set forth in SEQ ID NO: 100, or a sequence having at least 90%, 95%, 96%, 97%, 98%, or 99% identity to SEQ ID NO: 100.

In one embodiment, the disclosure features an anti-SEZ6L2 antibody, or antigen binding portion thereof, which is the human antibody 1D5. The 1D5 antibody comprises a heavy chain variable region comprising a CDR3 domain comprising the amino acid sequence of SEQ ID NO: 107, a CDR2 domain comprising the amino acid sequence of SEQ ID NO: 106, and a CDR1 domain comprising the amino acid sequence of SEQ ID NO: 105, and a light chain variable region comprising a CDR3 domain comprising the amino acid sequence of SEQ ID NO: 89, a CDR2 domain comprising the amino acid sequence of SEQ ID NO: 38, and a CDR1 domain comprising the amino acid sequence of SEQ ID NO: 37. In further embodiments, the disclosure provides an antibody having a heavy chain variable region comprising the amino acid sequence of SEQ ID NO: 104 and a light chain variable region comprising the amino acid sequence of SEQ ID NO: 108.

In some embodiments, an anti-SEZ6L2 antibody, or antigen-binding portion thereof, comprises a heavy chain comprising an amino acid sequence set forth in SEQ ID NO: 104, or a sequence having at least 90%, 95%, 96%, 97%, 98%, or 99% identity to SEQ ID NO: 104, and/or a light chain comprising an amino acid sequence set forth in SEQ ID NO: 108, or a sequence having at least 90%, 95%, 96%, 97%, 98%, or 99% identity to SEQ ID NO: 108.

In one embodiment, the disclosure features an anti-SEZ6L2 antibody, or antigen binding portion thereof, which is the human antibody 3B6. The 3B6 antibody comprises a heavy chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110, and a light chain variable region comprising a CDR3 domain comprising the amino acid sequence of SEQ ID NO: 58, a CDR2 domain comprising the amino acid sequence of SEQ ID NO: 57, and a CDR1 domain comprising the amino acid sequence of SEQ ID NO: 114. In further embodiments, the disclosure provides an antibody having a heavy chain variable region comprising the amino acid sequence of SEQ ID NO: 109 and a light chain variable region comprising the amino acid sequence of SEQ ID NO: 113.

In some embodiments, an anti-SEZ6L2 antibody, or antigen-binding portion thereof, comprises a heavy chain comprising an amino acid sequence set forth in SEQ ID NO: 109, or a sequence having at least 90%, 95%, 96%, 97%, 98%, or 99% identity to SEQ ID NO: 109, and/or a light chain comprising an amino acid sequence set forth in SEQ ID NO: 113, or a sequence having at least 90%, 95%, 96%, 97%, 98%, or 99% identity to SEQ ID NO: 113.

In one embodiment, the disclosure features an anti-SEZ6L2 antibody, or antigen binding portion thereof, which is the human antibody 3B2. The 3B2 antibody comprises a heavy chain variable region comprising a CDR3 domain comprising the amino acid sequence of SEQ ID NO: 68, a CDR2 domain comprising the amino acid sequence of SEQ ID NO: 69, and a CDR1 domain comprising the amino acid sequence of SEQ ID NO: 70, and a light chain variable region comprising a CDR3 domain comprising the amino acid sequence of SEQ ID NO: 117, a CDR2 domain comprising the amino acid sequence of SEQ ID NO: 118, and a CDR1 domain comprising the amino acid sequence of SEQ ID NO: 119. In further embodiments, the disclosure provides an antibody having a heavy chain variable region comprising the amino acid sequence of SEQ ID NO: 115 and a light chain variable region comprising the amino acid sequence of SEQ ID NO: 116.

In some embodiments, an anti-SEZ6L2 antibody, or antigen-binding portion thereof, comprises a heavy chain comprising an amino acid sequence set forth in SEQ ID NO: 115, or a sequence having at least 90%, 95%, 96%, 97%, 98%, or 99% identity to SEQ ID NO: 115, and/or a light chain comprising an amino acid sequence set forth in SEQ ID NO: 116, or a sequence having at least 90%, 95%, 96%, 97%, 98%, or 99% identity to SEQ ID NO: 116.

In one embodiment, the disclosure features an anti-SEZ6L2 antibody, or antigen binding portion thereof, which is the human antibody 2M5_10A1. The 2M5_10A1 antibody comprises a heavy chain variable region comprising a CDR3 domain comprising the amino acid sequence of SEQ ID NO: 236, a CDR2 domain comprising the amino acid sequence of SEQ ID NO: 235, and a CDR1 domain comprising the amino acid sequence of SEQ ID NO: 234, and a light chain variable region comprising a CDR3 domain comprising the amino acid sequence of SEQ ID NO: 238, a CDR2 domain comprising the amino acid sequence of SEQ ID NO: 38, and a CDR1 domain comprising the amino acid sequence of SEQ ID NO: 37. In further embodiments, the disclosure provides an antibody having a heavy chain variable region comprising the amino acid sequence of SEQ ID NO: 233 and a light chain variable region comprising the amino acid sequence of SEQ ID NO: 237.

In some embodiments, an anti-SEZ6L2 antibody, or antigen-binding portion thereof, comprises a heavy chain comprising an amino acid sequence set forth in SEQ ID NO: 233, or a sequence having at least 90%, 95%, 96%, 97%, 98%, or 99% identity to SEQ ID NO: 233, and/or a light chain comprising an amino acid sequence set forth in SEQ ID NO: 237, or a sequence having at least 90%, 95%, 96%, 97%, 98%, or 99% identity to SEQ ID NO: 237.

In one embodiment, the disclosure features an anti-SEZ6L2 antibody, or antigen binding portion thereof, which is the human antibody 2M22_10A6. The 2M22_10A6 antibody comprises a heavy chain variable region comprising a CDR3 domain comprising the amino acid sequence of SEQ ID NO: 242, a CDR2 domain comprising the amino acid sequence of SEQ ID NO: 241, and a CDR1 domain comprising the amino acid sequence of SEQ ID NO: 240, and a light chain variable region comprising a CDR3 domain comprising the amino acid sequence of SEQ ID NO: 245, a CDR2 domain comprising the amino acid sequence of SEQ ID NO: 38, and a CDR1 domain comprising the amino acid sequence of SEQ ID NO: 244. In further embodiments, the disclosure provides an antibody having a heavy chain variable region comprising the amino acid sequence of SEQ ID NO: 239 and a light chain variable region comprising the amino acid sequence of SEQ ID NO: 243.

In some embodiments, an anti-SEZ6L2 antibody, or antigen-binding portion thereof, comprises a heavy chain comprising an amino acid sequence set forth in SEQ ID NO: 239, or a sequence having at least 90%, 95%, 96%, 97%, 98%, or 99% identity to SEQ ID NO: 239, and/or a light chain comprising an amino acid sequence set forth in SEQ ID NO: 243, or a sequence having at least 90%, 95%, 96%, 97%, 98%, or 99% identity to SEQ ID NO: 243.

The foregoing anti-SEZ6L2 antibody CDR sequences establish a novel family of SEZ6L2 binding proteins, isolated in accordance with this disclosure, and comprising antigen binding polypeptides that include the CDR sequences listed in Tables 6 and 9, as well as the Sequence Summary.

To generate and to select CDRs having preferred SEZ6L2 binding and/or neutralizing activity with respect to hSEZ6L2, standard methods known in the art for generating antibodies, or antigen binding portions thereof, and assessing the SEZ6L2 binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-SEZ6L2 antibody, or antigen binding portion thereof, comprises a heavy chain immunoglobulin constant domain selected from the group consisting of a human IgG constant domain, a human IgM constant domain, a human IgE constant domain, and a human IgA constant domain In further embodiments, the antibody, or antigen binding portion thereof, has an IgG1 heavy chain constant region, an IgG2 heavy chain constant region, an IgG3 heavy chain constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-SEZ6L2 antibody binding portion is a Fab, a Fab', a F(ab')2, a Fv, a disulfide linked Fv, an scFv, a single domain antibody, or a diabody.

In certain embodiments, the anti-SEZ6L2 antibody, or antigen binding portion thereof, is a multispecific antibody, e.g. a bispecific antibody.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-SEZ6L2 antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-l-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying SEZ6L2 positive tumors. In a certain embodiment, anti-SEZ6L2 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-SEZ6L2 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-SEZ6L2 antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-SEZ6L2 antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 120-155 and 246-249 (as set forth in the Sequence Summary) are used in the production of a recombinant antibody. The method can further comprise isolating the recombinant antibody from the culture medium.

III. Anti-SEZ6L2 Antibody Drug Conjugates (ADCs)

Anti-SEZ6L2 antibodies described herein may be conjugated to a drug moiety to form an anti-SEZ6L2 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues, such as a tumor-associated antigen, e.g., SEZ6L2 expressing tumors. Thus, in certain embodiments, the disclosure provides anti-SEZ6L2 ADCs for therapeutic use, e.g., treatment of cancer (including, but not limited to lung cancer, prostate cancer and neuroendocrine tumors).

Anti-SEZ6L2 ADCs comprise an anti-SEZ6L2 antibody, i.e., an antibody that specifically binds to SEZ6L2, linked to one or more drug moieties. The specificity of the ADC is defined by the specificity of the antibody, i.e., anti-SEZ6L2. In one embodiment, an anti-SEZ6L2 antibody is linked to one or more cytotoxic drug(s) which is delivered internally to a cancer cell expressing SEZ6L2.

Examples of drugs that may be used in the anti-SEZ6L2 ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab\text{-}(L\text{-}D)_n \qquad (I)$$

wherein Ab an anti-SEZ6L2 antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing SEZ6L2; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

In one embodiment, the ADC has a formula of Ab-(L-D)$_n$, wherein Ab is an anti-SEZ6L2 antibody, L is a linker, e.g., maleimido-caproyl-valine-citrulline (MC-VC), D is a drug, e.g., an auristatin such as MMAE, and n is 2, 4, 6, or 8 (equivalent to a DAR of 2, 4, 6, or 8). In another embodiment, n is 0-8 (equivalent to a DAR of 0-8). In one embodiment, the ADC is used in the treatment of neuroendocrine tumors.

In one embodiment, the ADC has a formula of Ab-(L-D)$_n$, wherein Ab is an anti-SEZ6L2 antibody, L is a linker, e.g., a charged hindered disulfide (sSPDB) or a cleavable peptide linker (D-Ala-L-dpa), D is a drug, e.g., a maytansinoid such as DM4, and n is 2, 4, 6, or 8 (equivalent to a DAR of 2, 4, 6, or 8). In another embodiment, n is 0-8 (equivalent to a DAR of 0-8). In one embodiment, the ADC is used in the treatment of neuroendocrine tumors.

In one embodiment, the ADC has a formula of Ab-(L-D)$_n$, wherein Ab is an anti-SEZ6L2 antibody, L is a linker, e.g., a cleavable peptide linker (D-Ala-L-dpa), D is a drug, e.g., a DNA alkylating agent such as an IGN, and n is 2, 4, 6, or 8 (equivalent to a DAR of 2, 4, 6, or 8). In another embodiment, n is 0-8 (equivalent to a DAR of 0-8). In one embodiment, the ADC is used in the treatment of small cell lung cancer (SCLC).

Additional details regarding drugs (D of Formula I) and linkers (L of Formula I) that may be used in the ADCs, as well as alternative ADC structures, are described below.

A. Anti-SEZ6L2 ADCs: Exemplary Drugs for Conjugation

Anti-SEZ6L2 antibodies may be used in ADCs to target one or more drug(s) to a cell of interest, e.g., a cancer cell expressing SEZ6L2. The anti-SEZ6L2 ADCs disclosed herein provide a targeted therapy that may, for example, reduce the side effects often seen with anti-cancer therapies, as the one or more drug(s) is delivered to a specific cell.

Auristatins

Anti-SEZ6L2 antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB b). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239, 104; 6,034,065; 5,780,588; 5,665,860; 5,663,149; 5,635, 483; 5,599,902; 5,554,725; 5,530,097; 5,521,284; 5,504, 191; 5,410,024; 5,138,036; 5,076,973; 4,986,988; 4,978, 744; 4,879,278; 4,816,444; and 4,486,414, each of which is incorporated by reference herein.

In one embodiment, anti-SEZ6L2 antibodies are conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-SEZ6L2 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

The structure of MMAE is provided below.

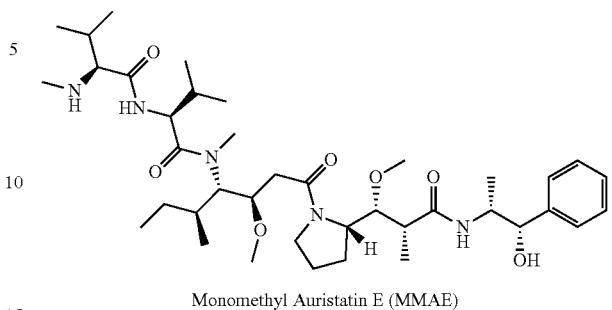

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

Maytansinoids

The anti-SEZ6L2 antibodies may be conjugated to at least one maytansinoid to form an ADC. Maytansinoids are potent antitumor agents that were originally isolated from members of the higher plant families Celastraceae, Rhamnaceae and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208, 020).

Maytansinoids to include maytansine, maytansinol, C-3 esters of maytansinol, and other maytansinol analogues and derivatives (see, e.g., U.S. Pat. Nos. 5,208,020 and 6,441, 163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate.

The structure of an exemplary maytansinoid, 4-methyl-4-mercapto-1-oxopentyl)-maytansine, (DM4), is provided below.

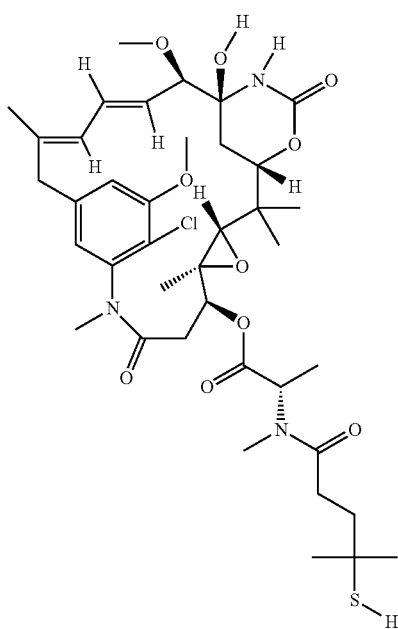 [SMILES: COc1cc2cc(c1Cl)N(C)C(=O)C[C@H](OC(=O)[C@H](C)N(C)C(=O)CCC(C)(C)S)[C@]1(C)O[C@H]1C(C)(C)[C@@H]1C[C@@](O)(NC(=O)O1)[C@H](OC)/C=C/C=C(\C)C2]

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) *Cancer Res* 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine) and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4. In one embodiment, an anti-SEZ6L2 antibody is conjugated to at least one DM1. In one embodiment, an anti-SEZ6L2 antibody is conjugated to at least one DM2. In one embodiment, an anti-SEZ6L2 antibody is conjugated to at least one DM3. In one embodiment, an anti-SEZ6L2 antibody is conjugated to at least one DM4.

DNA Alkylating Agents

The term "DNA alkylating agent", as used herein, includes a family of DNA alkylating agents including indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics*, 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

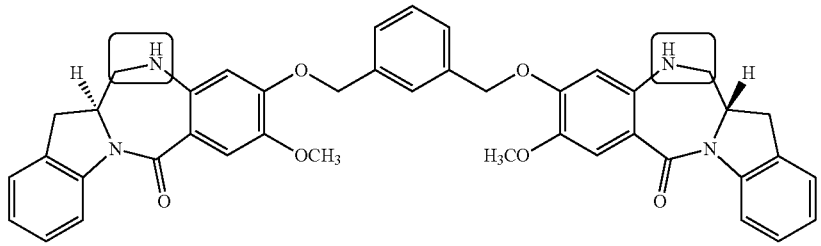

Other Drugs for Conjugation

Examples of drugs that may be used in ADCs, i.e., drugs that may be conjugated to the anti-SEZ6L2 antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-SEZ6L2 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by affecting microtubule polymerization or microtubule depolymerization. Thus, in one embodiment, an anti-SEZ6L2 antibody is conjugated to one or more mitotic inhibitor(s) that disrupts microtubule formation by inhibiting tubulin polymerization. In one embodiment, the mitotic inhibitor used in the ADCs is IXEMPRA® (ixabepilone). Examples of mitotic inhibitors that may be used in the anti-SEZ6L2 ADCs include dolastatins, e.g., dolastatin 10 and dolastatin 15, and plant alkaloids, e.g., a taxane and *vinca* alkaloid, e.g., indesine sulfate, vincristine, vinblastine and vinorelbine. Included in the genus of mitotic inhibitors are auristatins and maytansinoids, described above.

Anti-SEZ6L2 antibodies described herein may be conjugated to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfanamide derivatives described in U.S. Pat. No. 5,821,263; and TAXOL™ derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (TAXOTERE®; Sanofi Aventis), paclitaxel (ABRAXANE® or TAXOL™; Abraxis Oncology), and nanoparticle paclitaxel (ABI-007/ABRAXANE®; Abraxis Bioscience).

2. Antitumor Antibiotics

Anti-SEZ6L2 antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-SEZ6L2 ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-SEZ6L2 ADCs include bleomycin (BLENOXANE™ Bristol-Myers Squibb), mitomycin, and plicamycin (also known as mithramycin).

3. Immunomodulating Agents

In one aspect, anti-SEZ6L2 antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, *bacillus* calmette-guerin (BCG) and levamisole (ERGAMISOL™). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-SEZ6L2 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-SEZ6L2 ADCs include, recombinant bivalent human papillomavirus (HPV) vaccine types 16 and 18 vaccine (CERVARIX® GlaxoSmithKline), recombinant quadrivalent human papillomavirus (HPV) types 6, 11, 16, and 18 vaccine (GARDASIL®, Merck & Company), and sipuleucel-T (PROVENGE®, Dendreon). Thus, in one embodiment, the anti-SEZ6L2 antibody is conjugated to at least one cancer vaccine that is either an immunostimulator or is an immunosuppressant.

The anti-SEZ6L2 antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor;

integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-SEZ6L2 antibody described herein and a cytokine.

The anti-SEZ6L2 antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-SEZ6L2 ADCs include, but are not limited to erythropoietin (Epoetin), filgrastim (NEUPOGEN® (also known as granulocyte colony-stimulating factor (G-CSF); Amgen, Inc.), sargramostim (LEUKINE® (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-SEZ6L2 antibody described herein and a CSF.

4. Alkylating Agents

The anti-SEZ6L2 antibodies may be conjugated to one or more alkylating agent(s). Alkylating agents are a class of antineoplastic compounds that attaches an alkyl group to DNA. Examples of alkylating agents that may be used in the ADCs include, but are not limited to, alkyl sulfonates, ethylenimimes, methylamine derivatives, epoxides, nitrogen mustards, nitrosoureas, triazines and hydrazines.

5. Antiangiogenic Agents

In one aspect, the anti-SEZ6L2 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (ERBITUX®), ZD1839 (IRESSA®), OSI-774, Erlotinib (TARCEVA®), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291,COL-3, MM1270, SU101, SU6668, SU11248, SU5416, with paclitaxel, with gemcitabine and cisplatin, and with irinotecan and cisplatin and with radiation, tecogalan, temozolomide and PEG interferon a2b, tetrathiomolybdate, TNP-470, thalidomide, CC-5013 and with TAXOTERE®, tumstatin, 2-methoxyestradiol, VEGF trap, mTOR inhibitors (deforolimus, everolimus (AFINITOR®, Novartis Pharmaceutical Corporation), and temsirolimus (TORISEL®, Pfizer, Inc.)), tyrosine kinase inhibitors (e.g., erlotinib (TARCEVA®, Genentech, Inc.), imatinib (GLEEVEC®, Novartis Pharmaceutical Corporation), gefitinib (IRESSA®, AstraZeneca Pharmaceuticals), dasatinib (SPRYCEL®, Brystol-Myers Squibb), sunitinib (SUTENT®, Pfizer, Inc.), nilotinib (TASIGNA®, Novartis Pharmaceutical Corporation), lapatinib (TYKERB® Tykerb, GlaxoSmithKline Pharmaceuticals), sorafenib (NEXAVAR®, Bayer and Onyx), phosphoinositide 3-kinases (PI3K).

6. Antimetabolites

The anti-SEZ6L2 antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7. Boron-Containing Agents

The anti-SEZ6L2 antibody may be conjugated to at least one boron containing agent. Boron-containing agents comprise a class of cancer therapeutic compounds which interfere with cell proliferation. Representative examples of boron containing agents include, but are not limited, to borophycin and bortezomib (VELCADE®, Millenium Pharmaceuticals).

8. Chemoprotective Agents

The anti-SEZ6L2 antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (ETHYOL®, Medimmune, Inc.), which is used to reduce renal toxicity associated with cumulative doses of cisplatin, dexrazoxane (TOTECT®, Apricus Pharma; ZINECARD®), for the treatment of extravasation caused by the administration of anthracycline (TOTECT®), and for the treatment of cardiac-related complications caused by the administration of the antitumor antibiotic doxorubicin (ZINECARD®), and mesna (MES-NEX®, Bristol-Myers Squibb), which is used to prevent hemorrhagic cystitis during chemotherapy treatment with ifocfamide.

9. Photoactive Therapeutic Agents

The anti-SEZ6L2 antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-SEZ6L2 antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111 1, Sb-119, 1-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-SEZ6L2 antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-SEZ6L2 antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, CAMPTOSAR®, Pfizer, Inc.) and topotecan (HYCAMTIN®, GlaxoSmithKline Pharmaceuticals). Representative examples of DNA topoisomerase II inhibitors include, but are not limited to, amsacrine, daunorubicin, doxorubicin, epipodophyllotoxins, ellipticines, epirubicin, etoposide, razoxane, and teniposide.

13. Tyrosine Kinase Inhibitors

The anti-SEZ6L2 antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (ELOXATIN®, Sanofi Aventis), proteasome inhibitors (e.g. PS-341 [bortezomib or VELCADE®]), HDAC inhibitors (vorinostat (ZOLINZA®, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (LYSODREN®, Bristol-Myers Squibb), and tretinoin (RENOVA® Renova, Valeant Pharmaceuticals Inc.).

In one embodiment, the agent is pyrrolobenzodiazepine (PBD). In one embodiment, the agent is a PARP inhibitor, e.g., olaparib, rucaparib, niraparib, or iniparib. In one embodiment, the PARP inhibitor is olaparib. In one embodiment, the PARP inhibitor is rucaparib. In one embodiment, the PARP inhibitor is niraparib. In one embodiment, the PARP inhibitor is iniparib. In one embodiment, the agent is saporin toxin.

It should be noted that the aforementioned groups of drug moieties that may be used in the anti-SEZ6L2 ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-SEZ6L2 antibodies described herein. In one embodiment, anti-SEZ6L2 antibodies or ADCs are used with any of the foregoing agents in a combination therapy to treat cancer, where the agent is administered prior to, at the same time as, or following administration of the anti-SEZ6L2 antibody or ADC to the subject.

B. Anti-SEZ6L2 ADCs: Exemplary Linkers

An anti-SEZ6L2 ADC comprises an anti-SEZ6L2 antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components.

For example, the linker may include a spacer, which is a moiety that exteds the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, a-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

In one aspect, an anti-SEZ6L2 antibody is conjugated to an auristatin, e.g., MMAE, via a linker comprising maleimidocaproyl ("mc"), valine citrulline (val-cit or "vc"). Maleimidocaproyl acts as a linker to the anti-SEZ6L2 antibody and is not cleavable. Val-cit is a dipeptide that is an amino acid unit of the linker and allows for cleavage of the linker by a protease, specifically the protease cathepsin B. Thus, the val-cit component of the linker provides a means for releasing the auristatin from the ADC upon exposure to the intracellular environment. In one embodiment, within the linker, p-aminobenzylalcohol (PABA) acts as a spacer and is self immolative, allowing for the release of the MMAE.

In another aspect, an anti-SEZ6L2 antibody is conjugated to a maytansinoid (e.g., DM4), via a charged hindered disulfide N-succinimidyl-4-(2-pyridyldithio)butanoate (sSPDB) linker. sSPDB is a cleavable linker that allows the conjugate to be cleaved inside the target cell in the cytosol due to the reducing intracellular environment.

In another aspect, an anti-SEZ6L2 antibody is conjugated to a maytansinoid (e.g., DM4), via a cleavable peptide linker such as D-Ala-L-dpa.

In another aspect, an anti-SEZ6L2 antibody is conjugated to an IGN via a cleavable peptide linker such as D-Ala-L-dpa.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in SEZ6L2-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-SEZ6L2 ADCs described herein is a non-cleavable linker that promotes cellular internalization.

In some embodiments, the ADC has the following formula (formula I):

$$Ab\text{-}(L\text{-}D)_n \quad (I)$$

or a pharmaceutically acceptable salt or solvate thereof; wherein Ab is the antibody, e.g., anti-SEZ6L2 antibody, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing SEZ6L2; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the -D moieties are the same. In yet another embodiment, the -D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Another approach for the generation of ADCs involves the use of heterobifunctional cross-linkers which link the anti-SEZ6L2 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-SEZ6L2 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent.

Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-SEZ6L2 antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-SEZ6L2 Antibodies and Anti-SEZ6L2 ADCs

The antibodies and antibody portions (and ADCs) preferably are capable of neutralizing human SEZ6L2 activity both in vivo and in vitro. Accordingly, such antibodies and antibody portions can be used to inhibit hSEZ6L2 activity, e.g., in a cell culture containing hSEZ6L2, in human subjects or in other mammalian subjects having SEZ6L2 with which an antibody disclosed herein cross-reacts. In one embodiment, the disclosure provides a method for inhibiting hSEZ6L2 activity comprising contacting hSEZ6L2 with an antibody or antibody portion such that hSEZ6L2 activity is inhibited. For example, in a cell culture containing, or suspected of containing hSEZ6L2, an antibody or antibody portion can be added to the culture medium to inhibit hSEZ6L2 activity in the culture.

In another embodiment, disclosed herein is a method for reducing hSEZ6L2 activity in a subject, advantageously from a subject suffering from a SEZ6L2 associated disorder or a disorder in which SEZ6L2 activity is detrimental. The disclosure provides methods for reducing SEZ6L2 activity in a subject suffering from such a disease or disorder, which method comprises administering to the subject an antibody or antibody portion of the disclosure such that SEZ6L2 activity in the subject is reduced. Preferably, the SEZ6L2 is human SEZ6L2, and the subject is a human subject. Alternatively, the subject can be a mammal expressing a SEZ6L2 to which antibodies of the disclosure are capable of binding. Still further the subject can be a mammal into which SEZ6L2 has been introduced (e.g., by administration of SEZ6L2 or by expression of a SEZ6L2 transgene). Antibodies of the disclosure can be administered to a human subject for therapeutic purposes. Moreover, antibodies of the disclosure can be administered to a non-human mammal expressing a SEZ6L2 with which the antibody is capable of binding for veterinary purposes or as an animal model of human disease. Regarding the latter, such animal models may be useful for evaluating the therapeutic efficacy of antibodies of the disclosure (e.g., testing of dosages and time courses of administration).

As used herein, the term "a disorder in which SEZ6L2 activity is detrimental" is intended to include diseases and other disorders in which the presence of SEZ6L2 in a subject suffering from the disorder has been shown to be or is suspected of being either responsible for the pathophysiology of the disorder or a factor that contributes to a worsening of the disorder. Accordingly, a disorder in which SEZ6L2 activity is detrimental is a disorder in which reduction of SEZ6L2 activity is expected to alleviate the symptoms and/or progression of the disorder. Such disorders may be evidenced, for example, by an increase in the concentration of SEZ6L2 in a biological fluid of a subject suffering from the disorder (e.g., an increase in the concentration of SEZ6L2 in a tumor, serum, plasma, synovial fluid, etc. of the subject), which can be detected, for example, using an anti-SEZ6L2 antibody as described above. Non-limiting examples of disorders that can be treated with the antibodies, or antigen binding fragments thereof, include those disorders discussed below. For example, suitable disorders include, but are not limited to, a variety of cancers including, but not limited to, small cell lung cancer (SCLC), neuroendocrine tumors (NETs), and prostate cancer, e.g., castrate resistant prostate cancer (CRPC).

Other examples of cancers that may be treated using the compositions and methods disclosed herein include breast cancer, lung cancer, a glioma, pancreatic cancer, colon cancer, head and neck cancer, kidney cancer, squamous cell carcinoma (e.g., squamous lung cancer or squamous head and neck cancer), triple negative breast cancer, non-small cell lung cancer, colorectal cancer, and mesothelioma. In one embodiment, the antibodies and ADCs disclosed herein are used to treat a solid tumor, e.g., inhibit growth of or decrease size of a solid tumor, overexpressing SEZ6L2 or which is SEZ6L2 positive. In one embodiment, the antibodies and ADCs disclosed herein are used to treat SCLC (small cell lung cancer). In another embodiment, the antibodies and ADCs disclosed herein are used to treat prostate cancer. Diseases and disorders described herein may be treated by anti-SEZ6L2 antibodies or ADCs, as well as pharmaceutical compositions comprising such anti-SEZ6L2 antibodies or ADCs.

In certain embodiments, the antibodies and ADCs disclosed herein are administered to a subject in need thereof in order to treat advanced solid tumor types likely to exhibit elevated levels of SEZ6L2. Examples of such tumors include, but are not limited to, small cell lung cancer (SCLC), neuroendocrine tumors (NETs), and prostate tumors.

In certain embodiments, the disclosure includes a method for inhibiting or decreasing solid tumor growth in a subject having a solid tumor, said method comprising administering an anti-SEZ6L2 antibody or ADC described herein, to the subject having the solid tumor, such that the solid tumor growth is inhibited or decreased. In certain embodiments, the solid tumor is a small cell lung cancer (SCLC), neuroendocrine tumor (NET), or a prostate tumor. In further embodiments, the solid tumor is an SEZ6L2 overexpressing solid tumors. In certain embodiments the anti-SEZ6L2 antibodies or ADCs described herein are administered to a subject having small cell lung cancer (SCLC), neuroendocrine tumor (NET), or prostate cancer, e.g., castrate resistant prostate cancer (CRPC), alone or in combination with an additional agent or additional therapy. In one embodiment, the additional agent or therapy is radiation and/or chemotherapy. In another embodiment, the additional agent or therapy is a PARP inhibitor, e.g., olaparib, rucaparib, niraparib, or iniparib.

In certain embodiments, the disclosure includes a method for inhibiting or decreasing solid tumor growth in a subject having a solid tumor which was identified as an SEZ6L2 expressing or SEZ6L2 overexpressing tumor, said method comprising administering an anti-SEZ6L2 antibody or ADC described herein, to the subject having the solid tumor, such that the solid tumor growth is inhibited or decreased. Methods for identifying SEZ6L2 expressing tumors (e.g., SEZ6L2 overexpressing tumors) are known in the art, and include FDA-approved tests and validation assays. For example, these assays may use primers that are specific for the SEZ6L2 gene and/or cDNA and result in the amplification of the SEZ6L2 gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a SEZ6L2-associated disorder, in a subject. The method includes: administering to the subject an SEZ6L2 binding agent (particularly an antagonist), e.g., an anti-SEZ6L2 antibody or fragment thereof as described herein, in an amount sufficient to treat or prevent the SEZ6L2-associated disorder. The SEZ6L2 antagonist, e.g., the anti-SEZ6L2 antibody or fragment thereof, can be administered to the subject, alone or in combination with other therapeutic modalities as described herein.

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more SEZ6L2 antagonists, e.g., anti-SEZ6L2 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-SEZ6L2 antibodies disclosed herein are used in combination with an anti-cancer agent or an antineoplastic agent. The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

In particular embodiments, the anti-SEZ6L2 antibodies or ADCs can be administered alone or with another anti-cancer agent which acts in conjunction with or synergistically with the antibody to treat the disease associated with SEZ6L2 activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the disclosure, the anti-SEZ6L2 antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-SEZ6L2 antibodies and ADCs described herein are administered in combination with a NAMPT inhibitor for the treatment of cancer in a subject.

In particular embodiments, the anti-SEZ6L2 antibodies or ADCs described herein can be used in a combination therapy with SN-38, which is the active metabolite of the topoisomerase inhibitor irinotecan.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of SEZ6L2 in a sample in vitro (e.g., a biological sample, such as serum, plasma, tissue, biopsy). The subject method can be used to diagnose a disorder, e.g., a cancer. The method includes: (i) contacting the sample or a control sample with the anti-SEZ6L2 antibody or fragment thereof as described herein; and (ii) detecting formation of a complex between the anti-SEZ6L2 antibody or fragment thereof, and the sample or the control sample, wherein a statistically significant change in the formation of the complex in the sample relative to the control sample is indicative of the presence of SEZ6L2 in the sample.

Given their ability to bind to human SEZ6L2, the anti-human SEZ6L2 antibodies, or portions thereof, (as well as ADCs thereof) can be used to detect human SEZ6L2 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human SEZ6L2 in a biological sample comprising contacting a biological sample with an antibody, or antibody portion, and detecting either the antibody (or antibody portion) bound to human SEZ6L2 or unbound antibody (or antibody portion), to thereby detect human SEZ6L2 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Alternative to labeling the antibody, human SEZ6L2 can be assayed in biological fluids by a competition immunoassay utilizing rhSEZ6L2 standards labeled with a detectable substance and an unlabeled anti-human SEZ6L2 antibody. In this assay, the biological sample, the labeled rhSEZ6L2 standards and the anti-human SEZ6L2 antibody are combined and the amount of labeled rhSEZ6L2 standard bound to the unlabeled antibody is determined. The amount of human SEZ6L2 in the biological sample is inversely proportional to the amount of labeled rhSEZ6L2 standard bound to the anti-SEZ6L2 antibody. Similarly, human SEZ6L2 can also be assayed in biological fluids by a competition immunoassay utilizing rhSEZ6L2 standards labeled with a detectable substance and an unlabeled anti-human SEZ6L2 antibody.

In yet another aspect, this application provides a method for detecting the presence of SEZ6L2 in vivo (e.g., in vivo imaging in a subject). The subject method can be used to diagnose a disorder, e.g., a SEZ6L2-associated disorder. The method includes: (i) administering the anti-SEZ6L2 antibody or fragment thereof as described herein to a subject or a control subject under conditions that allow binding of the antibody or fragment to SEZ6L2; and (ii) detecting formation of a complex between the antibody or fragment and SEZ6L2, wherein a statistically significant change in the formation of the complex in the subject relative to the control subject is indicative of the presence of SEZ6L2.

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which SEZ6L2 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985, 320, 5,985,309, 5,934, 272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject.

The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1

SEZ6L2 Expression in Cancer Tissues

A targeted antigen discovery study was conducted on primary small cell lung cancer (SCLC) specimens, tumor adjacent tissue, and normal tissue. Specifically, 18 SCLC primary tumors were profiled by total and membrane LC-MS/MS proteomic analysis and compared to normal lung and tumor adjacent tissue. SEZ6L2 was found to be significantly upregulated in SCLC primary tumors in these studies, identifying it as a viable candidate antigen for subsequent qualification studies.

RNAseq data indicates that SEZ6L2 expression is particularly upregulated in neoplasms with neuroendocrine features such as neuroblastoma, thyroid medullary carcinoma, carcinoid tumor, large cell neuroendocrine carcinoma (lung), and small cell lung carcinoma. Western blot analysis also showed high expression levels in various cell lines derived from neuroendocrine tumors.

To further investigate SEZ6L2 tumor expression, a panel of 33 different cancer types were also evaluated by ISH using a probe against SEZ6L2. It was found that SEZ6L2 mRNA is over-expressed in tumors of the gastro-intestinal tract, neuroendocrine system, reproductive system, brain, and lung (see Table 1, below).

TABLE 1

SEZ6L2 expression in various tumors.

| Tissue and Pathology | Score: |
| --- | --- |
| Small intestine adenocarcinoma | +++ |
| Lung small cell undifferentiated carcinoma | +++ |
| Uterus clear cell carcinoma | +++ |
| Thyroid medullary carcinoma | +++ |
| Prostate adenocarcinoma | +++ |

TABLE 1-continued

SEZ6L2 expression in various tumors.

| Tissue and Pathology | Score: |
| --- | --- |
| Cerebrum glioblastoma | +++ |
| Rectum adenocarcinoma | +++ |
| Epiploon metastatic adenocarcinoma | +++ |
| Breast invasive lobular carcinoma | ++ |
| Ovary serous adenocarcinoma | ++ |
| Cerebrum malignant ependymoma | ++ |
| Stomach adenocarcinoma | ++ |
| Pancreas adenocarcinoma | ++ |

Further ISH analysis of small cell lung and prostate carcinoma-specific arrays with a probe against SEZ6L2 showed that SEZ6L2 is highly expressed in 66% and 53% (++ or +++) of small cell lung and prostate carcinoma samples, respectively, with low or undetectable levels in normal samples. See Table 2, below. The SCLC array consisted of 32 carcinomas and 5 samples of normal or adjacent normal lung, in duplicate, while the prostate tumor microarray consisted of 69 cases of prostatic adenocarcinoma, and 6 normal tissues.

TABLE 2

SEZ6L2 transcript is upregulated in SCLC and prostate microarrays.

| Tissue Type | Normal or Tumor | Negative | + | ++ | +++ |
| --- | --- | --- | --- | --- | --- |
| lung | SCLC tumor | — | 11 | 16 | 5 |
| lung | normal | 5 | — | — | — |
| prostate | tumor | 4 | 28 | 26 | 11 |
| prostate | normal | 2 | 3 | 1 | — |

Targeted proteomics found that the maximum copy number expression of SEZ6L2 in human SCLC tumors is approximately 14,000 copies per cell in human tumors, consistent with antigen density measurements based on cell line expression. SEZ6L2 has been observed as both tyrosine phosphorylated and ubiquitylated in cancer cell lines (see the PhosphoSitePlus™ website).

To determine protein expression of SEZ6L2 in patients who have undergone chemotherapy, 16 chemo-refractory SCLC specimens were obtained and SEZ6L2 expression in primary tumors vs. chemo-refractory tumors was compared. It was found that SEZ6L2 expression was similar in chemo-refractory samples as compared to primary tumors.

To compare SEZ6L2 expression in other tumor types, internally generated proteomics datasets in other indications were analyzed. It was found that SEZ6L2 is strongly over-expressed in several indications and at least moderately overexpressed in most tumor types, as shown in Table 3.

TABLE 3

SEZ6L2 expression in other tumor types as determined by proteomics analysis. Indication/Expression

| TNBC | + | Squamous NSCLC | + |
| --- | --- | --- | --- |
| Luminal A | − | Large Cell NSCLC | +++ |
| Her2 Positive | ++ | Lung Carcinoid NSCLC | +++ |
| SCLC | +++ | Serous Ovarian | ++ |
| Gastric | − | Pancreatic | +++ |

TABLE 3-continued

SEZ6L2 expression in other tumor types as
determined by proteomics analysis.
Indication/Expression

| Colon | ++ | Hepatocellular Carcinoma | − |
| Prostate | + | Renal Cell Carcinoma | + |
|  |  | Medullary Thyroid Cancer | +++ |

+++ indicates overexpression (>5 fold) in >50% of specimens profiled.
++ indicates overexpression (>5 fold) in at least 25% of specimens profiled.
+ indicates overexpression in at least 10% of specimens profiled.
− indicates the protein was not found to be overexpressed.

Example 2

Generation of Anti-SEZ6L2 Murine Antibodies

SEZ6L2 modulators in the form of murine antibodies were produced in accordance with the teachings herein through inoculation with a protein composed of the extracellular portion of the human SEZ6L2 protein (Uniprot No. Q6UXD5-1; SEQ ID NO:167) fused to six C-terminal histidine-tag repeats (SEZ6L2-his). Three strains of mice were used to generate high affinity, murine monoclonal antibody modulators that associate with and/or inhibit the action of SEZ6L2 for the prevention and/or treatment of various proliferative disorders. Specifically, SJL, NZBW and Balbc mouse strains were immunized with human recombinant SEZ6L2-his and used to produce hybridomas.

The SEZ6L2-his antigen was purified from supernatant from 293 cells expressing the SEZ6L2-his construct. 50 μgs of purified SEZ6L2-his immunogen was used for the first and second immunizations, followed by 25 μgs for the final immunization. Murine antibodies were generated by immunizing 15 mice via intraperitoneal injection with denaturing adjuvant (Freund's). In a separate approach, cDNA encoding the complete mature human SEZ6L2 protein containing a C-terminal FLAG tag was purchased from Origene (cat. #RC220064L1) and also used to immunize mice. Five mice each of strain (SJL, NZBW, and Balb/c) were immunized with 50 μgs of cDNA in five immunizations, then received a boost of 10 million 293 cells expressing the SEZ6L2 construct.

Flow cytometry was used to screen mouse sera for mouse IgG antibodies specific for human SEZ6L2. A positive signal above background was indicative of antibodies specific for SEZ6L2. Briefly, $1\times10^5$ HEK 293 cells transfected with human SEZ6L2 (positive) or $1\times10^5$ untransfected HEK 293 cells (negative control) were incubated for 1 hour on ice with 100 μls of hybridoma supernatant diluted 1:100, 1:1000, and 1:10,000 in PBS+1% BSA. Cells were washed with PBS+1% BSA then incubated with 100 μls of anti-mouse IgG Fc fragment specific secondary conjugated to Alexa 488 diluted 1:1000 in PBS+1% BSA for 30 minutes on ice. Cells were washed in PBS+1% BSA and resuspended in the same buffer with propidium iodide and analyzed by flow cytometry using a MACSquant (Miltenyi Biotec) as per manufacturer's instructions.

Sera-positive immunized mice were sacrificed. Spleens were dissected out and used as a source for antibody producing cells. A single cell suspension of splenocytes was fused with non-secreting P3x63Ag8.653 myeloma cells at a ratio of 1:1. The cells were centrifuged for 5 minutes (1,200 rpm), the media was removed, and the cells were resuspended in 50 mls of I-DMEM. The cells were centrifuged again and resuspended in 1 ml of PEG, then 4 mls of I-DMEM was added and transferred to a 37° C. water bath for 5 minutes. After centrifugation, the media was removed and the cells were transferred to a warmed flask containing 200 mls of Med-E/HAT and distributed into 40×96 well plates and transferred to a humidified 37° C. incubator containing 5% $CO_2$ and 95% air. After ten to eleven days of growth, supernatants from each well of the plated cells were assayed for antibodies reactive with SEZ6L2 by immunofluorescence and FACS assays.

High content immunofluorescence was used to identify wells that contain immunoglobulin that preferentially bound SEZ6L2. Briefly, HEK 293 cells transfected with human SEZ6L2 (positive) or untransfected HEK 293 cells (negative control) were incubated for 1 hour at 37° C. with hybridoma supernatant diluted 2-fold in DMEM +10% FBS. After incubation, cells were fixed in 4% formaldehyde, washed with PBS, permeabilized with 0.3% Triton-X-100, and labeled with anti-mouse Alexa 488 secondary antibodies for 1 hour at room temperature. Unbound secondary antibody was removed with PBS washes, and cells were stained with DNA dye (propidium iodide and Hoechst 33342). Hits were identified via low-resolution high throughput screening using a TTP Labtech Acumen eX3, quantifying the fluorescence differential for each sample on both positive and negative cell lines. Those hits were subsequently verified and the subcellular localization of each sample was characterized using a Thermo ArrayScan VTi to obtain high-resolution images of both cell lines. Wells containing immunoglobulin that preferentially bound the SEZ6L2 were transferred and expanded. The resulting SEZ6L2 specific clonal hybridomas were confirmed by flow cytometry.

Flow cytometry analysis confirmed that purified antibody from most or all of these hybridomas bound SEZ6L2 in a concentration-dependent manner Wells containing immunoglobulin that bound SEZ6L2-positive cells were transferred and expanded. The resulting clonal hybridomas were cryopreserved in freezing medium and stored in liquid nitrogen. Wells containing immunoglobulin that preferentially bound human SEZ6L2, as determined by a signal above background were transferred and expanded. This screen from both DNA and recombinant protein immunizations yielded seventeen murine antibodies that associated with human SEZ6L2.

Sequencing and cloning methods used to produce the recombinant antibodies described herein are described below.

Cloning VH and VL Sequences From Hybridomas

For determination of CDR sequences, total RNA was isolated from hybridoma cells using an RNeasy® kit (Qiagen, Hilden, Germany). First and second-strand cDNA synthesis was performed using a OneTaq® One-Step RT-PCR kit (New England BioLabs, Ipswich, Mass.). Several primer sets were used (Table 4). PCR products were separated by agarose electrophoresis and fragments were excised and purified by a QIAquick® gel extraction kit (Qiagen, Hilden, Germany) Fragments were cloned directly into expression vectors with BspQI (New England BioLabs, Ipswich, Mass.) by Golden Gate cloning techniques. Four colonies from each reaction were scaled up for miniprep-scale plasmid purification by SequeMid® DNA Purification Kit (Aline Biosciences, Woburn, Mass.).

TABLE 4

Oligonucleotide sequences for generating human antibodies.

| Oligonucleotide Sequence | Oligonucleotide Purpose |
|---|---|
| ATAGCTCTTCAGGGaccATGAARCAYCTGTGGTTCTTCCT (SEQ ID NO: 172) | IGHV4 signal peptide |
| ATAGCTCTTCAGGGaccATGGACATACTTTGTTCCACGC (SEQ ID NO: 173) | IGHV2 signal peptide |
| ATAGCTCTTCAGGGaccATGGACACACTTTGCTACACAC (SEQ ID NO: 174) | IGHV2-26 signal peptide |
| ATAGCTCTTCAGGGaccATGTCTGTCTCCTTCCTCATCT (SEQ ID NO: 175) | IGHV6 signal peptide |
| ATAGCTCTTCAGGGaccATGGACTGGACCTGGAGVATC (SEQ ID NO: 176) | IGHV1 signal peptide |
| ATAGCTCTTCAGGGaccATGGACTGGATTTGGAGGRTC (SEQ ID NO: 177) | IGHV1-58 signal peptide |
| ATAGCTCTTCAGGGaccATGGACTGCACCTGGAGGATC (SEQ ID NO: 178) | IGHV1-24 signal peptide |
| ATAGCTCTTCAGGGaccATGGACTGGACCTGGAGGKTC (SEQ ID NO: 179) | IGHV1-69/1-46/7-41 signal peptide |
| ATAGCTCTTCAGGGaccATGGAGTTKGGRCTGAGCTGG (SEQ ID NO: 180) | IGHV3 signal peptide |
| ATAGCTCTTCAGGGaccATGGAGTTTKGGCTKAGCTGG (SEQ ID NO: 181) | IGHV3-53/3-49 signal peptide |
| ATAGCTCTTCAGGGaccATGGAACTGGGGCTCCGCTGG (SEQ ID NO: 182) | IGHV3-21 signal peptide |
| ATAGCTCTTCAGGGaccATGGARTTGGGGCTGWGCTGG (SEQ ID NO: 183) | IGHV3-48/3-7 signal peptide |
| ATAGCTCTTCAGGGaccATGGGGTCAACCGCCATCCTC (SEQ ID NO: 184) | IGHV5 signal peptide |
| ATAGCTCTTCAGGGaccATGGACATGAGGGTSCCYGCTCAGCTC (SEQ ID NO: 185) | IgkV1a signal peptide |
| ATAGCTCTTCAGGGaccATGGACATGAGRGTCCTCGCTCAGCTC (SEQ ID NO: 186) | IgkV1b signal peptide |
| ATAGCTCTTCAGGGaccATGGAAGCCCCAGCDCAGCTTCTC (SEQ ID NO: 187) | IgkV3 signal peptide |
| ATAGCTCTTCAGGGaccATGGAAACCCCAGCGCAGCTTCTC (SEQ ID NO: 188) | IgkV3-20 signal peptide |
| ATAGCTCTTCAGGGaccATGGTGTTGCAGACCCAGGTCTTC (SEQ ID NO: 189) | IgkV4 signal peptide |
| ATAGCTCTTCAGGGaccATGGGGTCCCAGGTTCACCTCCTC (SEQ ID NO: 190) | IgkV5 signal peptide |
| ATAGCTCTTCAGGGaccATGAGGCTCCYTGCTCAGCTCCTG (SEQ ID NO: 191) | IgkV2 signal peptide |
| ATAGCTCTTCTTCGTTTGATCTCCASCTTGGTC (SEQ ID NO: 192) | KappaFW4 |
| ATAGCTCTTCTTCGTTTAATCTCCAGTCGTGTC (SEQ ID NO: 193) | KappaFW4 |
| ATAGCTCTTCTGGCTGAGGAGACGGTGACC (SEQ ID NO: 194) | HeavyFW4 |
| ATAGCTCTTCATGTGACGCTGTTGTGACTCAGGA (SEQ ID NO: 195) | VL-FOR L1 |
| ATAGCTCTTCATGTGACCYTGTGCTCACTCAGTC (SEQ ID NO: 196) | VL-FOR L2 |
| GATGCTCTTCTGGGCTGGCCTAGGACAGTCAMCYTGG (SEQ ID NO: 197) | VL-REV L |

Identification of Functional, Recombinant VH and VL Sequences

For each hybridoma, each plasmid was sent for Sanger Sequencing. These plasmids were subjected to DNA sequence determination and analysis.

For each hybridoma, unique recombinant heavy chains were paired with unique recombinant light chains. These plasmid pairs were transfected into CHO cells in 24-well plates. Ten days later, conditioned medium from each pairing was screened by FLOW or Octet for binding to the target.

Transient Expression System

The SEZ6L2 recombinant proteins and anti-SEZ6L2 antibodies were expressed in Chinese hamster ovary (CHO) cells using recommended transfection and media components of the ExpiCHO system (Invitrogen, Carlsbad, Calif.). Cell culture supernatants were harvested 14 days post-transfection, centrifuged, and filtered (0.22 um).

Purification of Recombinant His-Tagged Proteins

Conditioned medium from CHO cell cultures was clarified, filtered, and loaded onto an ÄKTAprime plus system with a 5 mL HisTrap™ FF column (GE Healthcare). Fractions were collected, analyzed by SDS-PAGE, pooled, and dialyzed against PBS.

Antibody Purification

Conditioned medium from CHO cell cultures was clarified, filtered, and purified by loading onto an ÄKTA pure system with a 5 mL MabSelect SuRe® column (GE Healthcare). Antibodies were eluted with 100 mM glycine, pH 3.5 and neutralized with 1M Tris-Cl, pH 8.5.

Recombinant Antibody Analyses

Concentration: Concentration of recombinant antibodies was determined on a Fortebio Octet using Protein A tips and a human IgG1 antibody for the standard curve.

Purity testing by SDS-PAGE: Purity testing was performed by sodium dodecyl sulfate polyacrylamide gel electrophoresis (SDS-PAGE) of reduced and non-reduced samples. Samples (10 ug) were mixed with loading buffer (+/−β-mercaptoethanol), heated, and electrophoresed on a 4-20% gel (Invitrogen). Bands were visualized by Coomassie InstantBlue (Expedeon) staining.

Purity testing by Endotoxin: Endotoxin concentrations were measured by the Limulus amoebocyte lysate (LAL) kinetic turbidometric method using the Endosafe-PTS system (Charles River Laboratories).

Purity testing by HPLC-SEC: Samples were screened for aggregation or other forms of antibody on a 1260 Infinity System (Agilent) with a TSKgel UltraSW Aggregate Guard column and HPLC column (Tosoh Bioscience). Samples and standards were detected by absorbance at 280 nm. Comparison against the standard curve provided the molar mass of sample components.

Affinity: The affinity of antibodies to various recombinant SEZ6L2 molecules was determined on an Octet Red (Pall, ForteBio) instrument. After loading reagents into a 96-well plate, the Octet Red with Protein A-conjugated biosensors was programmed as follows: 30 seconds for baseline #1; 120 seconds to immobilize the antibody; 30 seconds for baseline #2; 300 seconds for association of antibody to recombinant SEZ6L2; and 300-600 seconds for dissociation of recombinant SEZ6L2 from the antibody.

Example 3

Humanization of Murine Antibodies

Four of the murine antibodies produced as described in Example 2 (mu16H8, mu3E2, mu20C4, and mu2E4) were humanized using complementarity determining region (CDR) grafting. The heavy and light chain variable region amino acid sequences of the four murine antibodies are set forth below:

```
mu 16H8
Heavy Chain:
                                      (SEQ ID NO: 156)
QIQLQQPGTVLARPGASVKMSCKASGYTFTSYWMYWVKQRPGQGLEWIGA

IYPRDSDTSYNQKFKGKAKLTAVTSASTAYMELSSLTNEDSAVYYCTRGD

YYYGSSYYAMDYWGQGTTLTVSS

Light Chain:
                                      (SEQ ID NO: 158)
DIVITQAAFSNPVTLGTSASISCSCSKSLLHSNGITYLYWYLQRPGQSPQ

LLIYRMSNLASGVPDRFSGSGSGTDFTLRISRVEAEDVGVYYCAQMLERP

YTFGGGTKLEIK mu3E2
Heavy Chain:
                                      (SEQ ID NO: 160)
EVLLVESGGRLVQPKGSLKLSCAASGFSFNTITMNWVRQAPGKGLEWVAR

IRSKSNNYATYYADAVKDRFTISRDDSQSMLYLQMNNLKTEDTAMYFCVR

GIFSGYVYAMDYWGQGTTLTVSS

Light Chain:
                                      (SEQ ID NO: 161)
DVVMTQSPLSLPVSVGDQASISCRSSQSIVHSNGNTYLEWYLQKPGQSPK

VLIYKVSNRFSGVPDRFSGSGSGTDFTLKISRVEAEDLGVYYCFQGSHVP

YTFGGGTKLEIK mu20C4
Heavy Chain:
                                      (SEQ ID NO: 162)
EVLLVESGGRLVQPKGSLKLSCAASGFSFNTITMNWVRQAPGKGLEWVAR

IRSKSNNYATYYADAVKDRFTISRDDSQSMLYLQMNNLKTEDTAMYFCVR

GIFSGYVYAMDYWGQGTTLTVSS

Light Chain:
                                      (SEQ ID NO: 164)
DVVMTQSPLSLPVSVGDQASISCRSSQSIVHSNGNTYLEWYLQKPGQSPK

VLIYKVSNRFSGVPDRFSGSGSGTDFTLKISRVEAEDLGVYYCFQGSHVP

YTFGGGTKLEIK mu2E4
Heavy Chain:
                                      (SEQ ID NO: 165)
EVKLVESGGVLVKPGGSLKLSCAASGFTFSKYAMSWVRQTPEKRLEWVAT

ISSGGSYTYYPDSVKGRFTISRDNARNTLYLQMSSLRSEDTAIYYCTREG

GYDEGYAMDYWGQGTTLTVS

Light Chain:
                                      (SEQ ID NO: 166)
DVVMTQTPLSLPVSLGDQASISCRSSQSLVHSYGNTYLHWYLQKPGQSPK

LLIYKVSNRFSGVPDRFSGSGSGTDFTLKISRVEAEDLGVYFCSQSTHFR

TFGGGTKLEIK
```

Human frameworks for heavy and light chains were selected based on sequence similarity with respect to functional human germline genes. The human structural homologs or human counterpart of murine antibodies were selected using Bioluminate (Schrödinger LLC). The software uses experimentally determined antibody structures available from the publicly available Protein Data Bank (www.rcsb.org/pdb).

Specifically, four murine antibodies were humanized using a computer-aided CDR-grafting method and standard molecular engineering techniques to provide the human counterpart. The human counterparts were selected by comparing light and heavy chain variable regions or framework regions of the murine antibody to available human light and heavy chain variable regions or framework regions with existing structures. For the purposes of the humanization analysis, the assignment of amino acids to each of the CDR domains is in accordance with Kabat numbering.

Molecular engineering procedures were conducted using art recognized techniques. To that end, total mRNA was extracted from the hybridomas and amplified using art recognized techniques. From the nucleotide sequence information, data regarding V, D and J gene segments of the heavy and light chains of subject murine antibodies were obtained. Based on the sequence data, new primer sets specific to the signal peptide sequence of the IgVh and Vk light chains of the antibodies were designed for cloning of the recombinant monoclonal antibody. Subsequently, the V-D-J sequences were aligned with mouse IgG germ line sequences. The resulting genetic arrangements for each of the four humanized constructs, 16H8, 3E2, 20C4, and 2E4, are shown in Table 5, below.

TABLE 5

Genetic arrangements for humanized constructs.

| Humanized antibody | Human VH | Human JH | FW changes | Human VK | Human JK | FW changes |
|---|---|---|---|---|---|---|
| 16H8 | IGHV1-46 | | V2I, S7P, D72V | IGKV2-28 | JK1 | none |
| 3E2 | IGHV3-73 | JH4 | T93V | IGKV1-11 | JK4 | L15V, R46V, V104L |
| 20C4 | IGHV3-72 | JH4 | G49A, D73N, K83R, T84A | IGKV2-28 | JK4 | S7T, L11I, V83F, G100A |
| 2E4 | IGHV3-21 | JH6 | K3Q, G10V, K75R, V89I, A93T | IGKV4-1 | JK4 | Y87F |

Table 5 further demonstrates that few framework changes were necessary to maintain the favorable properties of the antibodies. In this respect, framework changes or back mutations were only made in three of the heavy chain variable regions and only two framework modifications were undertaken in the light chain variable regions.

The humanized antibodies 16H8, 3E2, 20C4, and 2E4 correspond to the light and heavy chain sequences set forth below in Table 6.

TABLE 6

Variable Region Sequences of Humanized Antibodies 16H8, 3E2, 20C4, and 2E4

| SEQ ID NO: | Clone | Protein Region | V Region |
|---|---|---|---|
| 1 | 16H8 | VH | QIQLVQPGAEVKKPGASVKVSCKASGYTFTSYWMYWVRQAPGQG LEWMGAIYPRDSDTSYNQKFKGRVTMTRVTSTSTVYMELSSLRS EDTAVYYCTRGDYYYGSSYYAMDYWGQGTTVTVSSA |
| 2 | 16H8 | CDR-H1 | GYTFTSYWMY |
| 3 | 16H8 | CDR-H2 | AIYPRDSDTSYNQKFKG |
| 4 | 16H8 | CDR-H3 | GDYYYGSSYYAMDY |
| 5 | 16H8 | VL | DIVMTQSPLSLPVTPGEPASISCSSSKSLLHSNGITYLYWYLQK PGQSPQLLIYRMSNLASGVPDRFSGSGSGTDFTLKISRVEAEDV GVYYCAQMLERPYTFGQGTKVETKR |
| 6 | 16H8 | CDR-L1 | SSSKSLLHSNGITYLY |
| 7 | 16H8 | CDR-L2 | RMSNLAS |
| 8 | 16H8 | CDR-L3 | AQMLERPYT |
| 9 | 3E2 | VH | EVQLVESGGGLVQPGGSLKLSCAASGFSFNTITMNWVRQASGKG LEWVGRIRSKSNNYATYYADAVKDRFTISRDDSKNTAYLQMNSL KTEDTAVYYCVRGIFSGYVYAMDYWGQGTLVTVSSA |

TABLE 6-continued

Variable Region Sequences of Humanized Antibodies 16H8, 3E2, 20C4, and 2E4

| SEQ ID NO: | Clone | Protein Region | V Region |
|---|---|---|---|
| 10 | 3E2 | CDR-H1 | GFSFNTITMN |
| 11 | 3E2 | CDR-H2 | RIRSKSNNYATYYADAVKD |
| 12 | 3E2 | CDR-H3 | GIFSGYVYAMDY |
| 13 | 3E2 | VL | DVVMTQSPLSLPVTVGQPASISCRSSQSIVHSNGNTYLEWFQQR PGQSPRVLIYKVSNRFSGVPDRFSGSGSGTDFTLKISRVEAEDV GVYYCFQGSHVPYTFGGGTKLETKR |
| 14 | 3E2 | CDR-L1 | RSSQSIVHSNGNTYLE |
| 15 | 3E2 | CDR-L2 | KVSNRFS |
| 16 | 3E2 | CDR-L3 | FQGSHVPYT |
| 17 | 20C4 | VH | EVQLVESGGGLVQPGGSLRLSCAASGFTFTDYYMSWVRQAPGKG LEWVALIRNKANGYTTEYSASVKGRFTISRDNSKNSLYLQMNSL RAEDTAVYYCARNGLYGLFAYWGQGTLVTVSSA |
| 18 | 20C4 | CDR-H1 | GFTFTDYYMS |
| 19 | 20C4 | CDR-H2 | TRNKANGYTTEYSASVKG |
| 20 | 20C4 | CDR-H3 | NGLYGLFAY |
| 21 | 20C4 | VL | DIVMTQTPLSIPVTPGEPASISCRSSTSLLESSGKHRLYWYLQK PGQSPQLLIYYMSNLASGVPDRFSGSGSGTDFTLKISRVEAEDF GVYYCMQSLEYPLTFGAGTKVETKR |
| 22 | 20C4 | CDR-L1 | RSSTSLLESSGKHRLY |
| 23 | 20C4 | CDR-L2 | YMSNLAS |
| 24 | 20C4 | CDR-L3 | MQSLEYPLT |
| 25 | 2E4 | VH | EVKLVESGGVLVKPGGSLRLSCAASGFTFSKYAMSWVRQAPGKG LEWVSTISSGGSYTYYPDSVKGRFTISRDNARNSLYLQMNSLRA EDTAIYYCTREGGYDEGYAMDYWGQGTTVTVSSA |
| 26 | 2E4 | CDR-H1 | GFTFSKYAMS |
| 27 | 2E4 | CDR-H2 | TISSGGSYTYYPDSVKG |
| 28 | 2E4 | CDR-H3 | EGGYDEGYAMDY |
| 29 | 2E4 | VL | DIVMTQSPDSLAVSLGERATINCRSSQSLVHSYGNTYLHWYQQK PGQPPKLLIYKVSNRFSGVPDRFSGSGSGTDFTLTISSLQAEDV AVYFCSQSTHFRTFGGGTKVEIKR |
| 30 | 2E4 | CDR-L1 | RSSQSLVHSYGNTYLH |
| 15 | 2E4 | CDR-L2 | KVSNRFS |
| 31 | 2E4 | CDR-L3 | SQSTHFRT |

Note that for some humanized light and heavy chain variable regions, conservative amino acid mutations were introduced in the CDRs to address stability concerns while maintaining antigen binding. In each case the binding affinity of the antibodies with modified CDRs was found to be equivalent to either the corresponding chimeric or murine antibody.

Following humanization of all selected antibodies by CDR grafting, the resulting light and heavy chain variable region amino acid sequences were analyzed to determine their homology with regard to the murine donor and human acceptor light and heavy chain variable regions. The results, shown in Table 7, below, reveal that the humanized constructs consistently exhibited an equivalent percentage homology to a closest match of human germline genes (83% to 91%) as compared to the homology of the humanized variable region sequences to the donor hybridoma protein sequences (83% to 91%).

TABLE 7

Percent homology to CDR acceptor (human) and donor (murine parent)

| Humanized mAb | Homology to Human (CDR acceptor) | Homology to Murine Parent (CDR donor) |
|---|---|---|
| 16H8 | 86% | 77% |
| 16H8 | 88% | 91% |
| 3E2 | 87% | 88% |
| 3E2 | 91% | 88% |

TABLE 7-continued

Percent homology to CDR acceptor (human) and donor (murine parent)

| Humanized mAb | Homology to Human (CDR acceptor) | Homology to Murine Parent (CDR donor) |
|---|---|---|
| 20C4 | 89% | 88% |
| 20C4 | 83% | 83% |
| 2E4 | 87% | 86% |
| 2E4 | 84% | 83% |

Whether humanized or murine, once the nucleic acid sequences of the variable regions were determined, the antibodies were expressed and isolated using art recognized techniques. To that end, synthetic DNA fragments of the chosen heavy chain (humanized or murine) variable region were cloned into a human IgG1 expression vector. Similarly the variable region light chain DNA fragment (again humanized or murine) was cloned into a human light chain expression vector.

The selected antibody was then expressed by co-transfection of the derived heavy and the light chain nucleic acid constructs into ExpiCHO cells. More particularly, one compatible method of antibody production comprised directional cloning of murine or humanized variable region genes (amplified using PCR) into selected human immunoglobulin expression vectors. All primers used in Ig gene-specific PCRs included restriction sites which allowed direct cloning into expression vectors containing human IgG1 heavy chain and light chain constant regions. Primers are set forth below in Table 8.

TABLE 8

| Species | chain | | region | Name | Final primer | |
|---|---|---|---|---|---|---|
| mouse | Kappa | 5' | FWR1 | BspQI_16 | ATAGCTCTTCATGTGACAWTGTTCTCACCCAGTC (SEQ ID NO: 198) | VL-FOR K1 |
| mouse | Kappa | 5' | FWR1 | BspQI_17 | ATAGCTCTTCATGTGACATCCAGATGACACAGWC (SEQ ID NO: 199) | VL-FOR K2 |
| mouse | Kappa | 5' | FWR1 | BspQI_18 | ATAGCTCTTCATGTGATRTTGTGATGACCCAGWC (SEQ ID NO: 200) | VL-FOR K3 |
| mouse | Kappa | 5' | FWR1 | BspQI_19 | ATAGCTCTTCATGTGACATTSTGMTGACCCAGTC (SEQ ID NO: 201) | VL-FOR K4 |
| mouse | Kappa | 5' | FWR1 | BspQI_20 | ATAGCTCTTCATGTGATGTTGTGVTGACCCAAAC (SEQ ID NO: 202) | VL-FOR K5 |
| mouse | Kappa | 5' | FWR1 | BspQI_21 | ATAGCTCTTCATGTGACACAACTGTGACCCAGTC (SEQ ID NO: 203) | VL-FOR K6 |
| mouse | Kappa | 5' | FWR1 | BspQI_22 | ATAGCTCTTCATGTGAYATTKTGCTCACTCAGTC (SEQ ID NO: 204) | VL-FOR K7 |
| mouse | Kappa | 5' | FWR1 | BspQI_23 | ATAGCTCTTCATGTGATATTGTGATRACCCAGGM (SEQ ID NO: 205) | VL-FOR K8 |
| mouse | Kappa | 5' | FWR1 | BspQI_24 | ATAGCTCTTCATGTGACATTGTAATGACCCAATC (SEQ ID NO: 206) | VL-FOR K9 |
| mouse | Kappa | 5' | FWR1 | BspQI_25 | ATAGCTCTTCATGTGACATTGTGATGWCACAGTC (SEQ ID NO: 207) | VL-FOR K10 |
| mouse | Kappa | 5' | FWR1 | BspQI_26 | ATAGCTCTTCATGTGATRTCCAGATGAMCCAGTC (SEQ ID NO: 208) | VL-FOR K11 |
| mouse | Kappa | 5' | FWR1 | BspQI_27 | ATAGCTCTTCATGTGATGGAGAAACAACACAGGC (SEQ ID NO: 209) | VL-FOR K12 |
| mouse | Lambda | 5' | FWR1 | BspQI_28 | ATAGCTCTTCATGTGACGCTGTTGTGACTCAGGA (SEQ ID NO: 210) | VL-FOR L1 |
| mouse | Lambda | 5' | FWR1 | BspQI_29 | ATAGCTCTTCATGTGACCYTGTGCTCACTCAGTC (SEQ ID NO: 211) | VL-FOR L2 |

TABLE 8-continued

| Species | chain | region | Name | Final primer | | |
|---|---|---|---|---|---|---|
| mouse | Kappa | 3' FWR4 | BspQI_30 | GATGCTCTTCGTCGTTTBATTTCCAGC TTGG (SEQ ID NO: 212) | VL-REV K1 | |
| mouse | Kappa | 3' FWR4 | BspQI_31 | GATGCTCTTCGTCGTTTTATTTCCAAT TTTG (SEQ ID NO: 213) | VL-REV-K2 | |
| mouse | Lambda | 3' FWR4 | BspQI_32 | GATGCTCTTCTGGGCTGGCCTAGGACA GTCAMCYTGG (SEQ ID NO: 214) | VL-REV L | |
| mouse | Gamma | 5' FWR1 | BspQI_33 | ATAGCTCTTCATGTGAGGTTCDSCTGC AACAGTY (SEQ ID NO: 215) | VH-FOR 1 | |
| mouse | Gamma | 5' FWR1 | BspQI_34 | ATAGCTCTTCATGTCAGGTGCAAMTGM AGSAGTC (SEQ ID NO: 216) | VH-FOR 2 | |
| mouse | Gamma | 5' FWR1 | BspQI_35 | ATAGCTCTTCATGTGAVGTGMWGCTGG TGGAGTC (SEQ ID NO: 217) | VH-FOR 3 | |
| mouse | Gamma | 5' FWR1 | BspQI_36 | ATAGCTCTTCATGTCAGGTTAYTCTGA AAGAGTC (SEQ ID NO: 218) | VH-FOR 4 | |
| mouse | Gamma | 5' FWR1 | BspQI_37 | ATAGCTCTTCATGTGAKGTGCAGCTTC AGSAGTC (SEQ ID NO: 219) | VH-FOR 5 | |
| mouse | Gamma | 5' FWR1 | BspQI_38 | ATAGCTCTTCATGTCAGATCCAGTTSG YGCAGTC (SEQ ID NO: 220) | VH-FOR 6 | |
| mouse | Gamma | 5' FWR1 | BspQI_39 | ATAGCTCTTCATGTCAGRTCCAACTGC AGCAGYC (SEQ ID NO: 221) | VH-FOR 7 | |
| mouse | Gamma | 5' FWR1 | BspQI_40 | ATAGCTCTTCATGTGAGGTGMAGCTAS TTGAGWC (SEQ ID NO: 222) | VH-FOR 8 | |
| mouse | Gamma | 5' FWR1 | BspQI_41 | ATAGCTCTTCATGTGAAGTGAAGMTTG AGGAGTC (SEQ ID NO: 223) | VH-FOR 9 | |
| mouse | Gamma | 5' FWR1 | BspQI_42 | ATAGCTCTTCATGTGATGTGAACCTGG AAGTGTC (SEQ ID NO: 224) | VH-FOR 10 | |
| mouse | Gamma | 5' FWR1 | BspQI_43 | ATAGCTCTTCATGTCAGATKCAGCTTM AGGAGTC (SEQ ID NO: 225) | VH-FOR 11 | |
| mouse | Gamma | 5' FWR1 | BspQI_44 | ATAGCTCTTCATGTCAGGCTTATCTGC AGCAGTC (SEQ ID NO: 226) | VH-FOR 12 | |
| mouse | Gamma | 5' FWR1 | BspQI_45 | ATAGCTCTTCATGTCAGGTTCACCTAC AACAGTC (SEQ ID NO: 227) | VH-FOR 13 | |
| mouse | Gamma | 5' FWR1 | BspQI_46 | ATAGCTCTTCATGTCAGGTGCAGCTTG TAGAGAC (SEQ ID NO: 228) | VH-FOR 14 | |
| mouse | Gamma | 5' FWR1 | BspQI_47 | ATAGCTCTTCATGTGARGTGMAGCTGK TGGAGAC (SEQ ID NO: 229) | VH-FOR 15 | |
| mouse | Gamma | 3' FWR4 | BspQI_48 | GATGCTCTTCTGGCCGAGGAGACGGTG ACMGTGG (SEQ ID NO: 230) | VH-REV 1 | |
| mouse | Gamma | 3' FWR4 | BspQI_49 | GATGCTCTTCTGGCCGCAGAGACAGTG ACCAGAG (SEQ ID NO: 231) | VH-REV 2 | |
| mouse | Gamma | 3' FWR4 | BspQI_50 | GATGCTCTTCTGGCCGAGGAGACTGTG AGASTGG (SEQ ID NO: 232) | VH-REV 3 | |

Cells producing the selected antibody were generated by transfection of ExpiCHO cells with the appropriate plasmids using Expifectamine (Thermo #A29129) following manufacturer's recommendations. Plasmid DNA was purified using Qiagen's CompactPrep plasmid midi kit (#12843). ExpiCHO cells (Thermo #A29127) were cultured in shake flasks under standard conditions in ExpiCHO expression medium (Thermo #A2910001). Equal amounts of IgH and corresponding IgL chain vector DNA (40 μgs each) was added to 4 mls of OptiPRO SFM (Thermo #12309019). This mix was combined with 320 μls Expifectamine, 4 mls OptiPRO SFM and added slowly to the cells with gently swirling. Supernatants were harvested 14 days after transfection, then were cleared of cell debris by centrifugation at 4000×g, sterile filtered (0.2 um), and stored at 4° C. Recombinant human antibodies were then purified with Protein A mAb Select Sure (GE LifeSciences) and stored under appropriate conditions.

Example 4

Generation of Human Antibodies

Human SEZ6L2 antibodies were produced in accordance with the teachings herein through inoculation with a protein composed of the extracellular portion of the human SEZ6L2 protein (SEZ6L2-his) as described in Example 2. H2L2 mice were used to generate high affinity, fully human monoclonal antibodies that can associate with and/or inhibit the activity of SEZ6L2.

Two immunization approaches were used. In the first approach, four H2L2 mice were dosed biweekly for four weeks with 5 to 10 μgs of purified, recombinant SEZ6L2-his protein emulsified with non-denaturing adjuvant (Alhydrogel) in the footpad, followed a few days later with final boost. Two mice were fused after four weeks, and two other mice were continued for an additional two weeks with biweekly immunization before fusion. In the second immunization approach, six H2L2 mice were dosed once per week for 9 weeks with 50 ugs of recombinant SEZ6L2-his protein in denaturing adjuvant (Freund's) via IP route.

Sera-positive immunized mice were sacrificed and spleens and/or draining lymph nodes were dissected out and used as a source for antibody producing cells. Fusion was performed using a PEG/HAT approach using art recognized techniques. Fused cells were cultured in T75 flasks and tested for binding to SEZ6L2 by ELISA and flow analysis using overexpression 293 cells. Individual cells from flasks containing IgG that binds SEZ6L2 were then sorted into 30×96 well plates to isolate clones. These wells were cultured and then screened again by high throughput flow analysis, and wells containing immunoglobulin that preferentially bound human SEZ6L2, as determined by a signal above background, were transferred and expanded.

The human antibodies 1A1, 1D2, 1E4, 3A1, 3B1, 3B3, 3A2, 3A3, 3A4, 106, 1C1, 1D5, 3B6, 3B2, 2M5_10A1, and 2M22_10A6 correspond to the light and heavy chain sequences set forth below in Table 9.

TABLE 9

Variable Region Sequences of Human Antibodies

| SEQ ID NO: | Clone | Protein Region | V Region |
|---|---|---|---|
| 32 | 1A1 | VH | QVQLVQSGAEVKKPGASVKVSCKASGYTFTGYYMFWVRQAPGQGLEWLGWINPNSGGTDYAQKFQGRVTMTRDTSISTAYMELSRLRSDDTAVYYCARDSGYDWFFDYWGQGTLVTVSS |
| 33 | 1A1 | CDR-H1 | GYTFTGYYMF |
| 34 | 1A1 | CDR-H2 | WINPNSGGTDYAQKFQG |
| 35 | 1A1 | CDR-H3 | DSGYDWFFDY |
| 36 | 1A1 | VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPPFTFGPGTKLEIK |
| 37 | 1A1 | CDR-L1 | RASQSVSSNLA |
| 38 | 1A1 | CDR-L2 | GASTRAT |
| 39 | 1A1 | CDR-L3 | QQYNNWPPFT |
| 40 | 1D2 | VH | QVQLVQSGAEVKKPGASVKVSCKASGYTFTGYYMHWVRQAPGQGLEWMGWINPNNGGTNYAQKFQGRVTMTRDTSISTAYMELRRLRSDDTAVYYCARDQNSGWLFDYWGQGTLVTVSS |
| 41 | 1D2 | CDR-H1 | GYTFTGYYMH |
| 42 | 1D2 | CDR-H2 | WINPNNGGTNYAQKFQG |
| 43 | 1D2 | CDR-H3 | DQNSGWLFDY |
| 44 | 1D2 | VL | EIVMTQSPATLSVSPGERATLSCRASQSVSSNSAWYQQKPGQAPRLLIYGASTRATGIPARFSGSGSGTEFTLTISSLQSEDFAVYYCQQYNNWPPITFGQGTRLEIK |
| 45 | 1D2 | CDR-L1 | RASQSVSSNSA |
| 38 | 1D2 | CDR-L2 | GASTRAT |

TABLE 9-continued

Variable Region Sequences of Human Antibodies

| SEQ ID NO: | Clone | Protein Region | V Region |
|---|---|---|---|
| 46 | 1D2 | CDR-L3 | QQYNNWPPIT |
| 32 | 1E4 | VH | QVQLVQSGAEVKKPGASVKVSCKASGYTFTGYYMFWVRQAPGQGLEWLGWINPNSGGTDYAQKFQGRVTMTRDTSISTAYMELSRLRSDDTAVYYCARDSGYDWFFDYWGQGTLVTVSS |
| 33 | 1E4 | CDR-H1 | GYTFTGYYMF |
| 34 | 1E4 | CDR-H2 | WINPNSGGTDYAQKFQG |
| 35 | 1E4 | CDR-H3 | DSGYDWFFDY |
| 47 | 1E4 | VL | DIQMTQSPSTLSASVGDRVTITCRASQSISSWLAWYQQKPGKAPKLLIYKASSLESGVPSRFSGSGSGTEFTLTISSLQPDDFATYYCQQYNSYSYTFGQGTKVEIK |
| 48 | 1E4 | CDR-L1 | RASQSISSWLA |
| 49 | 1E4 | CDR-L2 | KASSLES |
| 50 | 1E4 | CDR-L3 | QQYNSYSYT |
| 51 | 3A1 | VH | QVQLVQSGAEVKKPGASVKVSCKASGFTFTGYYILWMRQAPGQGLEWMGWINPNNGGTHYAQKFQGRVTMTRDTSISTAYMELSRLRSDDTAVYYCARDSGHDWYFDLWGRGTLVTVSSA |
| 52 | 3A1 | CDR-H1 | GFTFTGYYIL |
| 53 | 3A1 | CDR-H2 | WINPNNGGTHYAQKFQG |
| 54 | 3A1 | CDR-H3 | DSGHDWYFDL |
| 55 | 3A1 | VL | EIVLTQSPATLSLSPGERATLSCRASQSVSSSLAWYQQKPGQAPRLLIYDASNRATGIPARFSGSGSGTDFTLTISSLEPEDFAVYYCQQHSNWPPLTFGGGTKVEIKR |
| 56 | 3A1 | CDR-L1 | RASQSVSSSLA |
| 57 | 3A1 | CDR-L2 | DASNRAT |
| 58 | 3A1 | CDR-L3 | QQHSNWPPLT |
| 59 | 3B1 | VH | QVQLVESGGGVVQPGRSLRLTCVVSGFAFSSYGMHWVRQAPGKGLEWVAVIWYDGSNKYYADSVKGRFTISRDNSKNTLYLQMNSLRAEDTAVYYCASLDYYGSGSRFDPWGQGTLVTVSSA |
| 60 | 3B1 | CDR-H1 | GFAFSSYGMH |
| 61 | 3B1 | CDR-H2 | VIWYDGSNKYYADSVKG |
| 62 | 3B1 | CDR-H3 | LDYYGSGSRFDP |
| 63 | 3B1 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPYTFGQGTKLEIKR |
| 64 | 3B1 | CDR-L1 | RSSQSLLHSNGYNYLD |
| 65 | 3B1 | CDR-L2 | LGSNRAS |
| 66 | 3B1 | CDR-L3 | MQALQTPYT |
| 67 | 3B3 | VH | EVQLVESGGGLVQPGGSLRLSCAASGFTFSSYWMSWVRQAPGKGLEWVANIKQDGSEKYYVDSVKGRFTISRDNAKNSLYLQMNSLRAEDTAVYYCARGGGSYAFDYWGQGTLVTVSSA |
| 68 | 3B3 | CDR-H1 | GFTFSSYWMS |
| 69 | 3B3 | CDR-H2 | NIKQDGSEKYYVDSVKG |
| 70 | 3B3 | CDR-H3 | GGGSYAFDY |
| 71 | 3B3 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPRTFGQGTKVEIKR |

TABLE 9-continued

Variable Region Sequences of Human Antibodies

| SEQ ID NO: | Clone | Protein Region | V Region |
|---|---|---|---|
| 64 | 3B3 | CDR-L1 | RSSQSLLHSNGYNYLD |
| 65 | 3B3 | CDR-L2 | LGSNRAS |
| 72 | 3B3 | CDR-L3 | MQALQTPRT |
| 73 | 3A2 VH | | QVQLQESGPGLVKPSGTLSLTCAVSGGSISSYHWWSWVRQPPG KGLEWIGEIYHSGSTNYNPSLKSRVTISVDKSKNQFSLKLSSV TAADTAVYYCARWGRIAVADYWGQGTLVTVSSA |
| 74 | 3A2 | CDR-H1 | GGSISSYHWWS |
| 75 | 3A2 | CDR-H2 | EIYHSGSTNYNPSLKS |
| 76 | 3A2 | CDR-H3 | WGRIAVADY |
| 77 | 3A2 VL | | DIQMTQSPSTLSASVGDRVTITCRASQSISSWLAWYQQKPGKA PKLLIYKASSLESGVPSRFSGSGSGTEFTLTISSLQPDDFATY YCQQYNSYWTFGQGTKVEIKR |
| 48 | 3A2 | CDR-L1 | RASQSISSWLA |
| 49 | 3A2 | CDR-L2 | KASSLES |
| 78 | 3A2 | CDR-L3 | QQYNSYWT |
| 79 | 3A3 VH | | QVQLQESGPGLVKPSGTLSLTCAVSGGSISSSNWWSWVRQPPG KGLEWIGEIYHSGSTNYNPSLKSRVTISVDKSKNQFSLKLSSV TAADTAVYYCAAYSGSYFEYWGQGTLVTVSSA |
| 80 | 3A3 | CDR-H1 | GGSISSSNWWS |
| 75 | 3A3 | CDR-H2 | EIYHSGSTNYNPSLKS |
| 81 | 3A3 | CDR-H3 | YSGSYFEY |
| 82 | 3A3 VL | | DIQMTQSPSTLSASVGDRVTITCRASQSISSWLAWYQQKPGKA PKLLIYKASSLESGVPSRFSGSGSGTEFTLTISSLQPDDFATY YCQQYNSYPLTFGGGTKLEIKR |
| 48 | 3A3 | CDR-L1 | RASQSISSWLA |
| 49 | 3A3 | CDR-L2 | KASSLES |
| 83 | 3A3 | CDR-L3 | QQYNSYPLT |
| 84 | 3A4 VH | | QVQLQESGPGLVKPSETLSLTCTVSGDSISSYYWSWIRQPPGK GLEWIGYIFYSGSTNYNPSLKSRVTISVDTSKNQFSLKLSSVT AADTAVYYCARDSSGWYGGVDYWGQGTLVTVSS |
| 85 | 3A4 | CDR-H1 | GDSISSYYWS |
| 86 | 3A4 | CDR-H2 | YIFYSGSTNYNPSLKS |
| 87 | 3A4 | CDR-H3 | DSSG |
| 88 | 3A4 VL | | EIVMTQSPATLSVSPGERATLSCRASQSVSSNLAWYQQKPGQA PRLLIYGASTRATGIPARFSGSGSGTEFTLTISSLQSEDFAVY YCQQYNNWPLTFGGGTKVEIK |
| 37 | 3A4 | CDR-L1 | RASQSVSSNLA |
| 38 | 3A4 | CDR-L2 | GASTRAT |
| 89 | 3A4 | CDR-L3 | QQYNNWPLT |
| 90 | 1C6 VH | | QVQLQESGPGLVKPSETLSLTCTVSGGSISSYYWSWIRQPPGK GLEWIGYIYNSGSTNYNPSLKSRVTISVDTSKNQFSLKLSSVT AADTAVYYCARRGDQGYWYFDLWGRGTLVTVSS |
| 91 | 1C6 | CDR-H1 | GGSISSYYWS |
| 92 | 1C6 | CDR-H2 | YIYNSGSTNYNPSLKS |

TABLE 9-continued

Variable Region Sequences of Human Antibodies

| SEQ ID NO: | Clone | Protein Region | V Region |
|---|---|---|---|
| 93 | 1C6 | CDR-H3 | RGDQGYWYFDL |
| 94 | 1C6 | VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPPTFGQGTKVEIK |
| 37 | 1C6 | CDR-L1 | RASQSVSSNLA |
| 38 | 1C6 | CDR-L2 | GASTRAT |
| 95 | 1C6 | CDR-L3 | QQYNNWPPT |
| 96 | 1C1 | VH | QVQLQQWGAGLLKPSETLSLTCAVYGGSFSAYYWSWIRQPPGKGLEWIGEINHGGSTNYNPSLKSRVTISVDTSKNQFSLKLSSVTAADTAVYYCARGRYFDWLFPAFDIWGQGTMVTVSS |
| 97 | 1C1 | CDR-H1 | GGSFSAYYWS |
| 98 | 1C1 | CDR-H2 | EINHGGSTNYNPSLKS |
| 99 | 1C1 | CDR-H3 | GRYFDWLFPAFDI |
| 100 | 1C1 | VL | DIQLTQSPSFLSASVGDRVTITCRASQGISSYLAWYQQKPGKAPKLLIYAASTLQSGVPSRFSGSGSGTEFTLTISSLQPEDFATYYCQQLNSYPFTFGPGTKVEIK |
| 101 | 1C1 | CDR-L1 | RASQGISSYLA |
| 102 | 1C1 | CDR-L2 | AASTLQS |
| 103 | 1C1 | CDR-L3 | QQLNSYPFT |
| 104 | 1D5 | VH | QVQLQESGPGLVKPSETLSLTCTVSGGSIRSYYWSWIRQPPGKGLEWIGYIHYSGSTNYNPSLKSRVTISVDTSKNQFSLKLSSVTAADTAVYYCARGSYNSGWLFDYWGQGTLVTVSS |
| 105 | 1D5 | CDR-H1 | GGSIRSYYWS |
| 106 | 1D5 | CDR-H2 | YIHYSGSTNYNPSLKS |
| 107 | 1D5 | CDR-H3 | GSYNSGWLFDY |
| 108 | 1D5 | VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPLTFGGGTKLEIK |
| 37 | 1D5 | CDR-L1 | RASQSVSSNLA |
| 38 | 1D5 | CDR-L2 | GASTRAT |
| 89 | 1D5 | CDR-L3 | QQYNNWPLT |
| 109 | 3B6 | VH | QVQLVQSGAEVKKPGASVKVSCKASGYTFTAYYMHWVRQAPGQGLEWMGWINPNSGGTNYAQKFQGRVTMTRDTSIDTAYLDLSRLRSDDTAVYYCAKDSGYDWYFDIWGRGTLVTVSSA |
| 110 | 3B6 | CDR-H1 | GYTFTAYYMH |
| 111 | 3B6 | CDR-H2 | WINPNSGGTNYAQKFQG |
| 112 | 3B6 | CDR-H3 | DSGYDWYFDI |
| 113 | 3B6 | VL | EIVLTQSPATLSLSPGERATLSCRASQNISSYLAWYQQKPGQAPRLLIYDASNRATGIPARFSGSGSGTDFTLTISSLEPEDFAVFYCQQHSNWPPLTFGGGTKVEIKR |
| 114 | 3B6 | CDR-L1 | RASQNISSYLA |
| 57 | 3B6 | CDR-L2 | DASNRAT |
| 58 | 3B6 | CDR-L3 | QQHSNWPPLT |

TABLE 9-continued

Variable Region Sequences of Human Antibodies

| SEQ ID NO: | Clone | Protein Region | V Region |
|---|---|---|---|
| 115 | 3B2 | VH | EVQLVESGGGLVQPGGSLRLSCAASGFTFSSYWMSWVRQAPGK GLEWVANIKQDGSEKYYVDSVKGRFTISRDNAKNSLYLQMNSL RAEDTAVYYCARGGGSYAFDYWGQGTLVTVSS |
| 68 | 3B2 | CDR-H1 | GFTFSSYWMS |
| 69 | 3B2 | CDR-H2 | NIKQDGSEKYYVDSVKG |
| 70 | 3B2 | CDR-H3 | GGGSYAFDY |
| 116 | 3B2 | VL | DVVMTQSPLSLPVTLGQPASISCRSSQSLVYSDGNTYLNWFQQ RPGQSPRRLIYKVSNRDSGVPDRFSGSGSGTDFTLKISRVEAE DVGVYYCMQGTHWPPLTFGGGTKVEIK |
| 117 | 3B2 | CDR-L1 | RSSQSLVYSDGNTYLN |
| 118 | 3B2 | CDR-L2 | KVSNRDS |
| 119 | 3B2 | CDR-L3 | MQGTHWPPLT |
| 233 | 2M5_10A1 | VH | QVQLVQSGAEVKKPGASVKVSCKASGYTFTGYYIHWVRQAPGQGLEW MGWINPTSGGTSYAQKFQGRVTMTRDTSISTAYMELNRLRSDDTAVY YCARGEYSSGWSFDYWGQGTLVTVSS |
| 234 | 2M5_10A1 | CDR-H1 | GYTFTGYYIH |
| 235 | 2M5_10A1 | CDR-H2 | WINPTSGGTSYAQKFQG |
| 236 | 2M5_10A1 | CDR-H3 | GEYSSGWSFDY |
| 237 | 2M5_10A1 | VL | EIVMTQSPATLSVSPGERATLSCRASQSVSSNLAWYQQKPGQAPRLL IYGASTRATGIPARFSGSGSGTEFTLTISSLQSEDFAVYYCQQYNDW PLTFGGGTKVEIK |
| 37 | 2M5_10A1 | CDR-L1 | RASQSVSSNLA |
| 38 | 2M5_10A1 | CDR-L2 | GASTRAT |
| 238 | 2M5_10A1 | CDR-L3 | QQYNDWPLT |
| 239 | 2M22_10A6 | VH | QVQLVQSGAEVKKPGASVKVSCKASGYTFTSHDINWVRQATGQGLEW MGWMNPNSGNTYAQKFQGRVTMTRNTSIGTAYMELSSLRSEDTAVY YCARGGDYYGSGSYKGHYVMDAWGQGASVTVSS |
| 240 | 2M22_10A6 | CDR-H1 | GYTFTSHDIN |
| 241 | 2M22_10A6 | CDR-H2 | WMNPNSGNTYAQKFQG |
| 242 | 2M22_10A6 | CDR-H3 | GGDYYGSGSYKGHYVMDA |
| 243 | 2M22_10A6 | VL | EIVMTQSPATLSVSPGERATLSCRASQSVSRHFAWYQQKPGQAPRLL IYGASTRATGIPARFSGSGSGTEFTLTISSLQSEDFAVYFCQHYTNW PLTFGGGTKLEIK |
| 244 | 2M22_10A6 | CDR-L1 | RASQSVSRHFA |
| 38 | 2M22_10A6 | CDR-L2 | GASTRAT |
| 245 | 2M22_10A6 | CDR-L3 | QHYTNWPLT |

Table 10, below, indicates the $K_D$, $K_{on}$, and $K_{off}$ values for human antibodies 1A1, 3A1, 3A2, and 3A3 and humanized antibodies 16H8, 3E2, 20C4, and 2E4, for both human SEZ6L2 and cynomolgus monkey SEZL2, as determined by ForteBio Data Analysis 9.0 Kinetics software. Briefly, within the ForteBio Octet red96 instrument, Protein A biosensors were incubated with fixed amounts of the test antibody. The biosensors with bound antibody were then rinsed and dipped into wells containing varying concentrations of the recombinant target protein. Approximately 5 different concentrations were independently tested. After a period of time, the biosensors were dipped into buffer to allow the target protein to dissociate from the antibody. The ForteBio software package generated a best-fit curve for each of the profiles of the varying concentrations of target protein. The calculated affinity measurements were analyzed, and the rate constant values from the middle of the linear range were chosen.

TABLE 10

Binding affinities for human and humanized SEZ6L2 antibodies.

| | Human SEZ6L2 | | | Cynomolgus monkey SEZ6L2 | | |
|---|---|---|---|---|---|---|
| Ab Name | KD | K(on) | K(off) | KD | K(on) | K(off) |
| 1A1 | 1 nM | 1.93E+06 | 1.25E−03 | 1 nM | 1.27E+06 | 1.60E−03 |
| 3A1 | 0.3 nM | 5.38E+05 | 1.37E−04 | 0.3 nM | 4.44E+05 | 1.41E−04 |
| 3A2 | 3 nM | 9.54E+05 | 2.58E−03 | 3 nM | 8.28E+05 | 2.52E−03 |
| 3A3 | 24 nM | 2.52E+06 | 6.02E−02 | 26 nM | 2.24E+06 | 5.88E−02 |
| 16H8 | 2 nM | 6.03E+05 | 2.20E−04 | | | |
| 3E2 | 2 nM | 1.33E+06 | 3.19E−03 | 2 nM | 1.37E+06 | 2.95E−03 |
| 20C4 | 3 nM | 6.35E+04 | 2.20E−04 | 3 nM | 1.05E+05 | 3.18E−04 |
| 2E4 | 7 nM | 2.05E+05 | 1.33E−03 | 12 nM | 1.63E+05 | 1.94E−03 |

Example 5

SEZ6L2 Antibodies Facilitate Delivery of Cytotoxic Agents to SEZ6L2-Expressing Small Cell Lung Tumor Cells In Vitro To demonstrate that the SEZ6L2 antibodies disclosed herein are able to mediate the delivery of a cytotoxic agent to live carcinoma cells, an in vitro cell killing assay was performed using selected SEZ6L2 antibody modulators bound to a saporin toxin. Saporin kills cells by deactivating ribosomes in the cytoplasm. Thus, cell death using the following assay indicates that the SEZ6L2 antibodies disclosed herein are able to internalize and deliver cytotoxic agents to the cytoplasm of a target cell.

An anti-Mouse or anti-Human IgG Fab fragment covalently linked to saporin ("Fab-Saporin; Advanced Targeting Systems, #IT-48 and #IT-51, respectively) was combined with unlabeled SEZ6L2 antibodies and incubated with human SCLC NCI-H524 cells expressing human SEZ6L2. The ability of the resulting saporin complexes to internalize and kill cells was measured 72 hours later by measuring cell viability.

Specifically, 5,000 NCI-H524 cells per well in RPMI supplemented with 10% fetal bovine serum were plated into 96 well tissue culture treated plates one day before the addition of antibodies and toxin. NCI-H524 cells expressing human SEZ6L2 were treated with a control (IgG1) or purified murine, humanized, or human SEZ6L2 antibodies at a concentration of 0.01 µg/ml and 0.4 µg/ml Fab-Saporin. The cells were cultured for 72 hours, after which viable cell numbers were enumerated using Cell Titer GloTM (Promega) as per manufacturer's instructions. Raw Luminescence Units (RLU) using cultures containing cells with the Saporin Fab fragment were set as 100% reference values and all other counts calculated accordingly (referred to as "percent viable cells").

FIGS. 1A-1B show that many of the SEZ6L2 antibodies tested mediated the killing of NCI-H524 cells. FIG. 1A shows murine antibodies 2E4, 3E2, 16H8, and 20C4; FIG. 1B shows human antibodies 1A1, 3A1, 3A2, 3A3, 3A4, 3B1, 3B2, 3B3, 3B6, and humanized antibodies 2E4, 3E2, 16H8, and 20C4. In FIG. 1A, a mouse IgG (mIgG) was used as a negative control and an anti-transferrin receptor antibody (TR) was used as a positive control. In FIG. 1B, a non-binding human antibody (3B5) was used as a negative control and a human antibody that demonstrated strong SEZ6L2 binding (antibody 1A1) was used as a positive control. These results demonstrate that internalization occurs upon binding of the SEZ6L2 specific antibody to the cell surface, without the need for additional crosslinking or dimerization.

Not only do these results demonstrate that exemplary SEZ6L2 antibodies described herein are able to bind SEZ6L2 antigen on the cell surface and facilitate the delivery of a cytotoxic payload resulting in cell death, but the above data also demonstrate that multiple anti-SEZ6L2 antibodies can mediate killing of SCLC tumor cells.

Example 6

Conjugated SEZ6L2 Antibodies Suppress Tumor Growth In Vivo

Given the results obtained with the murine, human and humanized anti-SEZ6L2 ADC antibodies, as described in Example 5, additional experiments were performed to demonstrate the efficacy of exemplary murine and humanized anti-SEZ6L2 ADC antibodies in treating SCLC tumors in vivo. A fully murine anti-SEZ6L2 antibody (antibody mu16H8) and the humanized descendant (antibody 16H8) were selected and conjugated to the tubulin inhibitor monomethyl auristatin E (MMAE), along with unconjugated humanized 16H8 (produced as set forth in Examples 2 and 3). Human IgG1 isotype control conjugated to MMAE (huIgG-MMAE) and PBS were included as control groups and administered to immunodeficient mice bearing SCLC cell-derived tumors.

Tumors derived from human SCLC cell line NCI-H524 were grown subcutaneously in the flanks of nude recipient mice using art-recognized techniques. Tumor volumes and mouse weights were monitored twice per week. When tumor volumes reached a mean of 250 mm$^3$, mice were randomly assigned to treatment groups of seven or eight mice and injected intraperitoneally with mu16H8-MMAE, 16H8-MMAE, 16H8 (naked), mIgG-MMAE, and PBS. Mice were given four injections of 5 mgs/kg over a period of 10 days. Following treatment, tumor volumes and mouse weights were monitored until tumors exceeded 1200 mm$^3$ or mice became sick.

The results of these experiments are presented in FIGS. 2A-2B. Durable reduction of tumor mass was achieved by the administration of the murine and the humanized anti-SEZ6L2 antibodies in NCI-H524 cell derived tumors (FIG. 2A). Absence of tumor growth was observed for more than 60 days in this study. Kaplan-Meier survival curves were also calculated and are shown in FIG. 2B. These results demonstrate that the SEZ6L2 antibodies disclosed herein are capable of effectively slowing or inhibiting the growth of small cell lung cancer tumors in vivo.

Example 7

Conjugation of Human Antibodies to Pyrrolobenzodiazepine (PBD)

Human monoclonal antibodies 3A1 and 1A1 and humanized antibody 3E2 were conjugated to pyrrolobenzodiazepine (PBD) as described by Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J. Briefly, each antibody was partially reduced with an appropriate molar amount of TCEP for 2 hours at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and hydrophobic interaction chromatography (HIC) respectively.

Example 8

In Vitro Killing Activity of SEZ6L2 Conjugated to PBD on SCLC and Prostate Cancer Cells The ADC's generated in Example 7 were tested to determine whether they were able to mediate toxin internalization and cell killing of human tumor cells in vitro. Human antibodies 3A1 and 1A1 and humanized antibody 3E2 conjugated to PBD were tested for their effect on small cell lung cancer and prostate cell line cells Small cell lung cancer cell lines H524, DMS79, and H209, and prostate adenocarcinoma cell lines 22Rv1 and LNCaP, all of which express SEZ6L2, and small cell lung cancer cell line H1048, which has less than 500 copies of SEZ6L2, were seeded onto 96 well plate at 1000-5000 cells/well.

Immediately after seeding the SCLC cell lines, 3E2-PBD, 3A1-PBD (or 1A1-PBD), and isotype control hIgG-PBD bearing a drug antibody ratio (DAR) of 1.7, 1.7, and 2.5 respectively, were added to the wells in complete culture medium so that the final Ab-PBD concentration in the well 0 to 6.7 nM (1 ug/ml). With NCI-H524 cells, 1A1-PBD, with a DAR of 1.7, was tested in lieu of 3A1-PBD. Each treatment was replicated in 2 wells. After six days, the modulator-mediated PBD cytotoxicity was assessed by quantifying the remaining number of live cells using Cell Titer Glo™ Cell viability was graphed by Prism™ using ratio of cell viability of test conditions to that of control wells treated with growth medium only. The conjugated antibodies 3E2-PBD, 3A1-PBD, and isotype control hIgG-PBD were tested and assessed under the same conditions in prostate cancer cell lines up to a final concentration of 67 nM (10 ug/ml).

When cells were treated with anti-SEZ6L2 ADCs, an increased reduction in percent viable cells were observed compared to the control hIgG in several cell lines (see FIG. 3A—NCI-H524; FIG. 3B—DMS79; FIG. 3C—NCI-H209; FIG. 3D—H1048; FIG. 3E—LNCaP; and FIG. 3F—22Rv1). While hIgG IgG-PBD can be cytotoxic to cells at high concentrations, the anti-SEZ6L2 ADCs tested were more potent, indicating an immunospecific response to SEZ6L2 rather than a general response to the PBD cytotoxin.

Example 9

Conjugated SEZ6L2 Modulators Suppress In Vivo Tumor Growth

Experiments were performed to demonstrate the efficacy of exemplary fully human or humanized anti-SEZ6L2 ADC modulators in treating SCLC tumors in vivo. Athymic mice bearing subcutaneous tumors were established from the small cell lung cancer cell line NCI-H524. Mice were randomized into four groups of seven or eight mice and treated by i.v. injection of reagents. One fully human anti-SEZ6L2 antibody (3A1), one humanized anti-SEZ6L2 antibody (3E2), and a non-binding isotype control (hIgG) were conjugated to the antimitotic agent monomethyl auristatin E (MMAE). The two test groups, isotype control, and vehicle alone were used to dose twice per week for two weeks at 5 mg/kg; tumor volumes were measured twice per week thereafter.

As set forth in FIG. 4A, this assay demonstrates that anti-SEZ6L2 antibodies conjugated to MMAE suppress NCI-H524 tumor growth in mice relative to vehicle or isotype control. A Kaplan-Meier survival curve was also generated from this study, which clearly shows an antigen specific increase survival (FIG. 4B). As before, mice treated with anti-SEZ6L2 did not exhibit adverse health effects beyond those typically seen in tumor bearing nude mice, with no discernable difference in body weight trends between test and control groups. These results indicate that antibodies against SEZ6L2 are useful as an ADC therapy for SCLC.

Example 10

Detection of SEZ6L2 Surface Expression and Specificity by Flow Cytometry

In order to assess whether SEZ6L2 antibody modulators immunospecifically associate with human SEZ6L2, and to determine whether the same modulators cross-react with SEZ6 and SEZ6L, flow cytometry was performed using a MACSquant™ as per the manufacturer's instructions. More particularly, modulators were tested for cross reactivity to cell lines that overexpress the human homologs of SEZ6 (293-SEZ6), SEZ6L (293-SEZ6L), and SEZ6L2 (293-SEZ6L2).

Briefly, staining for flow cytometry was performed in lx cold PBS with 0.5% BSA. Primary antibodies (1 ug/ml) were incubated with live cells on ice for one hour. After washing in the same buffer, cells were incubated with Alexa Fluro® 488-conjugated anti-human IgG secondary antibody @1:1000 (709-546-149, Jackson ImmunoResearch) on ice in the dark. After a 30 minute incubation, cells were washed in the same buffer and re-suspended in buffer plus propidium iodide (PI) to identify live cells. As a negative control, cells were incubated with secondary antibody alone. Acquisition of the data was performed on a MACSQuant® Flow Cytometer (Miltenyi Biotec) and analyzed with FlowJo software.

FIGS. 5A-M illustrate the results of the flow cytometry. The graphs on the right-hand side of FIGS. 5A-5L represent 293-SEZ6L2. The graphs on the left-hand side of FIGS. 5A-5L represent 293-SEZ6L and 293-SEZ6. FIGS. 5A-5L depict results for the following antibodies: 1A1 (FIG. 5A), 106 (FIG. 5B), 3A1 (FIG. 5C), 3A2 (FIG. 5D), 3A3 (FIG. 5E), 3B1 (FIG. 5F), 3B3 (FIG. 5G), 3B6 (FIG. 5H), 2E4: 4D2 (FIG. 5I), 3E2:7D4 (FIG. 5J), 16H8:A3F5 (FIG. 5K), and 20C4:red (FIG. 5L). FIG. 5M represents a control containing secondary antibody alone.

As demonstrated by FIGS. 5A-M, SEZ6L2 modulators recognize a cell line that overexpresses SEZ6L2 but have no detectable binding with the two other family members SEZ6L and SEZ6.

Example 11

An SEZL2 ADC Combined with a PARP Inhibitor Shows Enhanced Efficacy In Vitro Recent clinical studies suggest benefit in the use of cytotoxins combined with PARP inhibitors. Considering that publications have shown that PARP 1 and 2 transcript levels are highly expressed in SCLC relative to non-small cell lung cancer (NSCLC) cell lines, an SEZ6L2 ADC generated in Example 7 was tested to determine whether an additional reduction in cell viability would occur when combined with a PARP inhibitor. A humanized SEZ6L2 modulator conjugated to PBD (3E2-PBD) was tested in combination with a PARP inhibitor to determine if there was an additive effect on small cell lung cancer cell lines.

Briefly, the small cell lung cancer cell line NCI-H209, which expresses ~10,000 copies of SEZ6L2 on the cell surface, was seeded onto 96 well plate at 5000 cells/well Immediately after seeding, 10 pM of 3E2-PBD or isotype control hIgG-PBD (bearing a drug antibody ratio (DAR) of 1.7 and 2.5 respectively) were added to the wells in complete culture medium. A PARP inhibitor (olaparib) was then added to these wells such that the final concentration ranged from 10 nM to 10 uM. The PARP inhibitor was also tested on cells without an ADC. Each treatment was replicated in 2 wells and after six days, the PARP inhibitor plus modulator-mediated PBD cytotoxicity was assessed by quantifying the remaining number of live cells using Cell Titer Glo™. Cell viability was graphed by Prism™ using ratio of cell viability of test conditions to that of control wells treated with growth medium only.

As demonstrated in FIG. 6, NCI-209 cells that were treated with the PARP inhibitor alone responded in a dose dependent manner, as an increased reduction in percent viable cells were observed as the concentration of the inhibitor increased. Cells that were incubated with both the PARP inhibitor and SEZ6L2 ADC (10 pM) showed an increased reduction in viable cells, thereby demonstrating an additive effect. In contrast, there is no measureable difference in cell death when IgG-PBD (10 pM) is combined with the inhibitor, indicating an immunospecific response to SEZ6L2 rather than a general response to the PBD cytotoxin. This additive effect was also observed in the SEZ6L2 expressing SCLC cell lines DMS79, CORL279, and NCI-H524.

Sequence Summary

| SEQ ID NO: | Description |
|---|---|
| 1 | 16H8 VH amino acid sequence |
| 2 | 16H8, mu16H8 VH CDR1 amino acid sequence |
| 3 | 16H8 VH CDR2 amino acid sequence |
| 4 | 16H8, mu16H8 VH CDR3 amino acid sequence |
| 5 | 16H8 VL amino acid sequence |
| 6 | 16H8 VL CDR1 amino acid sequence |
| 7 | 16H8, mu16H8 VL CDR2 amino acid sequence |
| 8 | 16H8, mu16H8 VL CDR3 amino acid sequence |
| 9 | 3E2 VH amino acid sequence |
| 10 | 3E2, mu3E2 VH CDR1 amino acid sequence |
| 11 | 3E2, mu3E2 VH CDR2 amino acid sequence |
| 12 | 3E2, mu3E2 VH CDR3 amino acid sequence |
| 13 | 3E2 VL amino acid sequence |
| 14 | 3E2, mu3E2 VL CDR1 amino acid sequence |
| 15 | 3E2, mu3E2, 2E4, mu2E4 VL CDR2 amino acid sequence |
| 16 | 3E2, mu3E2 VL CDR3 amino acid sequence |
| 17 | 20C4 VH amino acid sequence |
| 18 | 20C4, mu20C4 VH CDR1 amino acid sequence |
| 19 | 20C4 VH CDR2 amino acid sequence |
| 20 | 20C4, mu20C4 VH CDR3 amino acid sequence |
| 21 | 20C4 VL amino acid sequence |
| 22 | 20C4, mu20C4 VL CDR1 amino acid sequence |
| 23 | 20C4, mu20C4 VL CDR2 amino acid sequence |
| 24 | 20C4, mu20C4 VL CDR3 amino acid sequence |
| 25 | 2E4 VH amino acid sequence |
| 26 | 2E4, mu2E4 VH CDR1 amino acid sequence |
| 27 | 2E4, mu2E4 VH CDR2 amino acid sequence |
| 28 | 2E4, mu2E4 VH CDR3 amino acid sequence |
| 29 | 2E4 VL amino acid sequence |
| 30 | 2E4, mu2E4 VL CDR1 amino acid sequence |
| 31 | 2E4, mu2E4 VL CDR3 amino acid sequence |
| 32 | 1A1, 1E4 VH amino acid sequence |
| 33 | 1A1, 1E4 VH CDR1 amino acid sequence |
| 34 | 1A1, 1E4 VH CDR2 amino acid sequence |
| 35 | 1A1, 1E4 VH CDR3 amino acid sequence |
| 36 | 1A1 VL amino acid sequence |
| 37 | 1A1, 3A4, 1C6, 1D5, 2M5_10A1 VL CDR1 amino acid sequence |
| 38 | 1A1, 1D2, 3A4, 1C6, 1D5, 2M5_10A1, 2M22_10A6 VL CDR2 amino |
| 39 | 1A1 VL CDR3 amino acid sequence |
| 40 | 1D2 VH amino acid sequence |
| 41 | 1D2 VH CDR1 amino acid sequence |
| 42 | 1D2 VH CDR2 amino acid sequence |
| 43 | 1D2 VH CDR3 amino acid sequence |
| 44 | 1D2 VL amino acid sequence |
| 45 | 1D2 VL CDR1 amino acid sequence |
| 46 | 1D2 VL CDR3 amino acid sequence |
| 47 | 1E4 VL amino acid sequence |
| 48 | 1E4, 3A2, 3A3 VL CDR1 amino acid sequence |
| 49 | 1E4, 3A2, 3A3 VL CDR2 amino acid sequence |
| 50 | 1E4 VL CDR3 amino acid sequence |
| 51 | 3A1 VH amino acid sequence |
| 52 | 3A1 VH CDR1 amino acid sequence |
| 53 | 3A1 VH CDR2 amino acid sequence |
| 54 | 3A1 VH CDR3 amino acid sequence |
| 55 | 3A1 VL amino acid sequence |
| 56 | 3A1 VL CDR1 amino acid sequence |
| 57 | 3A1, 3B6 VL CDR2 amino acid sequence |
| 58 | 3A1, 3B6 VL CDR3 amino acid sequence |
| 59 | 3B1 VH amino acid sequence |
| 60 | 3B1 VH CDR1 amino acid sequence |
| 61 | 3B1 VH CDR2 amino acid sequence |
| 62 | 3B1 VH CDR3 amino acid sequence |
| 63 | 3B1 VL amino acid sequence |
| 64 | 3B1, 3B3 VL CDR1 amino acid sequence |
| 65 | 3B1, 3B3 VL CDR2 amino acid sequence |
| 66 | 3B1 VL CDR3 amino acid sequence |
| 67 | 3B3 VH amino acid sequence |
| 68 | 3B3, 3B2 VH CDR1 amino acid sequence |
| 69 | 3B3, 3B2 VH CDR2 amino acid sequence |
| 70 | 3B3, 3B2 VH CDR3 amino acid sequence |
| 71 | 3B3 VL amino acid sequence |
| 72 | 3B3 VL CDR3 amino acid sequence |
| 73 | 3A2 VH amino acid sequence |
| 74 | 3A2 VH CDR1 amino acid sequence |
| 75 | 3A2, 3A3 VH CDR2 amino acid sequence |
| 76 | 3A2 VH CDR3 amino acid sequence |
| 77 | 3A2 VL amino acid sequence |
| 78 | 3A2 VL CDR3 amino acid sequence |
| 79 | 3A3 VH amino acid sequence |

-continued

| SEQ ID NO: | Description |
|---|---|
| 80 | 3A3 VH CDR1 amino acid sequence |
| 81 | 3A3 VH CDR3 amino acid sequence |
| 82 | 3A3 VL amino acid sequence |
| 83 | 3A3 VL CDR3 amino acid sequence |
| 84 | 3A4 VH amino acid sequence |
| 85 | 3A4 VH CDR1 amino acid sequence |
| 86 | 3A4 VH CDR2 amino acid sequence |
| 87 | 3A4 VH CDR3 amino acid sequence |
| 88 | 3A4 VL amino acid sequence |
| 89 | 3A4, 1D5 VL CDR3 amino acid sequence |
| 90 | 1C6 VH amino acid sequence |
| 91 | 1C6 VH CDR1 amino acid sequence |
| 92 | 1C6 VH CDR2 amino acid sequence |
| 93 | 1C6 VH CDR3 amino acid sequence |
| 94 | 1C6 VL amino acid sequence |
| 95 | 1C6 VL CDR3 amino acid sequence |
| 96 | 1C1 VH amino acid sequence |
| 97 | 1C1 VH CDR1 amino acid sequence |
| 98 | 1C1 VH CDR2 amino acid sequence |
| 99 | 1C1 VH CDR3 amino acid sequence |
| 100 | 1C1 VL amino acid sequence |
| 101 | 1C1 VL CDR1 amino acid sequence |
| 102 | 1C1 VL CDR2 amino acid sequence |
| 103 | 1C1 VL CDR3 amino acid sequence |
| 104 | 1D5 VH amino acid sequence |
| 105 | 1D5 VH CDR1 amino acid sequence |
| 106 | 1D5 VH CDR2 amino acid sequence |
| 107 | 1D5 VH CDR3 amino acid sequence |
| 108 | 1D5 VL amino acid sequence |
| 109 | 3B6 VH amino acid sequence |
| 110 | 3B6 VH CDR1 amino acid sequence |
| 111 | 3B6 VH CDR2 amino acid sequence |
| 112 | 3B6 VH CDR3 amino acid sequence |
| 113 | 3B6 VL amino acid sequence |
| 114 | 3B6 VL CDR1 amino acid sequence |
| 115 | 3B2 HV amino acid sequence |
| 116 | 3B2 HL amino acid sequence |
| 117 | 3B2 HL CDR1 amino acid sequence |
| 118 | 3B2 HL CDR1 amino acid sequence |
| 119 | 3B2 HL CDR1 amino acid sequence |
| 120 | 16H8 VH nucleic acid sequence |
| 121 | 3E2 VH nucleic acid sequence |
| 122 | 20C4 VH nucleic acid sequence |
| 123 | 2E4 VH nucleic acid sequence |
| 124 | 1A1 VH nucleic acid sequence |
| 125 | 1D2 VH nucleic acid sequence |
| 126 | 1E4 VH nucleic acid sequence |
| 127 | 3A1 VH nucleic acid sequence |
| 128 | 3B1 VH nucleic acid sequence |
| 129 | 3B3 VH nucleic acid sequence |
| 130 | 3A2 VH nucleic acid sequence |
| 131 | 3A3 VH nucleic acid sequence |
| 132 | 3A4 VH nucleic acid sequence |
| 133 | 1C6 VH nucleic acid sequence |
| 134 | 1C1 VH nucleic acid sequence |
| 135 | 1D5 VH nucleic acid sequence |
| 136 | 3B6 VH nucleic acid sequence |
| 137 | 3B2 VH nucleic acid sequence |
| 138 | 16H8 VL nucleic acid sequence |
| 139 | 3E2 VL nucleic acid sequence |
| 140 | 20C4 VL nucleic acid sequence |
| 141 | 2E4 VL nucleic acid sequence |
| 142 | 1A1 VL nucleic acid sequence |
| 143 | 1D2 VL nucleic acid sequence |
| 144 | 1E4 VL nucleic acid sequence |
| 145 | 3A1 VL nucleic acid sequence |
| 146 | 3B1 VL nucleic acid sequence |
| 147 | 3B3 VL nucleic acid sequence |
| 148 | 3A2 VL nucleic acid sequence |
| 149 | 3A3 VL nucleic acid sequence |
| 150 | 3A4 VL nucleic acid sequence |
| 151 | 1C6 VL nucleic acid sequence |
| 152 | 1C1 VL nucleic acid sequence |
| 153 | 1D5 VL nucleic acid sequence |
| 154 | 3B6 VL nucleic acid sequence |
| 155 | 3B2 VL nucleic acid sequence |

-continued

| SEQ ID NO: | Description |
|---|---|
| 156 | mu16H8 VH amino acid sequence |
| 157 | mu16H8 VH CDR2 amino acid sequence |
| 158 | mu16H8 VL amino acid sequence |
| 159 | mu16H8 VL CDR1 amino acid sequence |
| 160 | mu3E2 VH amino acid sequence |
| 161 | mu3E2 VL amino acid sequence |
| 162 | mu20C4 VH amino acid sequence |
| 163 | mu20C4 VH CDR2 amino acid sequence |
| 164 | mu20C4 VL amino acid sequence |
| 165 | mu2E4 VH amino acid sequence |
| 166 | mu2E4 VL amino acid sequence |
| 167 | Human SEZ6L2 amino acid sequence (with signal sequence) |
| 168 | Ig gamma-1 constant region |
| 169 | Ig gamma-1 constant region mutant |
| 170 | Ig kappa constant region |
| 171 | Ig lambda constant region |
| 172 | primer |
| 173 | primer |
| 174 | primer |
| 175 | primer |
| 176 | primer |
| 177 | primer |
| 178 | primer |
| 179 | primer |
| 180 | primer |
| 181 | primer |
| 182 | primer |
| 183 | primer |
| 184 | primer |
| 185 | primer |
| 186 | primer |
| 187 | primer |
| 188 | primer |
| 189 | primer |
| 190 | primer |
| 191 | primer |
| 192 | primer |
| 193 | primer |
| 194 | primer |
| 195 | primer |
| 196 | primer |
| 197 | primer |
| 198 | primer |
| 199 | primer |
| 200 | primer |
| 201 | primer |
| 202 | primer |
| 203 | primer |
| 204 | primer |
| 205 | primer |
| 206 | primer |
| 207 | primer |
| 208 | primer |
| 209 | primer |
| 210 | primer |
| 211 | primer |
| 212 | primer |
| 213 | primer |
| 214 | primer |
| 215 | primer |
| 216 | primer |
| 217 | primer |
| 218 | primer |
| 219 | primer |
| 220 | primer |
| 221 | primer |
| 222 | primer |
| 223 | primer |
| 224 | primer |
| 225 | primer |
| 226 | primer |
| 227 | primer |
| 228 | primer |
| 229 | primer |
| 230 | primer |
| 231 | primer |

| SEQ ID NO: | Description |
|---|---|
| 232 | primer |
| 233 | 2M5_10A1 VH amino acid sequence |
| 234 | 2M5_10A1 VH CDR1 amino acid sequence |
| 235 | 2M5_10A1 VH CDR2 amino acid sequence |
| 236 | 2M5_10A1 VH CDR3 amino acid sequence |
| 237 | 2M5_10A1 VL amino acid sequence |
| 238 | 2M5_10A1 VL CDR3 amino acid sequence |
| 239 | 2M22_10A6 VH amino acid sequence |
| 240 | 2M22_10A6 VH CDR1 amino acid sequence |
| 241 | 2M22_10A6 VH CDR2 amino acid sequence |
| 242 | 2M22_10A6 VH CDR3 amino acid sequence |
| 243 | 2M22_10A6 VL amino acid sequence |
| 244 | 2M22_10A6 VL CDR1 amino acid sequence |
| 245 | 2M22_10A6 VL CDR3 amino acid sequence |
| 246 | 2M5_10A1 VH nucleic acid sequence |
| 247 | 2M5_10A1 VL nucleic acid sequence |
| 248 | 2M22_10A6 VH nucleic acid sequence |
| 249 | 2M22_10A6 VL nucleic acid sequence |

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-human Seizure Related 6 Homolog Like 2 (anti-hSEZ6L2) antibody, or antigen binding portion thereof, wherein the antibody, or antigen binding portion thereof, comprises:

a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37.

2. The antibody, or antigen binding portion thereof, of claim 1, wherein the antibody, or antigen binding portion thereof, comprises:

a heavy chain variable region comprising the amino acid sequence of SEQ ID NO: 32 and a light chain variable region comprising the amino acid sequence of SEQ ID NO: 36.

3. The antibody, or antigen binding portion thereof, of claim 1, where in the antibody, or antigen binding portion thereof, comprises:

a heavy chain variable region comprising a sequence that is at least 85% identical to the amino acid sequence of SEQ ID NO: 32 and a light chain variable region comprising a sequence that is at least 85% identical to the amino acid sequence of SEQ ID NO: 36.

4. A pharmaceutical composition comprising the antibody, or antigen binding portion thereof, of claim 1.

* * * * *

SEQUENCE LISTING

```
<160> NUMBER OF SEQ ID NOS: 249

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Ile Gln Leu Val Gln Pro Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Tyr Trp Val Arg Gln Ala Pro Gly Gln Gly Leu Glu Trp Met
        35                  40                  45

Gly Ala Ile Tyr Pro Arg Asp Ser Asp Thr Ser Tyr Asn Gln Lys Phe
    50                  55                  60

Lys Gly Arg Val Thr Met Thr Arg Val Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Asp Tyr Tyr Tyr Gly Ser Ser Tyr Tyr Ala Met Asp Tyr
            100                 105                 110

Trp Gly Gln Gly Thr Thr Val Thr Val Ser Ser Ala
        115                 120

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Tyr Thr Phe Thr Ser Tyr Trp Met Tyr
1               5                   10

<210> SEQ ID NO 3
<211> LENGTH: 17
```

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Tyr Pro Arg Asp Ser Asp Thr Ser Tyr Asn Gln Lys Phe Lys
1               5                   10                  15

Gly

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Asp Tyr Tyr Tyr Gly Ser Ser Tyr Tyr Ala Met Asp Tyr
1               5                   10

<210> SEQ ID NO 5
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Val Met Thr Gln Ser Pro Leu Ser Leu Pro Val Thr Pro Gly
1               5                   10                  15

Glu Pro Ala Ser Ile Ser Cys Ser Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Met
                85                  90                  95

Leu Glu Arg Pro Tyr Thr Phe Gly Gln Gly Thr Lys Val Glu Ile Lys
            100                 105                 110

Arg

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Ser Lys Ser Leu Leu His Ser Asn Gly Ile Thr Tyr Leu Tyr
1               5                   10                  15

<210> SEQ ID NO 7
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 7

Arg Met Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Gln Met Leu Glu Arg Pro Tyr Thr
1               5

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ser Phe Asn Thr Ile
                20                  25                  30

Thr Met Asn Trp Val Arg Gln Ala Ser Gly Lys Gly Leu Glu Trp Val
            35                  40                  45

Gly Arg Ile Arg Ser Lys Ser Asn Asn Tyr Ala Thr Tyr Tyr Ala Asp
        50                  55                  60

Ala Val Lys Asp Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Val Arg Gly Ile Phe Ser Gly Tyr Val Tyr Ala Met Asp Tyr
            100                 105                 110

Trp Gly Gln Gly Thr Leu Val Thr Val Ser Ser Ala
        115                 120

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Ser Phe Asn Thr Ile Thr Met Asn
1               5                   10

<210> SEQ ID NO 11
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 11

Arg Ile Arg Ser Lys Ser Asn Asn Tyr Ala Thr Tyr Tyr Ala Asp Ala
1               5                   10                  15

Val Lys Asp

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ile Phe Ser Gly Tyr Val Tyr Ala Met Asp Tyr
1               5                   10

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Val Met Thr Gln Ser Pro Leu Ser Leu Pro Val Thr Val Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ser Gln Ser Ile Val His Ser Asn Gly Asn Thr Tyr Leu Glu
1               5                   10                  15

<210> SEQ ID NO 15
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 15

Lys Val Ser Asn Arg Phe Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Gln Gly Ser His Val Pro Tyr Thr
1               5

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Ala Leu Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asn Gly Leu Tyr Gly Leu Phe Ala Tyr Trp Gly Gln
            100                 105                 110

Gly Thr Leu Val Thr Val Ser Ser Ala
        115                 120

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Thr Asp Tyr Tyr Met Ser
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Arg Asn Lys Ala Asn Gly Tyr Thr Thr Glu Tyr Ser Ala Ser Val
1               5                   10                  15

Lys Gly

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asn Gly Leu Tyr Gly Leu Phe Ala Tyr
1               5

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Thr Pro Leu Ser Ile Pro Val Thr Pro Gly
1               5                   10                  15

Glu Pro Ala Ser Ile Ser Cys Arg Ser Ser Thr Ser Leu Leu Glu Ser
            20                  25                  30

Ser Gly Lys His Arg Leu Tyr Trp Tyr Leu Gln Lys Pro Gly Gln Ser
        35                  40                  45

Pro Gln Leu Leu Ile Tyr Tyr Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Ser
                85                  90                  95

Leu Glu Tyr Pro Leu Thr Phe Gly Ala Gly Thr Lys Val Glu Ile Lys
            100                 105                 110

Arg

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ser Ser Thr Ser Leu Leu Glu Ser Ser Gly Lys His Arg Leu Tyr
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 23

Tyr Met Ser Asn Leu Ala Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Ser Leu Glu Tyr Pro Leu Thr
1               5

<210> SEQ ID NO 25
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Lys Leu Val Glu Ser Gly Gly Val Leu Val Lys Pro Gly Gly
1               5                   10                  15

Ser Leu Arg Leu Ser Cys Ala Ala Ser Gly Phe Thr Phe Ser Lys Tyr
            20                  25                  30

Ala Met Ser Trp Val Arg Gln Ala Pro Gly Lys Gly Leu Glu Trp Val
        35                  40                  45

Ser Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Ile Tyr Tyr Cys
                85                  90                  95

Thr Arg Glu Gly Gly Tyr Asp Glu Gly Tyr Ala Met Asp Tyr Trp Gly
            100                 105                 110

Gln Gly Thr Thr Val Thr Val Ser Ser Ala
        115                 120

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Thr Phe Ser Lys Tyr Ala Met Ser
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 27

Thr Ile Ser Ser Gly Gly Ser Tyr Thr Tyr Tyr Pro Asp Ser Val Lys
1               5                   10                  15

Gly

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Gly Gly Tyr Asp Glu Gly Tyr Ala Met Asp Tyr
1               5                   10

<210> SEQ ID NO 29
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Val His Ser
            20                  25                  30

Tyr Gly Asn Thr Tyr Leu His Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Phe Cys Ser Gln Ser
                85                  90                  95

Thr His Phe Arg Thr Phe Gly Gly Gly Thr Lys Val Glu Ile Lys Arg
            100                 105                 110

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ser Ser Gln Ser Leu Val His Ser Tyr Gly Asn Thr Tyr Leu His
1               5                   10                  15

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Gln Ser Thr His Phe Arg Thr
1               5

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Phe Trp Val Arg Gln Ala Pro Gly Gln Gly Leu Glu Trp Leu
        35                  40                  45

Gly Trp Ile Asn Pro Asn Ser Gly Gly Thr Asp Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Gly Tyr Asp Trp Phe Phe Asp Tyr Trp Gly Gln Gly
            100                 105                 110

Thr Leu Val Thr Val Ser Ser
        115

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Tyr Thr Phe Thr Gly Tyr Tyr Met Phe
1               5                   10

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Ile Asn Pro Asn Ser Gly Gly Thr Asp Tyr Ala Gln Lys Phe Gln
1               5                   10                  15

Gly

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Asp Ser Gly Tyr Asp Trp Phe Phe Asp Tyr
1               5                   10

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Thr Phe Gly Pro Gly Thr Lys Leu Glu Ile Lys
            100                 105

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Ser Gln Ser Val Ser Ser Asn Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ala Ser Thr Arg Ala Thr
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Tyr Asn Asn Trp Pro Pro Phe Thr
1               5                   10

```
<210> SEQ ID NO 40
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Asp Gln Asn Ser Gly Trp Leu Phe Asp Tyr Trp Gly Gln Gly
            100                 105                 110

Thr Leu Val Thr Val Ser Ser
        115

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Thr Phe Thr Gly Tyr Tyr Met His
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Ile Asn Pro Asn Asn Gly Gly Thr Asn Tyr Ala Gln Lys Phe Gln
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Gln Asn Ser Gly Trp Leu Phe Asp Tyr
1               5                   10
```

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Ser Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ile Thr Phe Gly Gln Gly Thr Arg Leu Glu Ile Lys
            100                 105

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Ala Ser Gln Ser Val Ser Ser Asn Ser Ala
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Tyr Asn Asn Trp Pro Pro Ile Thr
1               5                   10

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

```
Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Val Glu Ile Lys
            100                 105
```

```
<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Ser Ile Ser Ser Trp Leu Ala
1               5                   10
```

```
<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ala Ser Ser Leu Glu Ser
1               5
```

```
<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Tyr Asn Ser Tyr Ser Tyr Thr
1               5
```

```
<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Thr Gly Tyr
            20                  25                  30

Tyr Ile Leu Trp Met Arg Gln Ala Pro Gly Gln Gly Leu Glu Trp Met
            35                  40                  45
```

```
Gly Trp Ile Asn Pro Asn Asn Gly Gly Thr His Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Gly His Asp Trp Tyr Phe Asp Leu Trp Gly Arg Gly
            100                 105                 110

Thr Leu Val Thr Val Ser Ser Ala
        115                 120

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Phe Thr Phe Thr Gly Tyr Tyr Ile Leu
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Ile Asn Pro Asn Asn Gly Gly Thr His Tyr Ala Gln Lys Phe Gln
1               5                   10                  15

Gly

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ser Gly His Asp Trp Tyr Phe Asp Leu
1               5                   10

<210> SEQ ID NO 55
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln His Ser Asn Trp Pro Pro
                 85                  90                  95

Leu Thr Phe Gly Gly Gly Thr Lys Val Glu Ile Lys Arg
            100                 105

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ala Ser Gln Ser Val Ser Ser Ser Leu Ala
 1               5                  10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ala Ser Asn Arg Ala Thr
 1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gln His Ser Asn Trp Pro Pro Leu Thr
 1               5                  10

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Ser Gly Gly Gly Val Val Gln Pro Gly Arg
 1               5                  10                  15

Ser Leu Arg Leu Thr Cys Val Ser Gly Phe Ala Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Asp Tyr Tyr Gly Ser Gly Ser Arg Phe Asp Pro Trp Gly
            100                 105                 110

Gln Gly Thr Leu Val Thr Val Ser Ser Ala
        115                 120

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Phe Ala Phe Ser Ser Tyr Gly Met His
1               5                   10

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Ile Trp Tyr Asp Gly Ser Asn Lys Tyr Tyr Ala Asp Ser Val Lys
1               5                   10                  15

Gly

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Asp Tyr Tyr Gly Ser Gly Ser Arg Phe Asp Pro
1               5                   10

<210> SEQ ID NO 63
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 64
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Ser Gln Ser Leu Leu His Ser Asn Gly Tyr Asn Tyr Leu Asp
1               5                   10                  15

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Gly Ser Asn Arg Ala Ser
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Gln Ala Leu Gln Thr Pro Tyr Thr
1               5

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Gly Ser Tyr Ala Phe Asp Tyr Trp Gly Gln Gly Thr
            100                 105                 110

Leu Val Thr Val Ser Ser Ala
        115

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Ser Ser Tyr Trp Met Ser
1               5                   10

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Asn Ile Lys Gln Asp Gly Ser Glu Lys Tyr Tyr Val Asp Ser Val Lys
1               5                   10                  15

Gly

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Gly Gly Ser Tyr Ala Phe Asp Tyr
1               5

<210> SEQ ID NO 71
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

-continued

```
Ser Arg Val Glu Ala Glu Asp Val Gly Val Tyr Tyr Cys Met Gln Ala
            85                  90                  95

Leu Gln Thr Pro Arg Thr Phe Gly Gln Gly Thr Lys Val Glu Ile Lys
        100                 105                 110

Arg

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Met Gln Ala Leu Gln Thr Pro Arg Thr
1               5

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Tyr
            20                  25                  30

His Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Gly Arg Ile Ala Val Ala Asp Tyr Trp Gly Gln Gly Thr
            100                 105                 110

Leu Val Thr Val Ser Ser Ala
        115

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Gly Ser Ile Ser Ser Tyr His Trp Trp Ser
1               5                   10

<210> SEQ ID NO 75
<211> LENGTH: 16
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 75

Glu Ile Tyr His Ser Gly Ser Thr Asn Tyr Asn Pro Ser Leu Lys Ser
1               5                   10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Trp Gly Arg Ile Ala Val Ala Asp Tyr
1               5

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys Arg
            100                 105

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Gln Tyr Asn Ser Tyr Trp Thr
1               5

<210> SEQ ID NO 79
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 79

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ala Tyr Ser Gly Ser Tyr Phe Glu Tyr Trp Gly Gln Gly Thr Leu
            100                 105                 110

Val Thr Val Ser Ser Ala
        115

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gly Ser Ile Ser Ser Ser Asn Trp Trp Ser
1               5                   10

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Ser Gly Ser Tyr Phe Glu Tyr
1               5

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Pro Leu
                 85                  90                  95

Thr Phe Gly Gly Gly Thr Lys Leu Glu Ile Lys Arg
                100                 105

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gln Gln Tyr Asn Ser Tyr Pro Leu Thr
 1               5

<210> SEQ ID NO 84
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Phe Tyr Ser Gly Ser Thr Asn Tyr Asn Pro Ser Leu Lys
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Ser Ser Gly Trp Tyr Gly Val Asp Tyr Trp Gly Gln Gly
                100                 105                 110

Thr Leu Val Thr Val Ser Ser
        115

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Asp Ser Ile Ser Ser Tyr Tyr Trp Ser
 1               5                  10

<210> SEQ ID NO 86
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 86

Tyr Ile Phe Tyr Ser Gly Ser Thr Asn Tyr Asn Pro Ser Leu Lys Ser
1               5                   10                  15

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Ser Ser Gly
1

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys
            100                 105

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gln Gln Tyr Asn Asn Trp Pro Leu Thr
1               5

<210> SEQ ID NO 90
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 90

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Asn Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Asp Gln Gly Tyr Trp Tyr Phe Asp Leu Trp Gly Arg Gly
            100                 105                 110

Thr Leu Val Thr Val Ser Ser
        115

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Gly Ser Ile Ser Ser Tyr Tyr Trp Ser
1               5                   10

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Tyr Ile Tyr Asn Ser Gly Ser Thr Asn Tyr Asn Pro Ser Leu Lys Ser
1               5                   10                  15

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Gly Asp Gln Gly Tyr Trp Tyr Phe Asp Leu
1               5                   10

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Thr Phe Gly Gln Gly Thr Lys Val Glu Ile Lys
            100                 105

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Asn Asn Trp Pro Pro Thr
1               5

<210> SEQ ID NO 96
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Glu Ile Asn His Gly Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Tyr Phe Asp Trp Leu Phe Pro Ala Phe Asp Ile Trp Gly
            100                 105                 110

Gln Gly Thr Met Val Thr Val Ser Ser
        115                 120

<210> SEQ ID NO 97
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 97

Gly Gly Ser Phe Ser Ala Tyr Tyr Trp Ser
1               5                   10

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Ile Asn His Gly Gly Ser Thr Asn Tyr Asn Pro Ser Leu Lys Ser
1               5                   10                  15

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Arg Tyr Phe Asp Trp Leu Phe Pro Ala Phe Asp Ile
1               5                   10

<210> SEQ ID NO 100
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Glu Ile Lys
            100                 105

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ala Ser Gln Gly Ile Ser Ser Tyr Leu Ala
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ala Ala Ser Thr Leu Gln Ser
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Gln Leu Asn Ser Tyr Pro Phe Thr
1               5

<210> SEQ ID NO 104
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Tyr
            20                  25                  30

Tyr Trp Ser Trp Ile Arg Gln Pro Pro Gly Lys Gly Leu Glu Trp Ile
        35                  40                  45

Gly Tyr Ile His Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Tyr Asn Ser Gly Trp Leu Phe Asp Tyr Trp Gly Gln Gly
            100                 105                 110

Thr Leu Val Thr Val Ser Ser
        115

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 105

Gly Gly Ser Ile Arg Ser Tyr Tyr Trp Ser
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Tyr Ile His Tyr Ser Gly Ser Thr Asn Tyr Asn Pro Ser Leu Lys Ser
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Ser Tyr Asn Ser Gly Trp Leu Phe Asp Tyr
1               5                   10

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys
            100                 105

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ala Tyr
             20                  25                  30

Tyr Met His Trp Val Arg Gln Ala Pro Gly Gln Gly Leu Glu Trp Met
         35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Asp Thr Ala Tyr
 65                  70                  75                  80

Leu Asp Leu Ser Arg Leu Arg Ser Asp Thr Ala Val Tyr Tyr Cys
                 85                  90                  95

Ala Lys Asp Ser Gly Tyr Asp Trp Tyr Phe Asp Ile Trp Gly Arg Gly
             100                 105                 110

Thr Leu Val Thr Val Ser Ser Ala
        115                 120

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Tyr Thr Phe Thr Ala Tyr Tyr Met His
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Trp Ile Asn Pro Asn Ser Gly Gly Thr Asn Tyr Ala Gln Lys Phe Gln
1               5                   10                  15

Gly

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Ser Gly Tyr Asp Trp Tyr Phe Asp Ile
1               5                   10

<210> SEQ ID NO 113
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Asn Ile Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Phe Tyr Cys Gln Gln His Ser Asn Trp Pro Pro
                85                  90                  95

Leu Thr Phe Gly Gly Gly Thr Lys Val Glu Ile Lys Arg
            100                 105
```

```
<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Asn Ile Ser Ser Tyr Leu Ala
1               5                   10
```

```
<210> SEQ ID NO 115
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Tyr Ala Phe Asp Tyr Trp Gly Gln Gly Thr
            100                 105                 110

Leu Val Thr Val Ser Ser
        115
```

```
<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 116

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Leu Thr Phe Gly Gly Gly Thr Lys Val Glu Ile
            100                 105                 110

Lys

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Ser Ser Gln Ser Leu Val Tyr Ser Asp Gly Asn Thr Tyr Leu Asn
1               5                   10                  15

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Val Ser Asn Arg Asp Ser
1               5

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Met Gln Gly Thr His Trp Pro Pro Leu Thr
1               5                   10

<210> SEQ ID NO 120
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120

```
caaatacaat tggtgcaacc tggtgccgaa gttaagaagc ccggggcaag tgtgaaagtt      60
tcttgtaagg catccgggta taccttcaca agttattgga tgtactgggt tcggcaggcc     120
ccaggtcagg gcctggaatg gatgggtgct atctatccac gcgatagcga taccagctac     180
aatcagaaat ttaagggtcg agtgactatg acacgggtga ctagtacctc tacggtttac     240
atggagttgt cctccctgag atctgaggac actgctgtat attactgcac acgggggggac     300
tattactacg gtagctcata ttatgccatg gattactggg ccaggggac gacagtaaca      360
gtatcatca                                                             369
```

<210> SEQ ID NO 121
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121

```
gaagttcaac tcgttgagtc tggtggaggc ttggtgcaac caggaggaag tctgaagctg      60
tcatgtgccg cctctggttt ctcatttaat acgataacca tgaactgggt gcgacaggct     120
agtggtaagg gactcgagtg ggtaggcaga atcagatcaa aatctaacaa ttatgcgact     180
tattatgcgg acgctgtaaa agatcggttt accataagcc gcgacgattc taaaaataca     240
gcgtaccttc aaatgaatag tctcaagacg gaggatacgg ctgtctacta ttgtgtgcgg     300
ggcatcttca gcggttacgt gtacgctatg gattattggg ggcaagggac gcttgtaact     360
gtgtcttca                                                             369
```

<210> SEQ ID NO 122
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 122

```
gaggttcagc ttgtggagtc tggaggcggt ctcgtgcaac caggcggttc ccttcgcctt      60
tcatgcgctg ccagcgggtt cactttcacc gactactata tgagctgggt gcggcaagcg     120
ccaggaaagg gcctggaatg ggttgctctg atacgaaata aggcaaacgg ctacacgact     180
gagtattccg cgtctgtaaa aggcaggttt actatatccc gagacaactc aaagaactcc     240
ttgtatctcc agatgaatag tctgcgagcg gaggacactg ccgtatatta ctgcgcaaga     300
aacggcctgt atggactttt tgcatactgg gggcaaggca cacttgtcac tgtgtcaagt     360
```

<210> SEQ ID NO 123
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123

```
gaagttaaac tcgtagagtc aggtggcgtg ctcgtaaaac ctggtggctc ccttcgcctt      60
agttgtgccg ccagtgggtt taccttttagc aagtacgcaa tgagttgggt tcggcaagcg    120
```

```
ccgggtaagg gactcgaatg ggtatctacg ataagtagcg gtggttccta tacttattac    180
ccagactccg taaaaggtag gttcactata tcacgagaca atgcgagaaa ctcattgtac    240
ctccaaatga atagcttgcg ggcagaagat actgcgatat attactgtac tcgggaaggg    300
ggatatgacg aaggctatgc gatggactat tggggccagg gacgactgt tactgtaagc     360 tct                                                                  363
```

```
<210> SEQ ID NO 124
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
caggtgcagc tggtgcagtc tggggctgag gtgaagaagc ctggggcctc agtgaaggtc     60
tcctgcaagg cttctggata caccttcacc ggctactata tgttctgggt gcgacaggcc    120
cctggacaag gcttgagtg gctgggatgg atcaaccta acagtggtgg cacagactat     180
gcacagaagt tcagggcag ggtcaccatg accaggaca cgtccatcag cacagcctac      240
atggagctga gcaggctgag atctgacgac acggccgtgt attactgtgc gagagatagt    300
ggctacgatt ggttctttga ctactggggc cagggaaccc tggtcaccgt ctcctca       357
```

```
<210> SEQ ID NO 125
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaaccta acaatggtgg cacaaactat      180
gcacagaagt tcagggcag ggtcaccatg accaggaca cgtccatcag cacagcctac      240
atggagctgc gcaggctgag atctgacgac acggccgtgt attactgtgc gagagatcag    300
aacagtggct ggcttttga ctactggggc cagggcaccc tggtcaccgt ctcctca        357
```

```
<210> SEQ ID NO 126
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
caggtgcagc tggtgcagtc tggggctgag gtgaagaagc ctggggcctc agtgaaggtc     60
tcctgcaagg cttctggata caccttcacc ggctactata tgttctgggt gcgacaggcc    120
cctggacaag gcttgagtg gctgggatgg atcaaccta acagtggtgg cacagactat     180
gcacagaagt tcagggcag ggtcaccatg accaggaca cgtccatcag cacagcctac      240
atggagctga gcaggctgag atctgacgac acggccgtgt attactgtgc gagagatagt    300
ggctacgatt ggttctttga ctactggggc cagggaaccc tggtcaccgt ctcctca       357
```

<210> SEQ ID NO 127
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127
caggtgcagc tggtgcagtc tggggctgag gtgaagaagc ctggggcctc agtgaaggtc      60
tcctgcaagg cttctggatt caccttcacc ggctactata tcctctggat gcgacaggcc     120
cctggacaag gacttgagtg gatgggatgg atcaaccctc acaatggtgg cacacactat     180
gcacagaagt ttcagggcag ggtcaccatg accagggaca cgtccattag cacagcctac     240
atggaactga gcaggctgag atctgacgac acggccgtgt attactgtgc gagagatagt     300
ggccacgact ggtacttcga tctctggggc cgtggcaccc tggtcaccgt ctcctca       357

<210> SEQ ID NO 128
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
caggtgcagt tggtggagtc tgggggaggc gtggtccagc ctgggaggtc cctgagactc      60
acctgtgtag tgtctggatt cgccttcagt agctatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagcctagat     300
tactatggtt cggggagccg gttcgacccc tggggccagg gaaccctggt caccgtctcc     360
tca                                                                   363

<210> SEQ ID NO 129
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
gaggtgcagc tggtggagtc tgggggaggc ttggtccagc ctgggggtc cctgagactc      60 tcctgtgcag cctctggatt cacctttagt agctattgga tgagctgggt ccgccaggct     120
ccagggaagg ggctggagtg ggtggccaac ataaagcaag atggaagtga gaaatactat     180
gtggactctg tgaagggccg attcaccatc tccagagaca acgccaagaa ctcactgtat     240
ctgcaaatga acagcctgag agccgaggac acggctgtgt attactgtgc gagaggggga     300
gggagctacg cctttgacta ctggggccag ggaaccctgg tcaccgtctc ctca           354

<210> SEQ ID NO 130
<211> LENGTH: 354
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 130

```
caggtgcagc tgcaggagtc gggcccagga ctggtgaagc cttcggggac cctgtccctc    60
acctgcgctg tctctggtgg ctccatcagc agttatcact ggtggagttg ggtccgccag   120
cccccaggga aggggctgga atggattggg gaaatctatc atagtgggag caccaactac   180
aacccgtccc tcaagagtcg agtcaccata tcagtagaca agtccaagaa ccagttctcc   240
ctgaagctga gctctgtgac cgccgcggac acggccgtgt attactgtgc gagatggggc   300
cgtatagcag tggctgacta ctggggccag ggaaccctgg tcaccgtctc ctca         354
```

<210> SEQ ID NO 131
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131

```
caggtgcagc tgcaggagtc gggcccagga ctggtgaagc cttcgggac cctgtccctc     60 acctgcgctg tctctggtgg ctccatcagc agtagtaact ggtggagttg ggtccgccag   120
cccccaggga aggggctgga gtggattggg gaaatctatc atagtgggag caccaactac   180
aacccgtccc tcaagagtcg agtcaccata tcagtagaca agtccaagaa ccagttctcc   240
ctgaagctga gctctgtgac cgccgcggac acggccgtgt attactgtgc ggcctatagt   300
gggagctact ttgagtactg gggccaggga accctggtca ccgtctcctc a            351
```

<210> SEQ ID NO 132
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
caggtgcagc tgcaggagtc gggcccagga ctggtgaagc cttcggagac cctgtccctc    60
acctgcactg tctctggtga ctccatcagt agttactact ggagctggat ccggcagccc   120
ccagggaagg gactggagtg gattgggtat atctttaca gtgggagcac caactacaac    180
ccctccctca agagtcgagt caccatatca gtagacacg ccaagaacca gttctccctg    240
aagctgagct ctgtgaccgc tgcggacacg gccgtgtatt actgtgcgag agatagcagt   300
ggctggtacg gggggttga ctactggggc caggaaccc tggtcaccgt ctcctca        357
```

<210> SEQ ID NO 133
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctataaca gtgggagcac caactacaac   180
```

```
ccctccctca agagtcgagt caccatatca gtagacacgt ccaagaacca gttctccctg    240
aagctgagct ctgtgaccgc tgcggacacg gccgtatatt actgtgcgag acgggggggat   300 cagggttact ggtacttcga tctctggggc cgtggcaccc tggtcaccgt ctcctca      357
```

```
<210> SEQ ID NO 134
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
caggtgcagc tacagcagtg gggcgcagga ctgttgaagc cttcggagac cctgtccctc    60
acctgcgctg tctatggtgg gtccttcagt gcttactact ggagctggat ccgccagccc   120
ccagggaagg ggctggagtg gattggggaa atcaatcatg gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag aggacgatat   300
tttgactggt tattccctgc ttttgatatc tggggccaag gacaatggtc accgtctcc    360 tca                                                                 363
```

```
<210> SEQ ID NO 135
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135
caggtgcagc tgcaggagtc gggcccagga ctggtgaagc cttcggagac cctgtccctc    60
acctgcactg tctctggtgg ctccatcagg agttactact ggagctggat ccggcagccc   120
ccagggaagg gactggagtg gattgggtat atccattaca gtgggagcac caactacaac   180
ccctccctca agagtcgagt caccatatca gtagacacgt ccaagaacca gttctccctg   240
aagctgagct ctgtgaccgc tgcggacacg gccgtgtatt actgtgcgag agggtcgtat   300
aacagtggct ggcttttttga ctactggggc cagggaaccc tggtcaccgt ctcctca     357
```

```
<210> SEQ ID NO 136
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
caggtgcagc tggtgcagtc tggggctgag gtgaagaagc ctggggcctc agtgaaggtc    60
tcctgcaagg cttctggata caccttcacc gcctactata tgcactgggt gcgacaggcc   120
cctggacaag gcttgagtg gatgggatgg atcaaccctaa acagtggtgg cacaaactat   180
gcacagaagt ttcagggcag ggtcaccatg accagggaca cgtccatcga cacagcctat   240
ttggatctga gcaggctgag atctgacgac acggccgttt attactgtgc gaaagatagt   300
ggctacgact ggtacttcga tatctggggc cgtggcaccc tggtcaccgt ctcctca      357
```

<210> SEQ ID NO 137
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gaggtgcagc tggtggagtc tgggggaggc ttggtccagc ctgggggtc cctgagactc        60 tcctgtgcag cctctggatt cacctttagt agctattgga tgagctgggt ccgccaggct       120
ccagggaagg gctggagtg gtggccaac ataaagcaag atggaagtga gaaatactat        180
gtggactctg tgaagggccg attcaccatc tccagagaca cgccaagaa ctcactgtat       240 ctgcaaatga acagcctgag agccgaggac acggctgtgt attactgtgc gagaggggga       300
gggagctacg cctttgacta ctggggccag ggaaccctgg tcaccgtctc ctca             354

<210> SEQ ID NO 138
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gacattgtga tgactcagtc tccactgagc ctgccagtca ccccaggtga acccgcatcc       60
atctcctgct ctagtagcaa aagtttgctc catagcaatg gcatcactta cctttactgg       120
tacctccaga agccaggcca agcccgcaa ctccttatat atagaatgag taacttggcc       180
tccggcgtac ccgataggtt ctcaggatct ggctctggga ctgatttcac actgaaaata       240
tctagagttg aagccgagga cgtgggtgtg tactattgtg ctcagatgtt ggaaaggccg       300
tatacattcg gacaggggac caaggttgaa atcaaa                                336

<210> SEQ ID NO 139
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 139
gatgtggtga tgactcaaag tccgctgagc ttgcccgtta cggttggtca gccagccagc       60
atcagctgtc gaagttctca atctatcgtc cacagcaacg gaatacata cttggaatgg       120 tttcagcaaa ggccggggca atctccccgc gtgcttatct acaaggtctc taaccgattc       180
agtggagttc cagaccgctt cagcggctcc ggtcaggta cagattttac tctcaagatt       240
tctcgggtcg aagctgagga tgtaggggtc tattattgtt tccaaggctc acacgtgccc       300
tacacgttcg ggggcggaac caaactcgag ataaag                                336

<210> SEQ ID NO 140
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140

```
gacatcgtga tgactcagac tcccttgagt attcctgtaa ccccgggcga accggcctca      60
ataagttgca ggtcatcaac gtctttgctt gaatccagtg gtaaacatcg gttgtactgg     120
tatctccaga aaccagggca atctccgcag ttgcttatct actacatgtc aaatctggcg     180
tctggcgtcc cagacagatt cagcggaagc ggtagcggaa ctgatttac  tttgaaaata     240
tcacggggttg aggccgaaga cttttggggtc tactattgta tgcagagtct tgaatatcca   300
ctcacgttcg gtgctgggac taaagtcgaa ataaaa                                336
```

<210> SEQ ID NO 141
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 141

```
gacatcgtta tgacgcaatc accggattcc ttggcagtaa gtcttgggga gagagcaacc      60
ataaattgta ggagtagtca gagtttggtt cattcctatg gtaatacata ccttcactgg    120
taccagcaaa aacctggaca gccgccaaaa ctcctgatat acaaggtttc aaacaggttt    180
agtggtgtgc ccgacaggtt tagtggttct ggatctggca ccgatttcac ccttacgata    240
tctagcctcc aggctgaaga tgtggcagtc tattttgta  gccaatcaac ccatttcaga    300
acattcggtg gcggaacgaa ggttgaaatc aag                                  333
```

<210> SEQ ID NO 142
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctccatt cacttttcggc   300
cctgggacca agctggagat caaa                                            324
```

<210> SEQ ID NO 143
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143

```
gaaatagtga tgacgcagtc tccagccacc ctgtctgtgt ctccagggga aagagccacc      60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
```

```
gaagattttg cagtttatta ctgtcagcag tataataact ggcctcccat caccttcggc    300
caagggacac gactggagat taaa                                          324

<210> SEQ ID NO 144
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtacac ttttggccag    300
gggaccaagg tggagatcaa a                                             321

<210> SEQ ID NO 145
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gaaattgtgt tgacacagtc tccagccacc ctgtctttgt ctccagggga aagagccacc     60
ctctcctgca gggccagtca gagtgttagc agctccttag cctggtacca gcagaaacct    120
ggccaggctc ccaggctcct catctatgat gcctccaaca gggccactgg catcccagcc    180
aggttcagtg gcagtgggtc tgggacagac ttcactctca ccatcagcag cctagagcct    240
gaagattttg cagtttatta ctgtcagcag catagcaact ggcctccgct cactttcggc    300
ggagggacca aggtggagat caaa                                          324

<210> SEQ ID NO 146
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
gatattgtga tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttttac actgaaaatc    240 agcagagtgg aggctgagga tgttggggtt tattactgca tgcaagctct acaaactccg    300
tacacttttg gccaggggac caagctggag atcaaa                             336

<210> SEQ ID NO 147
<211> LENGTH: 336
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 147
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgattt atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
cggacgttcg gccaagggac caaggtggag atcaaa                              336

<210> SEQ ID NO 148
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attggacgtt cggccaaggg    300
accaaggtgg agatcaaa                                                  318

<210> SEQ ID NO 149
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt atcctctcac tttcggcgga    300
gggaccaagc tggagatcaa a                                              321

<210> SEQ ID NO 150
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gaaatagtga tgacgcagtc tccagccacc ctgtctgtgt ctccagggga aagagccacc      60
ctctcctgca gggccagtca gagtgttagc agcaacttag cctggtacca gcagaaacct    120
```

```
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga    300
gggaccaagg tggagatcaa a                                              321

<210> SEQ ID NO 151
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151
gaaatagtga tgacgcagtc tccagccacc ctgtctgtgt ctccagggga aagagccacc    60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctccgac gttcggccaa    300
gggaccaagg tggagatcaa a                                              321

<210> SEQ ID NO 152
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 152
gacatccagt tgacccagtc tccatccttc ctgtctgcat ctgtaggaga cagagtcacc    60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag cttaatagtt acccattcac tttcggccct    300
gggaccaagg tggagatcaa a                                              321

<210> SEQ ID NO 153
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gaaatagtga tgacgcagtc tccagccacc ctgtctgtgt ctccagggga aagagccacc    60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tataataact ggcctctcac tttcggcgga    300
gggaccaagc tggagatcaa a                                              321

<210> SEQ ID NO 154
```

<210> SEQ ID NO 154
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 154

```
gaaattgtgt tgacacagtc tccagccacc ctgtctttgt ctccagggga aagagccacc    60
ctctcctgca gggccagtca gaatattagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagttttta ctgtcagcag catagcaact ggcctccgct cactttcggc   300
gggggaccaa aggtggagat caaa                                          324
```

<210> SEQ ID NO 155
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 155

```
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctaattt ataaggtttc taaccgggac   180
tctggggtcc cagacagatt cagcggcagt gggtcaggca ctgatttcac actgaaaatc   240
agcagggtgg aggctgagga tgttggggtt tattactgca tgcaaggtac acactggcct   300
ccgctcactt tcggcggagg gaccaaggtg gagatcaaa                          339
```

<210> SEQ ID NO 156
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

```
Gln Ile Gln Leu Gln Gln Pro Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met Tyr Trp Val Lys Gln Arg Pro Gly Gln Gly Leu Glu Trp Ile
        35                  40                  45

Gly Ala Ile Tyr Pro Arg Asp Ser Asp Thr Ser Tyr Asn Gln Lys Phe
    50                  55                  60

Lys Gly Lys Ala Lys Leu Thr Ala Val Thr Ser Ala Ser Thr Ala Tyr
65                  70                  75                  80

Met Glu Leu Ser Ser Leu Thr Asn Glu Asp Ser Ala Val Tyr Tyr Cys
                85                  90                  95

Thr Arg Gly Asp Tyr Tyr Tyr Gly Ser Ser Tyr Tyr Ala Met Asp Tyr
            100                 105                 110

Trp Gly Gln Gly Thr Thr Leu Thr Val Ser Ser Asp Ile Val Ile Thr
        115                 120                 125
```

```
Gln Ala Ala Phe Ser Asn Pro Val Thr Leu Gly Thr Ser Ala Ser Ile
    130                 135                 140

Ser Cys Ser Cys Ser Lys Ser Leu Leu His Ser Asn Gly Ile Thr Tyr
145                 150                 155                 160

Leu Tyr Trp Tyr Leu Gln Arg Pro Gly Gln Ser Pro Gln Leu Leu Ile
                165                 170                 175

Tyr Arg Met Ser Asn Leu Ala Ser Gly Val Pro Asp Arg Phe Ser Gly
            180                 185                 190

Ser Gly Ser Gly Thr Asp Phe Thr Leu Arg Ile Ser Arg Val Glu Ala
            195                 200                 205

Glu Asp Val Gly Val Tyr Tyr Cys Ala Gln Met Leu Glu Arg Pro Tyr
210                 215                 220

Thr Phe Gly Gly Gly Thr Lys Leu Glu Ile Lys
225                 230                 235

<210> SEQ ID NO 157
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Ile Tyr Pro Arg Asp Ser Asp Thr Ser Tyr Asn Gln Lys Phe Lys
1               5                   10                  15

Gly Lys Ala

<210> SEQ ID NO 158
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Asp Ile Val Ile Thr Gln Ala Ala Phe Ser Asn Pro Val Thr Leu Gly
1               5                   10                  15

Thr Ser Ala Ser Ile Ser Cys Ser Cys Ser Lys Ser Leu Leu His Ser
            20                  25                  30

Asn Gly Ile Thr Tyr Leu Tyr Trp Tyr Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Tyr Thr Phe Gly Gly Gly Thr Lys Leu Glu Ile Lys
            100                 105                 110

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 159

Ser Cys Ser Lys Ser Leu Leu His Ser Asn Gly Ile Thr Tyr Leu Tyr
1               5                   10                  15

<210> SEQ ID NO 160
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Val Leu Leu Val Glu Ser Gly Gly Arg Leu Val Gln Pro Lys Gly
1               5                   10                  15

Ser Leu Lys Leu Ser Cys Ala Ala Ser Gly Phe Ser Phe Asn Thr Ile
            20                  25                  30

Thr Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ala Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Phe Cys Val Arg Gly Ile Phe Ser Gly Tyr Val Tyr Ala Met Asp Tyr
            100                 105                 110

Trp Gly Gln Gly Thr Thr Leu Thr Val Ser Ser
        115                 120

<210> SEQ ID NO 161
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Val Val Met Thr Gln Ser Pro Leu Ser Leu Pro Val Ser Val Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 162
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 162

Asp Val Met Leu Val Glu Ser Gly Gly Val Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Ala Leu Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asn Gly Leu Tyr Gly Leu Phe Ala Tyr Trp Gly Gln
            100                 105                 110

Gly Thr Leu Val Thr Val Ser Ala
        115                 120

<210> SEQ ID NO 163
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Leu Ile Arg Asn Lys Ala Asn Gly Tyr Thr Thr Glu Tyr Ser Ala Ser
1               5                   10                  15

Val Lys Gly

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Val Met Thr Gln Thr Ala Pro Ser Ile Pro Val Thr Pro Gly
1               5                   10                  15

Glu Ser Val Ser Ile Ser Cys Arg Ser Ser Thr Ser Leu Leu Glu Ser
            20                  25                  30

Ser Gly Lys His Arg Leu Tyr Trp Phe Leu Gln Arg Pro Gly Gln Ser
        35                  40                  45

Pro Gln Leu Leu Ile Tyr Tyr Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Phe Gly Val Tyr Tyr Cys Met Gln Ser
                85                  90                  95

Leu Glu Tyr Pro Leu Thr Phe Gly Ala Gly Thr Lys Leu Glu Ile Lys
            100                 105                 110

<210> SEQ ID NO 165

```
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Glu Val Lys Leu Val Glu Ser Gly Gly Val Leu Val Lys Pro Gly Gly
1               5                   10                  15

Ser Leu Lys Leu Ser Cys Ala Ala Ser Gly Phe Thr Phe Ser Lys Tyr
            20                  25                  30

Ala Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Ile Tyr Tyr Cys
                85                  90                  95

Thr Arg Glu Gly Gly Tyr Asp Glu Gly Tyr Ala Met Asp Tyr Trp Gly
            100                 105                 110

Gln Gly Thr Thr Leu Thr Val Ser
        115                 120

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Tyr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Arg Thr Phe Gly Gly Gly Thr Lys Leu Glu Ile Lys
            100                 105                 110

<210> SEQ ID NO 167
<211> LENGTH: 910
<212> TYPE: PRT
<213> ORGANISM: Homo sapiens

<400> SEQUENCE: 167

Met Gly Thr Pro Arg Ala Gln His Pro Pro Pro Gln Leu Leu Phe
1               5                   10                  15

Leu Ile Leu Leu Ser Cys Pro Trp Ile Gln Gly Leu Pro Leu Lys Glu
            20                  25                  30
```

-continued

```
Glu Glu Ile Leu Pro Glu Pro Gly Ser Glu Thr Pro Thr Val Ala Ser
             35                  40                  45
Glu Ala Leu Ala Glu Leu Leu His Gly Ala Leu Leu Arg Arg Gly Pro
 50                  55                  60
Glu Met Gly Tyr Leu Pro Gly Ser Asp Arg Asp Pro Thr Leu Ala Thr
 65                  70                  75                  80
Pro Pro Ala Gly Gln Thr Leu Ala Val Pro Ser Leu Pro Arg Ala Thr
                 85                  90                  95
Glu Pro Gly Thr Gly Pro Leu Thr Thr Ala Val Thr Pro Asn Gly Val
            100                 105                 110
Arg Gly Ala Gly Pro Thr Ala Pro Glu Leu Leu Thr Pro Pro Pro Gly
            115                 120                 125
Thr Thr Ala Pro Pro Pro Ser Pro Ala Ser Pro Gly Pro Pro Leu
    130                 135                 140
Gly Pro Glu Gly Gly Glu Glu Thr Thr Thr Ile Ile Thr Thr
145                 150                 155                 160
Thr Thr Val Thr Thr Val Thr Ser Pro Val Leu Cys Asn Asn Asn
                165                 170                 175
Ile Ser Glu Gly Glu Gly Tyr Val Glu Ser Pro Asp Leu Gly Ser Pro
            180                 185                 190
Val Ser Arg Thr Leu Gly Leu Leu Asp Cys Thr Tyr Ser Ile His Val
    195                 200                 205
Tyr Pro Gly Tyr Gly Ile Glu Ile Gln Val Gln Thr Leu Asn Leu Ser
    210                 215                 220
Gln Glu Glu Glu Leu Leu Val Leu Ala Gly Gly Ser Pro Gly Leu
225                 230                 235                 240
Ala Pro Arg Leu Leu Ala Asn Ser Ser Met Leu Gly Glu Gly Gln Val
                245                 250                 255
Leu Arg Ser Pro Thr Asn Arg Leu Leu Leu His Phe Gln Ser Pro Arg
            260                 265                 270
Val Pro Arg Gly Gly Phe Arg Ile His Tyr Gln Ala Tyr Leu Leu
    275                 280                 285
Ser Cys Gly Phe Pro Pro Arg Pro Ala His Gly Asp Val Ser Val Thr
290                 295                 300
Asp Leu His Pro Gly Gly Thr Ala Thr Phe His Cys Asp Ser Gly Tyr
305                 310                 315                 320
Gln Leu Gln Gly Glu Glu Thr Leu Ile Cys Leu Asn Gly Thr Arg Pro
                325                 330                 335
Ser Trp Asn Gly Glu Thr Pro Ser Cys Met Ala Ser Cys Gly Gly Thr
            340                 345                 350
Ile His Asn Ala Thr Leu Gly Arg Ile Val Ser Pro Glu Pro Gly Gly
            355                 360                 365
Ala Val Gly Pro Asn Leu Thr Cys Arg Trp Val Ile Glu Ala Ala Glu
            370                 375                 380
Gly Arg Arg Leu His Leu His Phe Glu Arg Val Ser Leu Asp Glu Asp
385                 390                 395                 400
Asn Asp Arg Leu Met Val Arg Ser Gly Gly Ser Pro Leu Ser Pro Val
                405                 410                 415
Ile Tyr Asp Ser Asp Met Asp Asp Val Pro Glu Arg Gly Leu Ile Ser
            420                 425                 430
Asp Ala Gln Ser Leu Tyr Val Glu Leu Leu Ser Glu Thr Pro Ala Asn
            435                 440                 445
```

-continued

```
Pro Leu Leu Leu Ser Leu Arg Phe Glu Ala Phe Glu Glu Asp Arg Cys
    450                 455                 460

Phe Ala Pro Phe Leu Ala His Gly Asn Val Thr Thr Thr Asp Pro Glu
465                 470                 475                 480

Tyr Arg Pro Gly Ala Leu Ala Thr Phe Ser Cys Leu Pro Gly Tyr Ala
                485                 490                 495

Leu Glu Pro Pro Gly Pro Pro Asn Ala Ile Glu Cys Val Asp Pro Thr
            500                 505                 510

Glu Pro His Trp Asn Asp Thr Glu Pro Ala Cys Lys Ala Met Cys Gly
        515                 520                 525

Gly Glu Leu Ser Glu Pro Ala Gly Val Val Leu Ser Pro Asp Trp Pro
    530                 535                 540

Gln Ser Tyr Ser Pro Gly Gln Asp Cys Val Trp Gly Val His Val Gln
545                 550                 555                 560

Glu Glu Lys Arg Ile Leu Leu Gln Val Glu Ile Leu Asn Val Arg Glu
                565                 570                 575

Gly Asp Met Leu Thr Leu Phe Asp Gly Asp Gly Pro Ser Ala Arg Val
            580                 585                 590

Leu Ala Gln Leu Arg Gly Pro Gln Pro Arg Arg Leu Leu Ser Ser
        595                 600                 605

Gly Pro Asp Leu Thr Leu Gln Phe Gln Ala Pro Pro Gly Pro Pro Asn
    610                 615                 620

Pro Gly Leu Gly Gln Gly Phe Val Leu His Phe Lys Glu Val Pro Arg
625                 630                 635                 640

Asn Asp Thr Cys Pro Glu Leu Pro Pro Pro Glu Trp Gly Trp Arg Thr
                645                 650                 655

Ala Ser His Gly Asp Leu Ile Arg Gly Thr Val Leu Thr Tyr Gln Cys
            660                 665                 670

Glu Pro Gly Tyr Glu Leu Leu Gly Ser Asp Ile Leu Thr Cys Gln Trp
        675                 680                 685

Asp Leu Ser Trp Ser Ala Ala Pro Pro Ala Cys Gln Lys Ile Met Thr
    690                 695                 700

Cys Ala Asp Pro Gly Glu Ile Ala Asn Gly His Arg Thr Ala Ser Asp
705                 710                 715                 720

Ala Gly Phe Pro Val Gly Ser His Val Gln Tyr Arg Cys Leu Pro Gly
                725                 730                 735

Tyr Ser Leu Glu Gly Ala Ala Met Leu Thr Cys Tyr Ser Arg Asp Thr
            740                 745                 750

Gly Thr Pro Lys Trp Ser Asp Arg Val Pro Lys Cys Ala Leu Lys Tyr
        755                 760                 765

Glu Pro Cys Leu Asn Pro Gly Val Pro Glu Asn Gly Tyr Gln Thr Leu
    770                 775                 780

Tyr Lys His His Tyr Gln Ala Gly Glu Ser Leu Arg Phe Phe Cys Tyr
785                 790                 795                 800

Glu Gly Phe Glu Leu Ile Gly Glu Val Thr Ile Thr Cys Val Pro Gly
                805                 810                 815

His Pro Ser Gln Trp Thr Ser Gln Pro Pro Leu Cys Lys Val Thr Gln
            820                 825                 830

Thr Thr Asp Pro Ser Arg Gln Leu Glu Gly Gly Asn Leu Ala Leu Ala
        835                 840                 845

Ile Leu Leu Pro Leu Gly Leu Val Ile Leu Gly Ser Gly Val Tyr
    850                 855                 860
```

```
Ile Tyr Tyr Thr Lys Leu Gln Gly Lys Ser Leu Phe Gly Phe Ser Gly
865                 870                 875                 880

Ser His Ser Tyr Ser Pro Ile Thr Val Glu Ser Asp Phe Ser Asn Pro
                885                 890                 895

Leu Tyr Glu Ala Gly Asp Thr Arg Glu Tyr Glu Val Ser Ile
                900                 905                 910

<210> SEQ ID NO 168
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 169
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 170
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 171
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
        50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 172
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
atagctcttc agggaccatg aarcayctgt ggttcttcct                        40

<210> SEQ ID NO 173
<211> LENGTH: 39

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
atagctcttc agggaccatg gacatacttt gttccacgc                    39

<210> SEQ ID NO 174
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
atagctcttc agggaccatg gacacacttt gctacacac                    39

<210> SEQ ID NO 175
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
atagctcttc agggaccatg tctgtctcct tcctcatct                    39

<210> SEQ ID NO 176
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
atagctcttc agggaccatg gactggacct ggagvatc                     38

<210> SEQ ID NO 177
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
atagctcttc agggaccatg gactggattt ggaggrtc                     38

<210> SEQ ID NO 178
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
atagctcttc agggaccatg gactgcacct ggaggatc                     38

<210> SEQ ID NO 179
<211> LENGTH: 38
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 179
atagctcttc agggaccatg gactggacct ggaggktc                             38

<210> SEQ ID NO 180
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
atagctcttc agggaccatg gagttkggrc tgagctgg                             38

<210> SEQ ID NO 181
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
atagctcttc agggaccatg gagtttkggc tkagctgg                             38

<210> SEQ ID NO 182
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
atagctcttc agggaccatg gaactggggc tccgctgg                             38

<210> SEQ ID NO 183
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
atagctcttc agggaccatg garttggggc tgwgctgg                             38

<210> SEQ ID NO 184
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
atagctcttc agggaccatg gggtcaaccg ccatcctc                             38

<210> SEQ ID NO 185
<211> LENGTH: 44
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 185
atagctcttc agggaccatg gacatgaggg tsccygctca gctc                       44

<210> SEQ ID NO 186
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
atagctcttc agggaccatg gacatgagrg tcctcgctca gctc                       44

<210> SEQ ID NO 187
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
atagctcttc agggaccatg gaagccccag cdcagcttct c                          41

<210> SEQ ID NO 188
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
atagctcttc agggaccatg gaaaccccag cgcagcttct c                          41

<210> SEQ ID NO 189
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
atagctcttc agggaccatg gtgttgcaga cccaggtctt c                          41

<210> SEQ ID NO 190
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
atagctcttc agggaccatg gggtcccagg ttcacctcct c                          41

<210> SEQ ID NO 191
<211> LENGTH: 41
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 191
atagctcttc agggaccatg aggctccytg ctcagctcct g                    41

<210> SEQ ID NO 192
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
atagctcttc ttcgtttgat ctccascttg gtc                             33

<210> SEQ ID NO 193
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
atagctcttc ttcgtttaat ctccagtcgt gtc                             33

<210> SEQ ID NO 194
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
atagctcttc tggctgagga gacggtgacc                                 30

<210> SEQ ID NO 195
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
atagctcttc atgtgacgct gttgtgactc agga                            34

<210> SEQ ID NO 196
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
atagctcttc atgtgaccyt gtgctcactc agtc                            34

<210> SEQ ID NO 197
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 197
gatgctcttc tgggctggcc taggacagtc amcytgg                             37

<210> SEQ ID NO 198
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
atagctcttc atgtgacawt gttctcaccc agtc                                34

<210> SEQ ID NO 199
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
atagctcttc atgtgacatc cagatgacac agwc                                34

<210> SEQ ID NO 200
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
atagctcttc atgtgatrtt gtgatgaccc agwc                                34

<210> SEQ ID NO 201
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
atagctcttc atgtgacatt stgmtgaccc agtc                                34

<210> SEQ ID NO 202
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
atagctcttc atgtgatgtt gtgvtgaccc aaac                                34

<210> SEQ ID NO 203
<211> LENGTH: 34
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 203
atagctcttc atgtgacaca actgtgaccc agtc                                    34

<210> SEQ ID NO 204
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
atagctcttc atgtgayatt ktgctcactc agtc                                    34

<210> SEQ ID NO 205
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
atagctcttc atgtgatatt gtgatraccc aggm                                    34

<210> SEQ ID NO 206
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
atagctcttc atgtgacatt gtaatgaccc aatc                                    34

<210> SEQ ID NO 207
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
atagctcttc atgtgacatt gtgatgwcac agtc                                    34

<210> SEQ ID NO 208
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
atagctcttc atgtgatrtc cagatgamcc agtc                                    34

<210> SEQ ID NO 209
<211> LENGTH: 34
<212> TYPE: DNA
<213> ORGANISM: Artificial Sequence
<220> FEATURE:

<223> OTHER INFORMATION: Description of Artificial Sequence: Synthetic
     primer

<400> SEQUENCE: 209
atagctcttc atgtgatgga gaaacaacac aggc                          34

<210> SEQ ID NO 210
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 210
atagctcttc atgtgacgct gttgtgactc agga                          34

<210> SEQ ID NO 211
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 211
atagctcttc atgtgaccyt gtgctcactc agtc                          34

<210> SEQ ID NO 212
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 212
gatgctcttc gtcgtttbat ttccagcttg g                             31

<210> SEQ ID NO 213
<211> LENGTH: 31
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 213
gatgctcttc gtcgtttat ttccaatttt g                              31

<210> SEQ ID NO 214
<211> LENGTH: 37
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 214
gatgctcttc tgggctggcc taggacagtc amcytgg                       37

<210> SEQ ID NO 215
<211> LENGTH: 34
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 215
atagctcttc atgtgaggtt cdsctgcaac agty                                 34

<210> SEQ ID NO 216
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
atagctcttc atgtcaggtg caamtgmags agtc                                 34

<210> SEQ ID NO 217
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
atagctcttc atgtgavgtg mwgctggtgg agtc                                 34

<210> SEQ ID NO 218
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
atagctcttc atgtcaggtt aytctgaaag agtc                                 34

<210> SEQ ID NO 219
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
atagctcttc atgtgakgtg cagcttcags agtc                                 34

<210> SEQ ID NO 220
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
atagctcttc atgtcagatc cagttsgygc agtc                                 34

<210> SEQ ID NO 221
<211> LENGTH: 34
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 221
atagctcttc atgtcagrtc caactgcagc agyc                                 34

<210> SEQ ID NO 222
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
atagctcttc atgtgaggtg magctasttg agwc                                 34

<210> SEQ ID NO 223
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
atagctcttc atgtgaagtg aagmttgagg agtc                                 34

<210> SEQ ID NO 224
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
atagctcttc atgtgatgtg aacctggaag tgtc                                 34

<210> SEQ ID NO 225
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
atagctcttc atgtcagatk cagcttmagg agtc                                 34

<210> SEQ ID NO 226
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
atagctcttc atgtcaggct tatctgcagc agtc                                 34

<210> SEQ ID NO 227
<211> LENGTH: 34
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 227
atagctcttc atgtcaggtt cacctacaac agtc                                34

<210> SEQ ID NO 228
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
atagctcttc atgtcaggtg cagcttgtag agac                                34

<210> SEQ ID NO 229
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
atagctcttc atgtgargtg magctgktgg agac                                34

<210> SEQ ID NO 230
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gatgctcttc tggccgagga gacggtgacm gtgg                                34

<210> SEQ ID NO 231
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gatgctcttc tggccgcaga gacagtgacc agag                                34

<210> SEQ ID NO 232
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
gatgctcttc tggccgagga gactgtgaga stgg                                34

<210> SEQ ID NO 233
<211> LENGTH: 120
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Thr Ser Gly Gly Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Gly Glu Tyr Ser Ser Gly Trp Ser Phe Asp Tyr Trp Gly Gln
            100                 105                 110

Gly Thr Leu Val Thr Val Ser Ser
        115                 120

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 234

Gly Tyr Thr Phe Thr Gly Tyr Tyr Ile His
1               5                   10

<210> SEQ ID NO 235
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 235

Trp Ile Asn Pro Thr Ser Gly Gly Thr Ser Tyr Ala Gln Lys Phe Gln
1               5                   10                  15

Gly

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 236

Gly Glu Tyr Ser Ser Gly Trp Ser Phe Asp Tyr
1               5                   10

<210> SEQ ID NO 237
<211> LENGTH: 107
<212> TYPE: PRT
<213> ORGANISM: Artificial Sequence
<220> FEATURE:

<223> OTHER INFORMATION: Description of Artificial Sequence: Synthetic
       polypeptide

<400> SEQUENCE: 237

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Leu
                85                  90                  95

Thr Phe Gly Gly Gly Thr Lys Val Glu Ile Lys
            100                 105

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Gln Gln Tyr Asn Asp Trp Pro Leu Thr
1               5

<210> SEQ ID NO 239
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
50                  55                  60

Gln Gly Arg Val Thr Met Thr Arg Asn Thr Ser Ile Gly Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asp Tyr Tyr Gly Ser Gly Ser Tyr Lys Gly His Tyr
            100                 105                 110

Val Met Asp Ala Trp Gly Gln Gly Ala Ser Val Thr Val Ser Ser
        115                 120                 125

<210> SEQ ID NO 240
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 240

Gly Tyr Thr Phe Thr Ser His Asp Ile Asn
1               5                   10

<210> SEQ ID NO 241
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Trp Met Asn Pro Asn Ser Gly Asn Thr Gly Tyr Ala Gln Lys Phe Gln
1               5                   10                  15

Gly

<210> SEQ ID NO 242
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gly Gly Asp Tyr Tyr Gly Ser Gly Ser Tyr Lys Gly His Tyr Val Met
1               5                   10                  15

Asp Ala

<210> SEQ ID NO 243
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg His
            20                  25                  30

Phe Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln His Tyr Thr Asn Trp Pro Leu
                85                  90                  95

Thr Phe Gly Gly Gly Thr Lys Leu Glu Ile Lys
            100                 105

<210> SEQ ID NO 244
<211> LENGTH: 11
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 244

Arg Ala Ser Gln Ser Val Ser Arg His Phe Ala
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln His Tyr Thr Asn Trp Pro Leu Thr
1               5

<210> SEQ ID NO 246
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
caggtgcagt tggtgcagtc tggggctgag gtgaagaagc ctggggcctc agtgaaggtc      60
tcctgcaagg cttctggata caccttcacc ggctactata tccactgggt gcgacaggcc     120
cctggacaag gcttgagtg gatgggatgg atcaaccta ccagtggtgg cacaagctat      180
gcacagaagt tcagggcag ggtcaccatg accagggaca cgtccatcag cacagcctac      240
atggaactga caggctgag atctgacgac acggccgtgt attactgtgc gagaggagag      300
tatagcagtg gctggtcctt tgactactgg ggccagggaa ccctggtcac cgtctcctca     360

<210> SEQ ID NO 247
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 247
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataatgact ggcctctcac tttcggcgga     300
gggaccaagg tggagatcaa a                                                321

<210> SEQ ID NO 248
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 248
caggtgcagc tggtgcagtc tggggctgag gtgaagaagc ctggggcctc agtgaaggtc      60
tcctgcaagg cttctggata caccttcacc agtcatgata tcaactgggt gcgacaggcc     120
actggacaag ggcttgagtg gatgggatgg atgaaccctaa acagtggtaa cacaggctat    180
gcacagaagt tccagggcag agtcaccatg accaggaaca cctccatagg cacagcctac    240
atggagctga gcagcctgag atctgaggac acggccgtgt attactgtgc gagagggggg    300
gattactatg gttcggggag ttataaaggg cactatgtta tggatgcctg gggtcaagga    360
gcttcagtca ccgtctcctc a                                              381

<210> SEQ ID NO 249
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 249
gaaatagtga tgacgcagtc tccagccacc ctgtctgtgt ctccagggga aagagccacc      60
ctctcctgca gggccagtca gagtgttagc agacacttcg cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttattt ctgtcagcac tatactaact ggccgctcac tttcggcgga    300
gggaccaagc tggagatcaa a                                              321
```